(12) United States Patent
Frassica et al.

(10) Patent No.: US 8,764,640 B2
(45) Date of Patent: Jul. 1, 2014

(54) ROTATE-TO-ADVANCE CATHETERIZATION SYSTEM

(71) Applicants: Olympus Endo Technology America Inc., Southborough, MA (US); Olympus Medical Systems Corp., Tokyo (JP)

(72) Inventors: James J. Frassica, Chelmsford, MA (US); Robert E. Ailinger, Norwood, MA (US); Richard M. Andrews, Lincoln, RI (US); Hiroaki Miyoshi, Tokyo (JP)

(73) Assignees: Olympus Medical Systems Corp., Tokyo (JP); Olympus Endo Technology America, Inc., Southborough, MA (US)

( * ) Notice: Subject to any disclaimer, the term of this patent is extended or adjusted under 35 U.S.C. 154(b) by 0 days.

(21) Appl. No.: 13/770,692

(22) Filed: Feb. 19, 2013

(65) Prior Publication Data

US 2013/0165754 A1    Jun. 27, 2013

Related U.S. Application Data

(63) Continuation of application No. 13/192,281, filed on Jul. 27, 2011, now Pat. No. 8,500,628, and a continuation-in-part of application No. 12/987,783, filed on Jan. 10, 2011, now Pat. No. 8,317,678, and a continuation-in-part of application No. 12/924,807, filed on Oct. 5, 2010, and a continuation-in-part of application No. 13/065,469, filed on Mar. 22, 2011, and a continuation-in-part of application No. 11/363,990, filed on Feb. 28, 2006, now Pat. No. 8,377,041, and a continuation-in-part of application No. 12/806,905, filed on Aug. 24, 2010, now Pat. No. 8,366,674, and a continuation-in-part of application No. 12/152,926, filed on May 19, 2008, and a continuation-in-part of application No. 12/467,836, filed on May 18, 2009, now Pat. No. 8,343,040, and a continuation-in-part of application No. 12/467,907, filed on May 18, 2009, now Pat. No. 8,235,942, and a continuation-in-part of application No. 13/100,098, filed on May 3, 2011, now Pat. No. 8,574,220.

(60) Provisional application No. 61/330,435, filed on May 3, 2010, provisional application No. 61/330,442, filed on May 3, 2010, provisional application No. 61/330,450, filed on May 3, 2010.

(51) Int. Cl.
*A61B 1/00* (2006.01)
*A61B 1/307* (2006.01)
*A61M 25/00* (2006.01)

(52) U.S. Cl.
CPC .............. *A61B 1/307* (2013.01); *A61B 1/00073* (2013.01); *A61B 1/0016* (2013.01); *A61M 25/0017* (2013.01); *A61M 2025/006* (2013.01)
USPC ............................................. 600/137; 600/101

(58) Field of Classification Search
CPC .. A61B 1/00073; A61B 1/0016; A61B 1/307; A61M 25/0017; A61M 2025/006
USPC ................................................... 600/101, 137
See application file for complete search history.

(56) References Cited

U.S. PATENT DOCUMENTS

| | | | |
|---|---|---|---|
| 6,666,874 B2 | 12/2003 | Heitzmann et al. | |
| 2005/0272976 A1* | 12/2005 | Tanaka et al. | 600/114 |
| 2007/0038021 A1 | 2/2007 | Kura et al. | |
| 2007/0055097 A1 | 3/2007 | Kura et al. | |
| 2007/0167684 A1 | 7/2007 | Toyama | |
| 2007/0197860 A1* | 8/2007 | Ishizaki | 600/101 |
| 2008/0183033 A1 | 7/2008 | Bern et al. | |
| 2008/0262305 A1 | 10/2008 | Omoto | |
| 2008/0283033 A1 | 11/2008 | Michaud et al. | |

| | | | |
|---|---|---|---|
| 2009/0012359 A1 | 1/2009 | Tanaka et al. | |
| 2009/0209812 A1 | 8/2009 | Omoto | |
| 2009/0281384 A1 | 11/2009 | Tsumaru et al. | |
| 2012/0053410 A1 | 3/2012 | Torisawa | |
| 2012/0136382 A1* | 5/2012 | Kugler et al. | 606/185 |
| 2013/0102847 A1* | 4/2013 | Moriyama | 600/114 |
| 2013/0102848 A1* | 4/2013 | Moriyama | 600/114 |

FOREIGN PATENT DOCUMENTS

| | | |
|---|---|---|
| JP | 51-073884 | 12/1974 |
| JP | 53-117416 | 10/1978 |
| JP | 54-078883 | 6/1979 |
| JP | 60-056488 | 12/1985 |
| JP | 01-227737 | 9/1989 |
| JP | 07-507697 | 8/1995 |
| JP | 2005-319036 | 11/2005 |
| JP | 2005-319121 | 11/2005 |
| JP | 2005-329000 | 12/2005 |
| JP | 2006-034627 | 2/2006 |
| JP | 2006-218235 | 8/2006 |
| JP | 2006-523513 | 10/2006 |
| JP | 2007-185381 | 7/2007 |
| JP | 2007-185394 | 7/2007 |
| JP | 2007-319547 | 12/2007 |
| JP | 2008-068025 | 3/2008 |
| JP | 2008-188360 | 8/2008 |
| JP | 2009-254554 | 11/2009 |
| JP | 2011-520563 | 7/2011 |
| WO | 2004/091689 | 10/2004 |
| WO | 2005/089628 | 9/2005 |
| WO | 2005/110197 | 11/2005 |
| WO | 2006/125187 | 11/2006 |
| WO | 2009/143077 | 11/2009 |

OTHER PUBLICATIONS

Japanese Final Office Action, mailed Mar. 11, 2014, issued in corresponding Japanese Patent Application No. 2011-510622.

* cited by examiner

*Primary Examiner* — Nicholas Lucchesi
*Assistant Examiner* — Gerald Landry, II
(74) *Attorney, Agent, or Firm* — Kenyon & Kenyon LLP

(57) ABSTRACT

An apparatus for accessing a bodily passageway includes: an endoscope including an insertion portion configured to inserted into the bodily passageway; a drive tube including a lumen configured to receive the endoscope; a helically-wound thread disposed on an outer wall of the drive tube and configured such that rotation of the drive tube causes the drive tube with the endoscope to move along the passageway; a flexible drive shaft configured to transfer rotary motion generated by a power supply; and a rotatable drive collar disposed on the endoscope and configured to rotate the drive tube relative to the endoscope, the rotatable drive collar including a stator, a rotor rotatable over the stator and detachably coupled to the drive tube, a rotary gear configured to transfer the rotary motion from the flexible drive shaft to the rotor to rotate the drive tube, and a watertight seal disposed between the stator and the rotor.

10 Claims, 77 Drawing Sheets

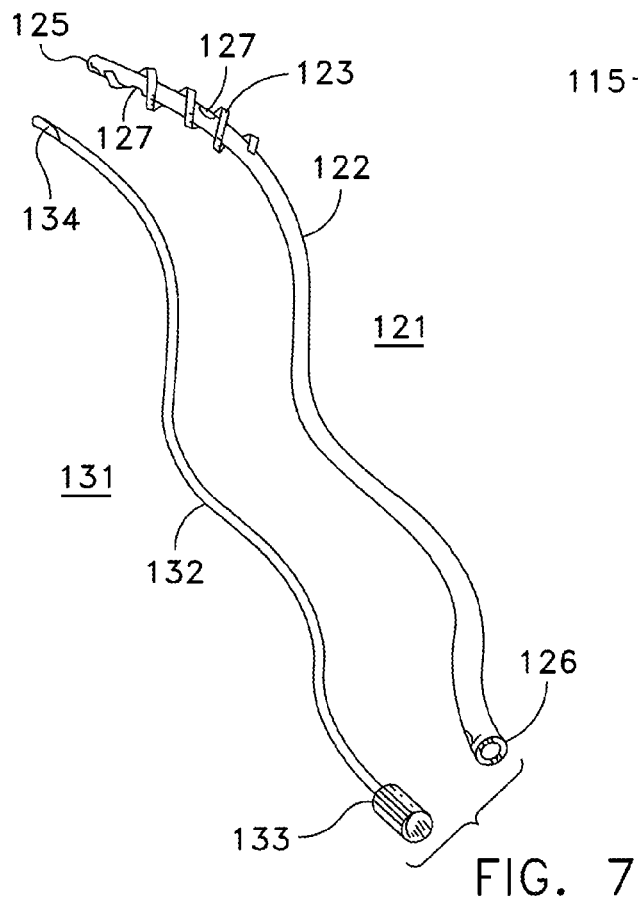
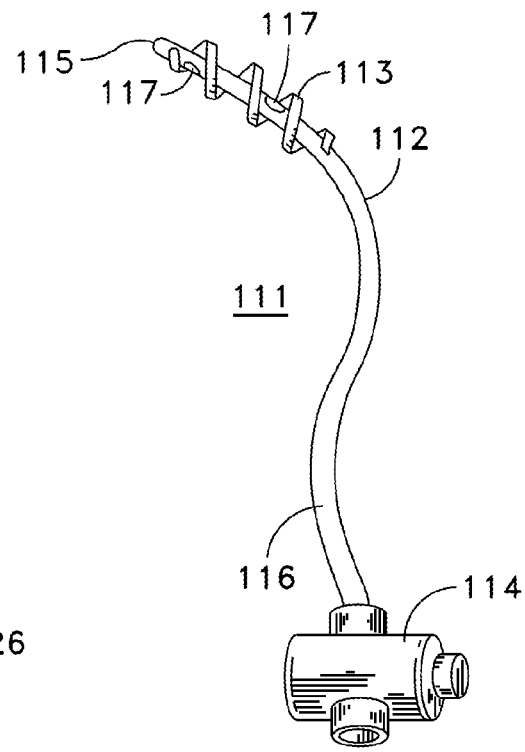
FIG. 7
FIG. 5
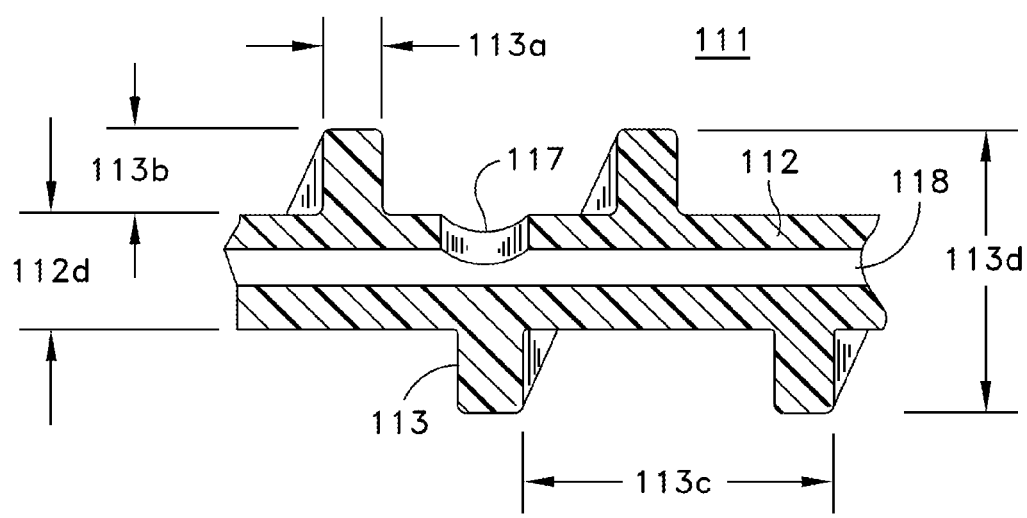
FIG. 6

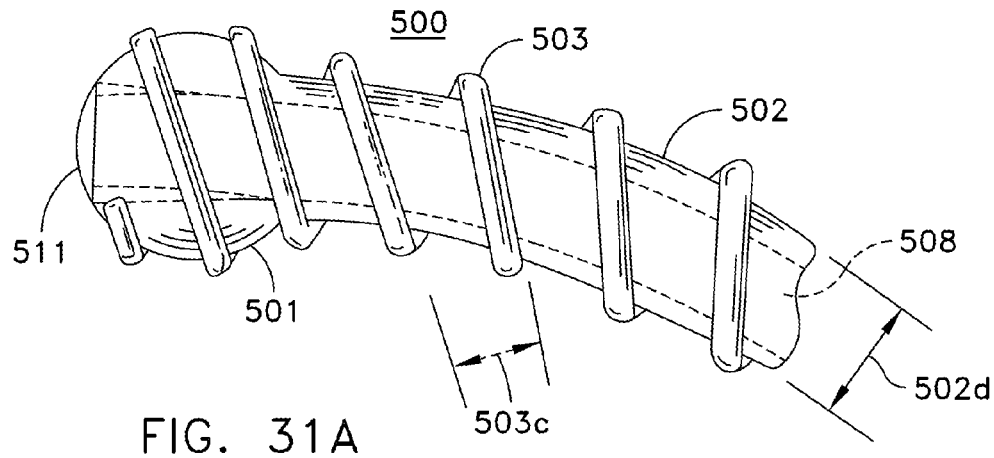
FIG. 31A
FIG. 31B
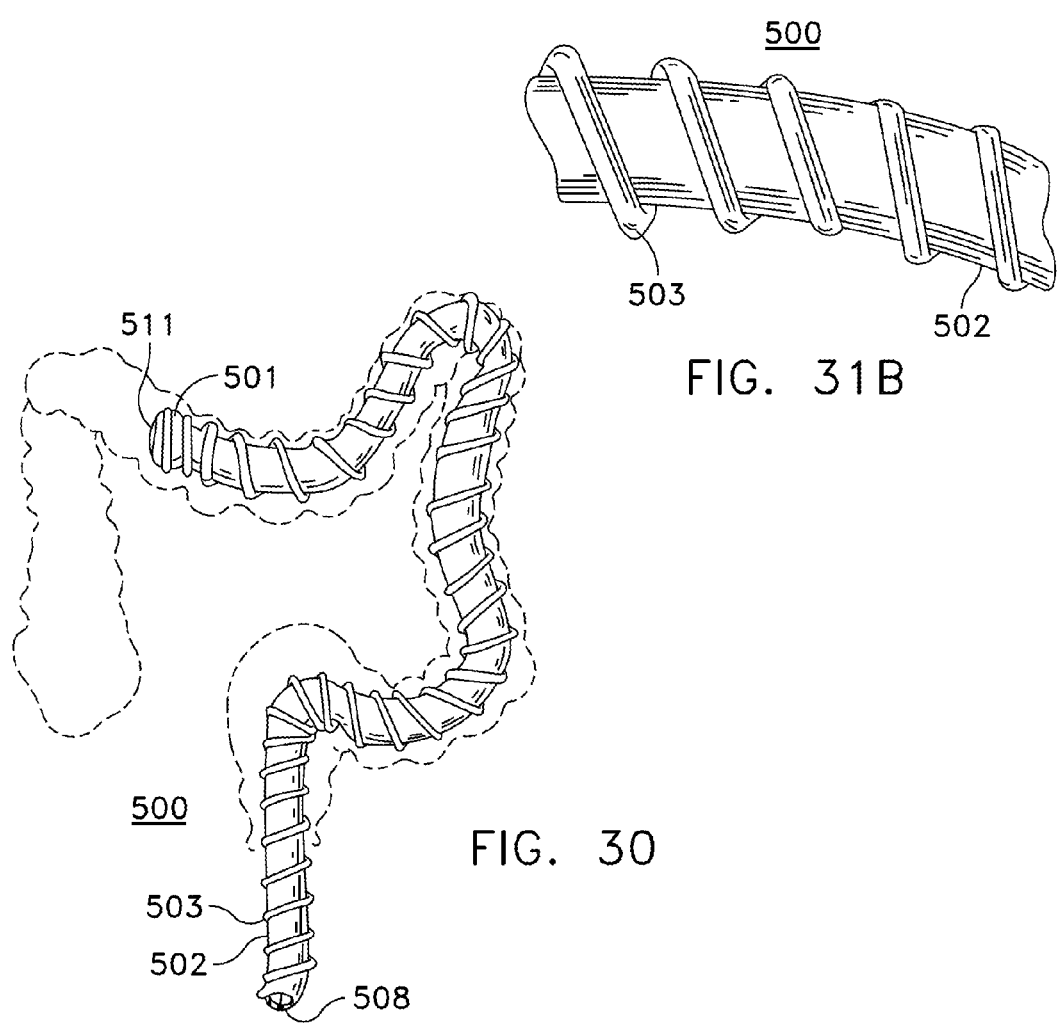
FIG. 30

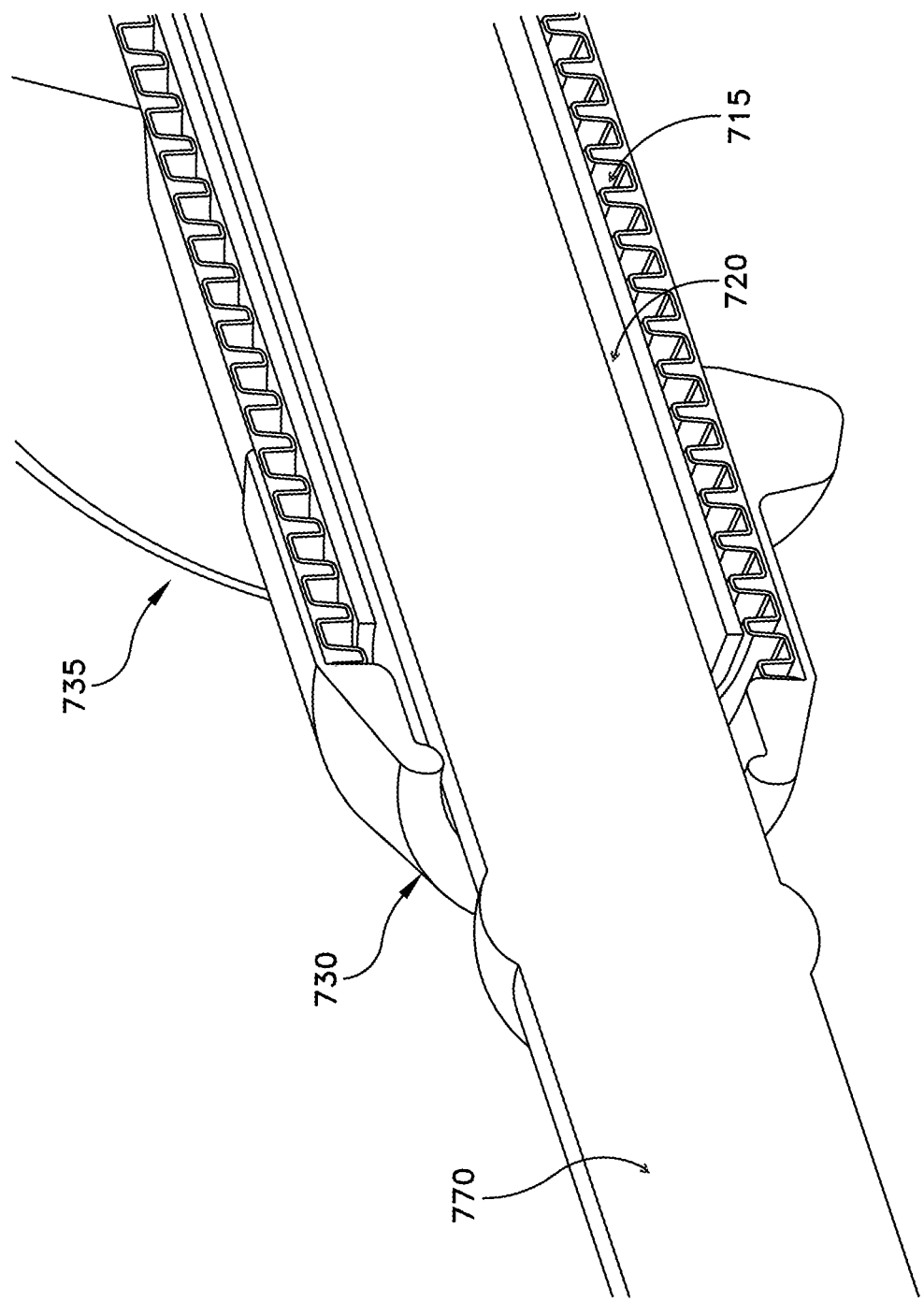

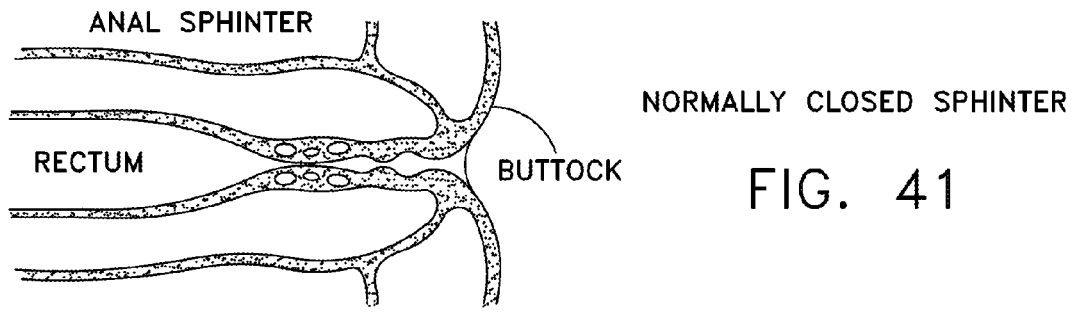
FIG. 41 — NORMALLY CLOSED SPHINCTER
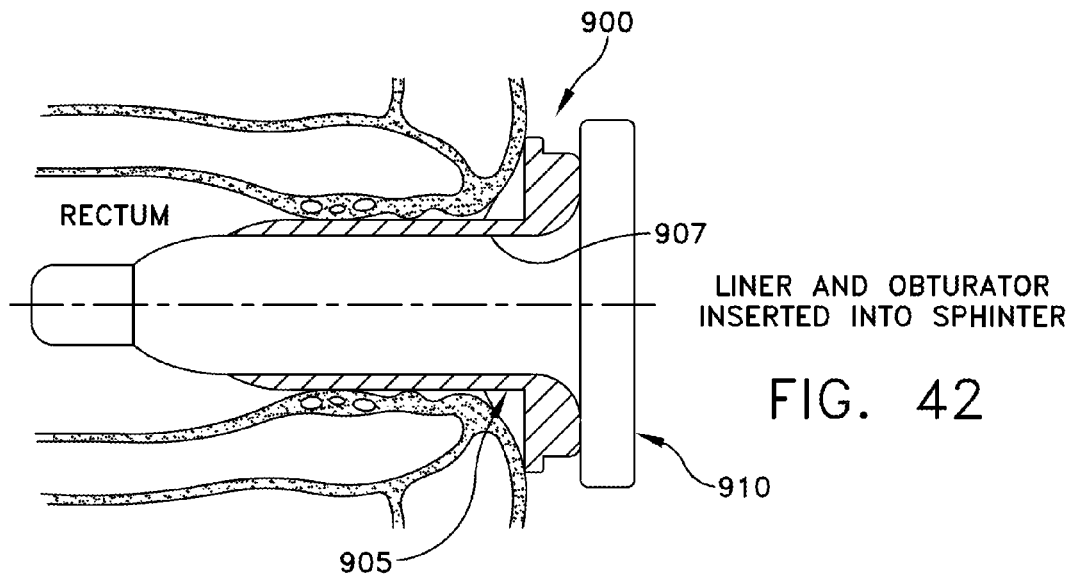
FIG. 42 — LINER AND OBTURATOR INSERTED INTO SPHINCTER
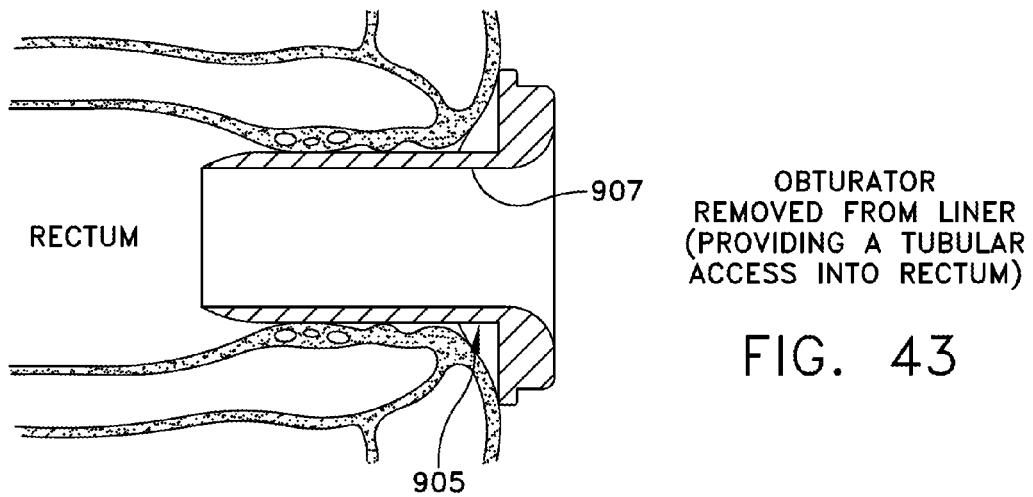
FIG. 43 — OBTURATOR REMOVED FROM LINER (PROVIDING A TUBULAR ACCESS INTO RECTUM)

ROTATE-TO-ADVANCE CATHETERIZATION SYSTEM WITH POWERED DRIVE

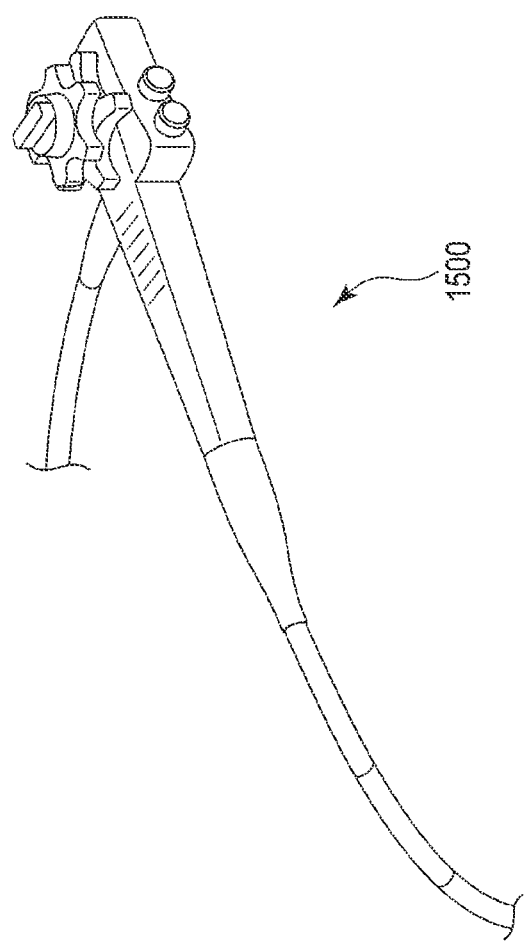
F I G. 65

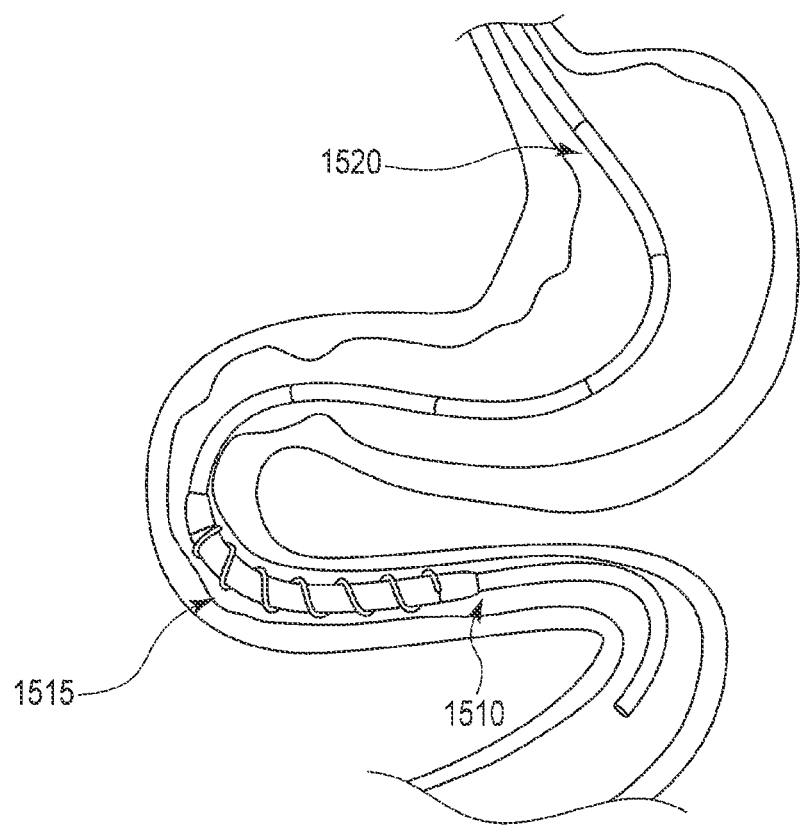
F I G. 70

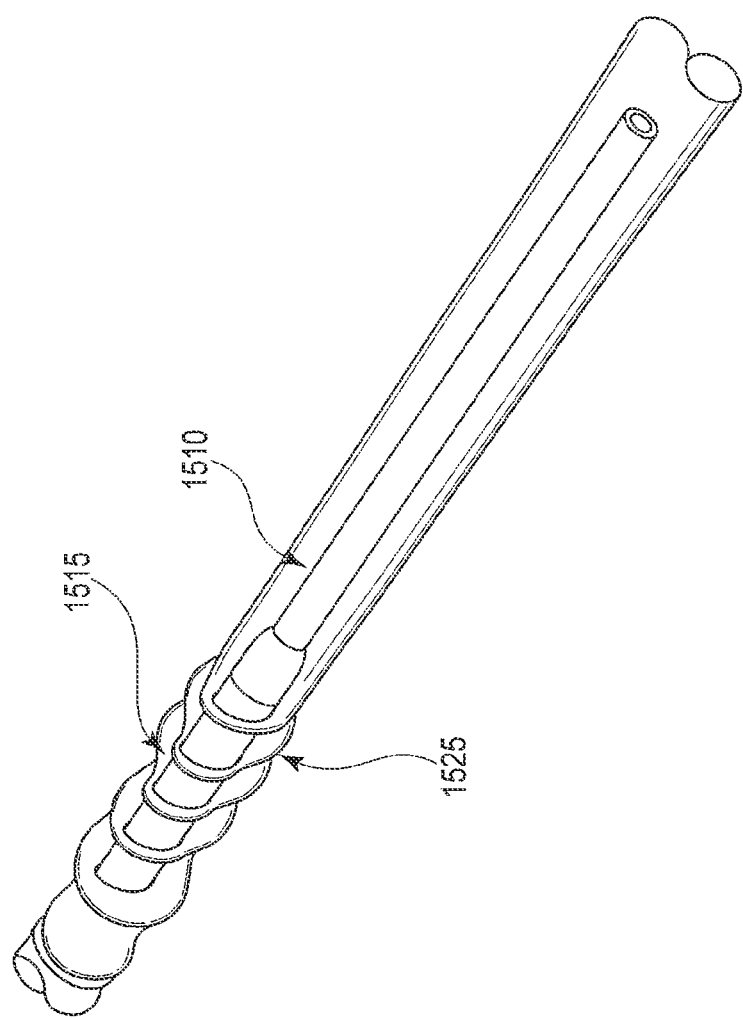
F I G. 71

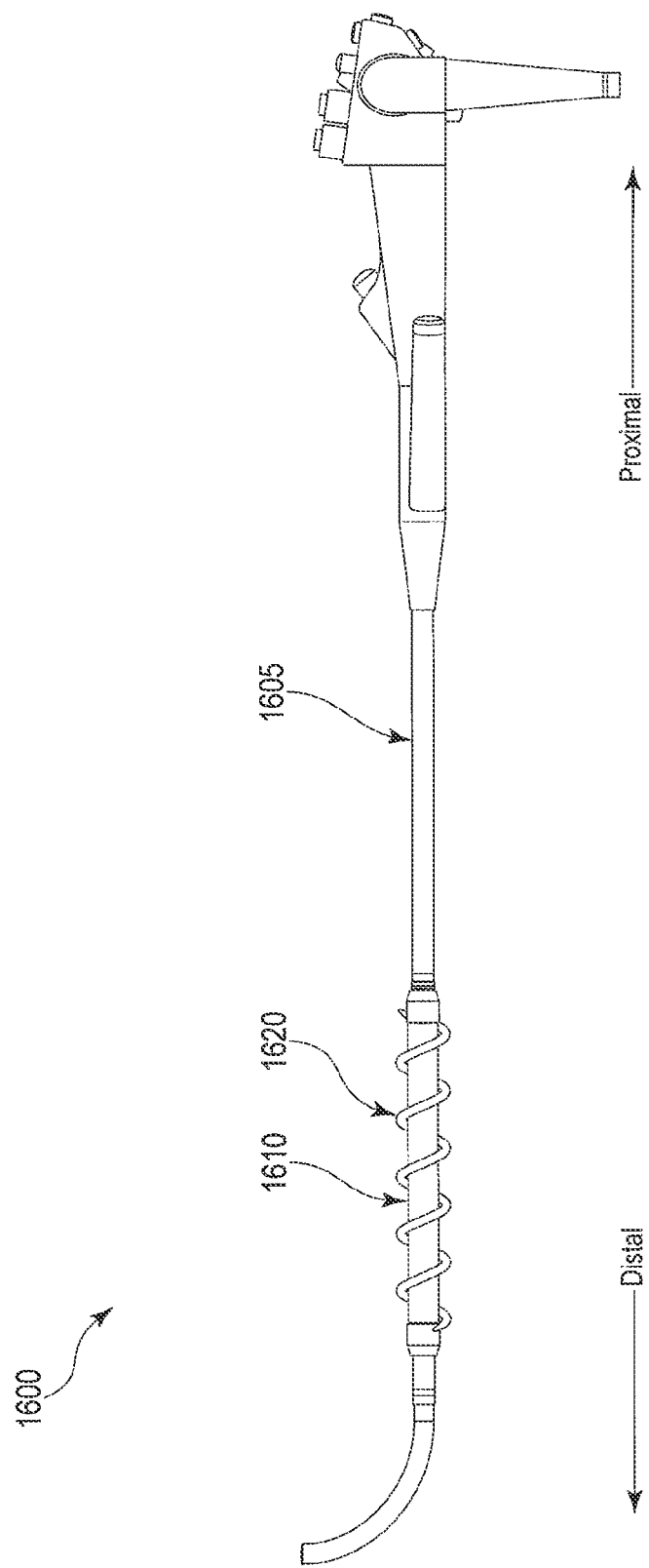
F I G. 75

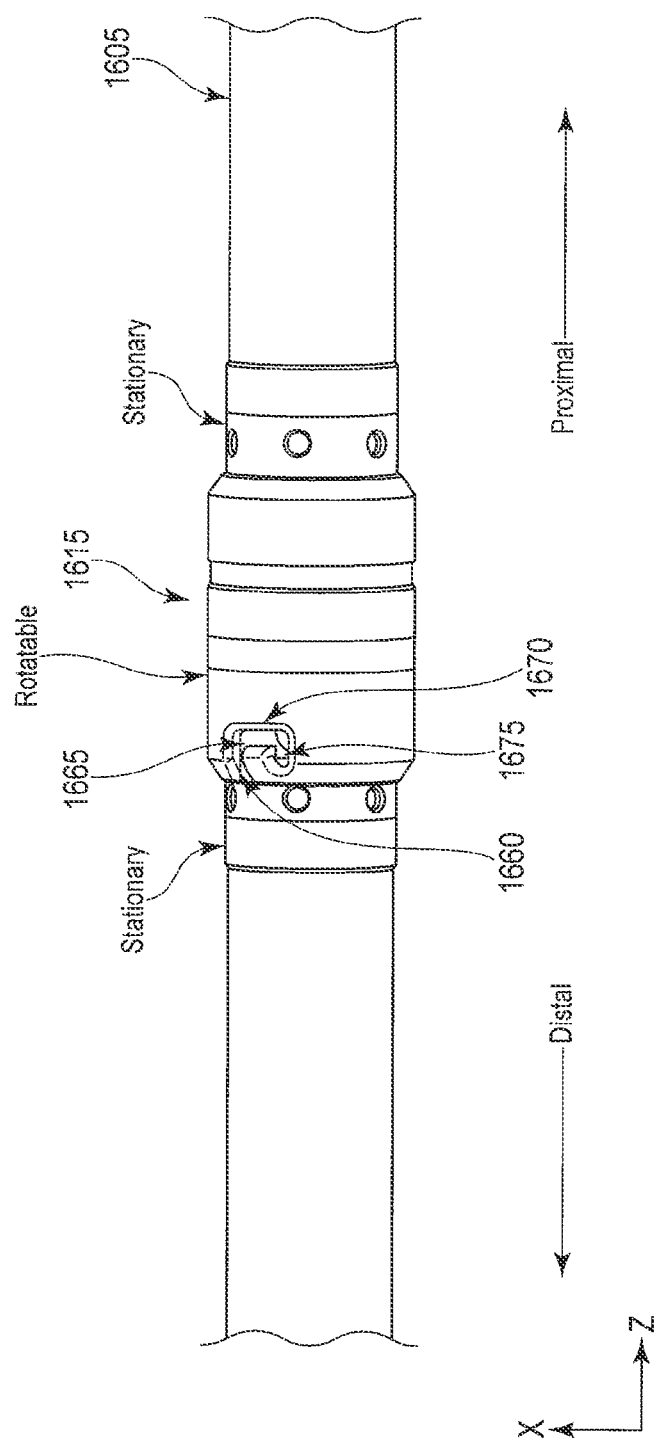
F I G. 78

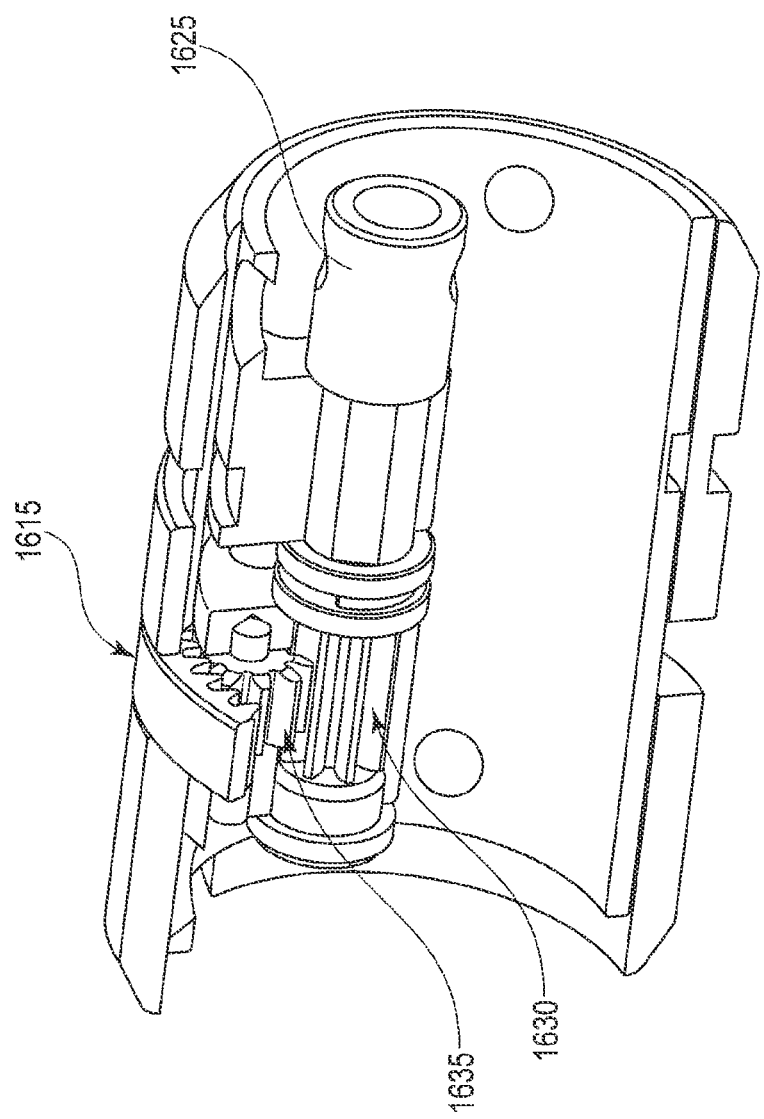
F I G. 79

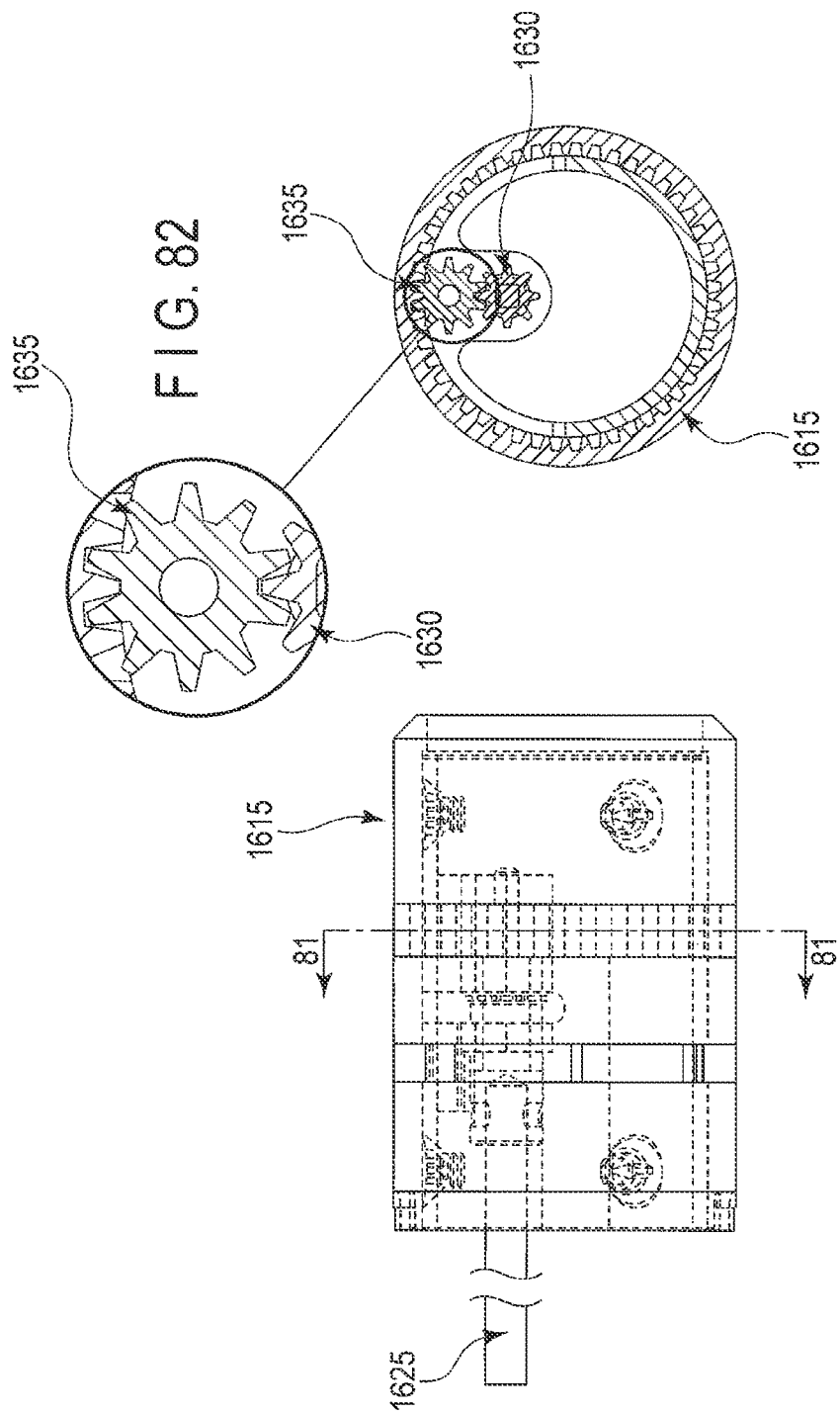

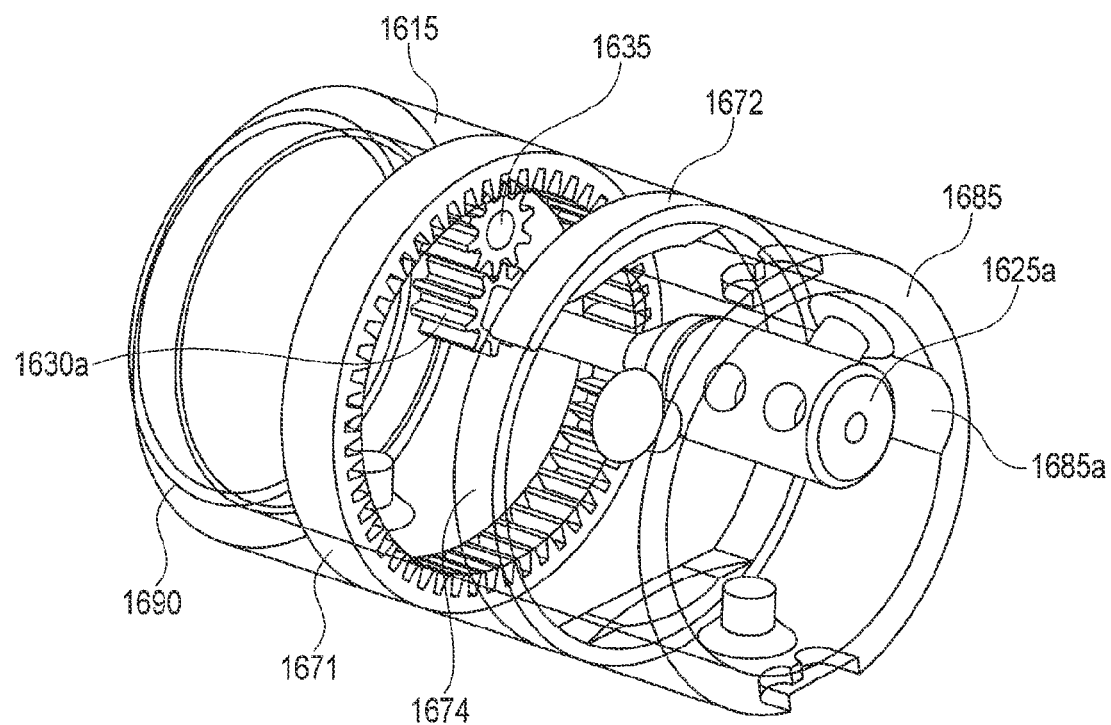
F I G. 89

(SECTION A-A)

(SECTION C-C)

ROTATE-TO-ADVANCE CATHETERIZATION SYSTEM

CROSS-REFERENCE TO RELATED APPLICATIONS

This patent application:

(i) is a continuation of pending prior U.S. patent application Ser. No. 13/192,281, filed on Jul. 27, 2011;

(ii) is a continuation-in-part of pending prior U.S. patent application Ser. No. 12/987,783, filed on Jan. 10, 2011;

(iii) is a continuation-in-part of pending prior U.S. patent application Ser. No. 12/924,807, filed on Oct. 5, 2010;

(iv) is a continuation-in-part of pending prior U.S. patent application Ser. No. 13/065,469, filed on Mar. 22, 2011;

(v) is a continuation-in-part of pending prior U.S. patent application Ser. No. 11/363,990, filed on Feb. 28, 2006;

(vi) is a continuation-in-part of pending prior U.S. patent application Ser. No. 12/806,905, filed on Aug. 24, 2010;

(vii) is a continuation-in-part of pending prior U.S. patent application Ser. No. 12/152,926, filed on May 19, 2008;

(viii) is a continuation-in-part of pending prior U.S. patent application Ser. No. 12/467,836, filed on May 18, 2009;

(ix) is a continuation-in-part of pending prior U.S. patent application Ser. No. 12/467,907, filed on May 18, 2009;

(x) is a continuation-in-part of pending prior U.S. patent application Ser. No. 13/100,098, filed on May 3, 2011; which (xi) claims the benefit of prior U.S. Provisional Patent Application Ser. No. 61/330,435, filed on May 3, 2010, prior U.S. Provisional Patent Application Ser. No. 61/330,442, filed on May 3, 2010, and prior U.S. Provisional Patent Application Ser. No. 61/330,450, filed on May 3, 2010.

Each of the above-identified patent applications is hereby incorporated in its entirety by reference thereto.

FIELD OF THE INVENTION

The present invention relates to apparatus and methods for catheterization and related treatments of the genitourinary and gastrointestinal passages of mammals. More particularly, the present invention relates to catheters, dilators, occluders, stents, suprapubic catheters, camera introducers and related medical devices subject to being proximally propelled and directed for advancement and control in mammalian genitourinary and gastrointestinal passages.

BACKGROUND

In most mammals, mucous membranes line all those passages by which the internal parts communicate with the exterior, and are continuous with the skin at the various orifices of the surface of the body. The mucous membranes are soft and velvety, and very vascular, and their surface is coated over by their secretion, mucus, which is of a tenacious consistency, and serves to protect them from the foreign substances introduced into the body with which they are brought in contact.

Mucous membranes are described as lining the two primary mammalian tracts, i.e., the genitourinary and the gastrointestinal—and all, or almost all, mucous membranes may be classified as belonging to, and continuous with, the one or the other of these tracts.

Catheterization of any of these bodily passages may at times be useful or necessary.

Urinary outlet problems have presumably been around for as long as humans. History has the ancient Chinese using onion stalks to relieve people of acute urinary retention. Literature refers to such problems as far back as 206 B.C., more than 2000 years ago. The ancient Romans are known to have used catheters, which are believed to have been first invented by Erasistratus, a Greek doctor in the third century B.C. The Roman catheters were fine tubes made of bronze. The Roman gynecologist Soranus describes how catheters could be used to push stones out of the way and back into the cavity of the bladder, thus restoring urine flow. Excavations in Pompeii unearthed several bronze catheters. These instruments were well constructed but relatively simple and showed that catheter designs changed little from the period of 79 A.D. until around 1700 A.D.

However, during the $18^{th}$ and 19th centuries, catheter construction became more complex, with an intensified search taking place for an appropriate substance that would be at once flexible, non-irritating and functional. England, France, and the United States all had individuals and companies deeply involved with urinary catheters during this period. Many variations were produced, but they all caused significant stress on the patient when these rigid devices were pushed into the urethra. The first practical breakthrough was made by the French using gum elastic catheters—a catheter that would bend better in the urethral channel and not scour the mucosa as much in the process.

Charles Goodyear improved upon what the French had produced when he successfully vulcanized crude rubber. The problem of manufacturing an instrument which was both sufficiently rigid to enable it to be pushed through the urethra and into the bladder, and yet flexible enough to negotiate the path, had at last reached the point of practicality, notwithstanding its shortcomings. At that time, and even to this day, a functional urethral catheter is frequently defined as being one that is flexible enough to negotiate the bends of the urethra and stable enough to be pushed through the length of the urethral passage.

The French urologist J. J. Cazenave, with the hopes that his country would regain leadership in the catheter field, dedicated 25-30 years of his life improving the flexible durable catheter. This effort was in the late 1800's and Cazenare's catheter, made of decalcified ivory, was a dated device, but it nonetheless shows the consistency of the state of the art wherein catheters are pushed into and negotiated along the urethral passage toward the bladder.

During the past 300 years or so, intensified catheter development efforts were stimulated by professional pride, national pride and financial rewards. These efforts yielded many improvements, such as changes to size, curve shape, materials of construction, smoothness, lubricants, coatings, combinations of materials, physical properties, chemical properties and more—yet all these improvements subscribed to the basic principle of external push-to-advance catheter deployment.

The catheters of the prior art are generally large and stiff, difficult and uncomfortable to administer, and uncomfortable to wear for extended periods of time. There is a degree of skill, tolerance and patience required from medical personnel installing the catheters that takes much time, training and practice to learn. The difficulty, discomfort, risk of injury and infection, inhibition and inconvenience of the methods and apparatus of the prior art results in the deprivation, for many patients, of the freedom to work, play and travel as do unaffected people.

The anatomy of the adult male urinary tract, as illustrated in FIG. 1, has a bladder 4 where urine is collected prior to exiting the body via the urethra 6. The bladder 4 converges into the urethra 6 at a muscular exit called the bladder neck 5. Approximately the first inch of the urethra 6 lies within the prostate 7, which is a chestnut-sized gland. The next approximately half inch of the urethra passes through the external sphincter 8, which is the muscular flow valve that controls the release of urine. The remaining six inches of the urethra 6 lie in a spongy zone, exiting the body at the meatus 9.

The normal process of emptying the bladder can be interrupted by two causes. One is bladder outlet obstruction, and the other is failure of the nerves linking the bladder to the brain. The most frequent cause of bladder outlet obstruction in males is enlargement of the prostate gland by hypertrophy or hyperplasia. In older males, it is not uncommon for a progressive enlargement of the prostate to constrict the prostate urethra. This condition, known as benign prostatic hyperplasia (BPH), can cause a variety of obstructive symptoms, including urinary hesitancy, straining to void, decreased size and force of the urinary stream and, in extreme cases, complete urinary retention possibly leading to renal failure.

The most common surgical intervention for BPH, transurethral resection of the prostate, or TURP, has a lengthy recovery period of up to one year, and presents a high operative risk for complications such as sexual dysfunction. Up to 10% of those subjected to such surgery are left with mild to moderate stress incontinence. Approximately 400,000 patients in the United States, and approximately 500,000 patients internationally, were diagnosed in 1994 with BPH or cancer-induced bladder outlet obstructions that were sufficiently severe to warrant TURP or alternative surgery, according to industry sources.

Because of the high costs, medical risks and quality of life compromises associated with TURP, new technologies have begun to challenge TURP's position as the standard treatment for severe BPH. Recently, the U.S. Food and Drug Administration (FDA) approved two drugs, tera zosin hydrochloride and rinasteride, to treat BPH. However, these drugs generally do not improve symptoms for six to nine months after treatment begins, and are not without side effects.

Urethral strictures are another cause of outlet obstruction, often due to fibrous tissue growth resulting from reaction to catheters or cystoscopes or from injury, birth defects or disease, and are commonly treated by urethral dilation, catheterization or surgery. Men with urethral strictures also experience a limited ability to urinate, which may cause extreme discomfort and, if left untreated, may cause complications that necessitate catheterization. Approximately 50,000 patients in the United States were diagnosed with recurrent urethral strictures in 1994, according to industry sources. It is estimated that approximately 75,000 additional patients were diagnosed internationally.

Women suffer from urinary incontinence (UI) far more often than men and at a younger age, primarily because of the stress associated with pregnancy and childbirth, the shorter length of the female urethra, and the absence of a prostate. The U.S. Department of Health and Human Services (HHS) estimates that the involuntary loss of urine affects approximately 10 million Americans, of which 8.5 million are women. Seven million of these women are non-institutionalized, or community-dwelling.

For women between the ages of 15 and 64, the prevalence of urinary incontinence is estimated to range from 10 to 25 percent of the population. For non-institutionalized persons over the age of 60, the prevalence of urinary incontinence ranges from 15 to 30 percent, with the prevalence in women twice that of men.

The involuntary loss of urine can be caused by a variety of anatomical and physiological factors. The type and cause of urinary incontinence is important to how the condition is treated and managed. The two broad categories of urinary incontinence are urge and stress incontinence. Some people suffer from what is termed mixed incontinence, or a combination of stress and urge incontinence.

Urge incontinence is the involuntary loss of urine associated with an abrupt and strong desire to void. In most cases, urge incontinence is caused by involuntary detrusor (the smooth muscle in the wall of the bladder) contractions or over-activity. For many people, urge incontinence can be satisfactorily managed with pharmaceuticals.

The more frequently occurring stress incontinence is the involuntary loss of urine caused by movement or activity that increases abdominal pressure. The most common cause of stress incontinence is hypermobility or significant displacement of the urethra and bladder neck during exertion. A less frequent cause of stress incontinence is intrinsic urethral sphincter deficiency (ISD), a condition in which the sphincter is unable to generate enough resistance to retain urine in the bladder.

Females, and males with no benign prostatic hyperplasia condition, might also have the inability to empty their bladder because of the nerves linking the bladder to the brain. This condition is known as neuropathic bladder, and may occur in a wide variety of conditions which include spina bifida, multiple sclerosis, spinal injury, slipped disc and diabetes. When these and other problems prevent the bladder from effectively controlling urine, there are a number of treatment options. They are catheters, dilators, occluders, and stents.

Indwelling Foley-Type Catheters

During continuous catheterization, an indwelling catheter is retained in the bladder by a water-filled balloon. The indwelling catheter drains urine continuously from the bladder into a bag which is attached to the leg or bed. The bag has a tap so that the urine can be emptied at intervals. The catheter is usually inserted by a doctor or nurse and changed about every four to six weeks. But difficulty in placement has always been inherent in this design. This is due to the traditional "push to advance" technology which necessitates a relatively stiff, thick-walled catheter to traverse the delicate mucosal-lined urethra.

Often the French (unit of measurement) size of the catheter is dictated by the need for stiffness to insert rather than the lumen size needed to pass urine. A 14 French or smaller Foley catheter is rarely used because catheters of this size lack the column strength needed to push the catheter along the full length of the urethra into the bladder.

The larger French Foley catheters are painful to place, uncomfortable when indwelling, and require a highly-skilled care provider to insert.

Intermittent Catheters

During intermittent catheterization, a simple catheter made of plastic, rubber, or metal is inserted by the patient or a helper for just long enough to empty the bladder completely, which is typically about one minute. These temporary catheters are usually smaller in diameter and stiffer than an indwelling catheter of the same size. This stiffness can make catheterization difficult in men because the male urethra is long and has an acute bend within the prostate. Also, when the external sphincter is reached, the sphincter muscle will contract, making passage difficult. Most patients learn to catheterize themselves and thereby gain a large degree of independence. This process is repeated about every 3-4 hours during the day and occasionally as needed at night.

Intermittent catheterization is mainly used by people who are incontinent due to a neuropathic bladder. Intermittent catheterization may also be utilized by people who cannot empty their bladder because the bladder muscle is weak and does not contract properly.

Suprapubic Catheters

In some patients, an alternate apparatus and method used to maintain long term drainage of the bladder is the use of a suprapubic tube.

Suprapubic catheterization of the bladder is performed via transabdominal puncture which enters the body above the pubic arch and is directed into the bladder using ultrasound or fluoroscopy to guide the trocar introducer and suprapubic catheter. The trocar introducer is then removed when proper catheter placement within the bladder is confirmed, leaving the drainage catheter in place.

Long term drainage may require the fixation of the catheter at the skin using standard adhesive-based interface components to address mechanical fixation, infection control, and skin compatibility. The distal end of the catheter is commonly contained within the bladder by an inflated balloon, or by winged-shaped tip configurations which expand within the bladder, or by pre-shaped curved catheter tips which curl to their original J-shape when stiffening wire is removed from the catheter lumen.

A problem with this form of distal end emplacement through the bladder wall is that it is only unidirectional; that is, it only resists the inadvertent pulling out of the tip of the catheter from the wall of the bladder, while allowing the catheter to freely pass further into the bladder, and to back out up to the point of the containment structure. This continuing catheter motion in and out of the bladder puncture site may irritate tissue and cause infection or other difficulty at the bladder-catheter interface. Urine is especially irritating to most parts of the human body that are outside of the urinary tract.

Dilators

Dilation is accomplished by pushing successively larger urethral dilation tubes through the urethra so as to increase the size of the urethral lumen, a procedure which is painful and traumatic to the patient. Surgical treatment of strictures involves surgical risks as well as complications, including infection, bleeding and restenosis, which frequently requires further treatment.

In general, the current art of dilators has also changed little over the passage of time. A shaft with an increasing taper, bulbous structure, or enlarged end is pushed from without the passage to advance the tool through the restricted passage, thus forcing, by longitudinally-applied pressure, the lateral expansion of the passage walls. This push-to-advance method necessitates a stiff shaft which has all the same limitations as traditional catheters. Catheters inherently provide a degree of this dilatorial function to the extent that the passage is opened sufficiently to accommodate the catheter.

Occluders

Occluders are used in some cases to control incontinence. Occluders of the prior art are constructed and applied with the same push-to-advance concept as the catheters and dilators described above, and hence suffer from the same disadvantages. The basic occluder is a bulb or plug on a shaft which is inserted within the urethra to stop or prevent the normal flow of urine through the urethra, or driven all the way into the bladder, for example, and allowed to seat as a plug at the neck of the urethra to prevent the flow of urine from the bladder.

Stents

A stent is a tubular metallic mesh device that is implanted in. to open and support a stricture so as to allow for urine flow. The stent body is between 3.5 cm and 6.5 cm in length, depending on the anatomy, and is expandable by design to anchor in place. The stent, being a mesh, has openings that allow the tissue to grow through the wall, making removal difficult and causing encrustation that reduces urine flow.

Intraurethral Valved Catheters

An intraurethral valved catheter is a device that is implanted to control the flow of urine by means of an integral valve that is remotely actuated. Since the entire catheter length is within the urethra, the chance for external infection is reduced. The anchoring mechanism of current designs is accomplished with balloons, or "petal-like" projections from the catheter. Both of the aforementioned designs are complicated to install and difficult to remove and, if the valve fails, leaves the patient in a painful and dangerous situation.

Patents in the Prior Art

There has been patent activity in the prior art indicating dissatisfaction with the push-to-advance methodology. Catheters have been adorned with a wide assortment of spiral and threaded features described as intended to ease the trauma and pain of what clearly remained a push-in device. Alvord's U.S. Pat. No. 207,932, Peyret's French Pat. No. 564,832, Hayes' U.S. Pat. No. 1,644,919, and Jacoby's U.S. Pat. No. 1,888,349 are representative of these. In all cases, these disclosures fail to recognize that the basic push-to-advance technique is fundamentally flawed and should be abandoned, and fail to resolve the critical features of structure necessary for rotational advancement as a substitute for the push-to-advance method.

Other art reveals the use of spiral features for different purposes. For example, Spinosa's U.S. Pat. No. 3,815,608 discloses a catheter with a thread designed to hold the urethral wall away from the shaft so as to allow urine to flow around the outside of the catheter. Such disclosures likewise reveal a reliance on push-in methods, or an assumption that such structures can be pulled out without regard to the spiral features, again failing to recognize rotation as a viable substitute for pushing, and failing to resolve the critical features of structure necessary for effective rotational advancement.

As a further indication of the failure of the prior art to provide effective improvements to traditional push-in methods, there is no apparent indication among the products commercially available, or in the medical practices known to the Applicants, that any of these spirally-ornamented devices were ever found to be clinically viable.

Gastrointestinal Endoscopes

The current device used for inspection and treatment of the GI (gastrointestinal) tract is a flexible endoscope. This device takes a high level of skill to use, is difficult to maneuver and can be very painful for the patient, due to the basic push-to-advance design that has not changed since the device was invented in the early 1960's. The distal tip of the endoscope typically has the following parts:

1. a channel opening for suction and passage of accessories;
2. a light guide lens to distribute light from a fiberoptic bundle to illuminate the visual field;
3. an objective lens to focus an image of the mucosa onto the face of a fiber optic image bundle for transmission back to an eyepiece; and
4. an air/water jet, which supplies air to inflate the organ being observed, and water to clean off the image (i.e., objective) lens.

The so-called "bending section" is the distal end of the tube, ranging from approximately 8-15 cm long, which can articulate so as to steer the scope as it is pushed inward and is controlled by a cable mechanism that is connected to control knobs on the proximal handle.

The so-called "insertion tube", which makes up the rest of the endoscope's 60-150 cm length, is not capable of controlled deflection. It has a tailored bending flexibility and torque transmission which is of major importance in endoscope design. Most instruments have a two-stage bending stiffness, i.e., the distal portion of the insertion tube is more flexible than the proximal portion. The flexibility of each portion of the insertion tube requires extensive clinical testing to ensure that the endoscope handles easily and produces a minimum of patient discomfort.

The colon is a tubular organ which runs from the cecum in the right lower quadrant to the rectum. It is widest in the cecum and ascending colon and gradually narrows as one approaches the rectum. The colon is divided into the following sections:
  a. the cecum;
  b. the ascending colon, which runs cephalad (towards the head) from the cecum to the hepatic flexure;
  c. the transverse colon, which runs from the hepatic flexure in the upper quadrant to the splenic flexure in the left upper quadrant;
  d. the descending colon, which runs caudal (toward the feet) from the splenic flexure to the left lower quadrant;
  e. the sigmoid colon, which runs from the left lower quadrant to the rectosigmoid junction; and
  f. the rectum, which extends down to the anal canal.

The inner layer of circular muscle is present throughout the colon. The outer longitudinal muscle in the wall of the colon is fused into three bands, the teniae coli. These bands start at the base of the appendix and run in the wall of the colon down to the rectum, where they diffuse into the muscular coat. The three teniae cause the colon to have a triangular appearance endoscopically; this is especially prominent in the ascending and transverse colon. The haustra are outpouchings of the colon, separated by folds. In the descending colon the endoscopic appearance is often tubular.

Most experienced colonoscopists use similar endoscopic techniques. Air is introduced to inflate the colon, but as little as possible to prevent overdistension. The pushing pressure on the endoscope is gentle to avoid stretching the colonic wall or mesentery (the connective tissue that holds the colon like a fan) which can cause pain, a vagal episode, or a perforation. The lumen is kept in view at all times; little or none of the examination is performed blindly, because the colonoscopist is pushing a stiff instrument through delicate tissue.

A variety of in and out maneuvers are used to "accordian" the colon on the colonoscope, keeping the colonoscope as free of loops as possible. In the difficult colon, special maneuvers such as the creating of an alpha loop in. the sigmoid colon are used to pass the sharply angulated sigmoid/descending colon junction. This maneuver may require fluoroscopic guidance and training in the technique.

The colonoscope is advanced to the cecum under direct visualization. The detailed examination of the mucosa is usually performed as the colonoscope is slowly removed from the cecum.

To inspect the whole length of the large intestine requires a highly skilled practitioner, which makes the procedure costly. Even still, the procedure can be very painful for the patient, making sedation necessary. This is due to the inherent deficiencies in the "push-to-advance" design.

The small bowel, also known as the small intestine, is a long, coiled organ located in the center of the abdominal cavity. The small bowel is about 6 meters in length and it extends from the stomach and pyloric sphincter to the ileocecal valve, where it empties into the colon, or large intestine.

The small intestine is divided into the following sections:
  a. the duodenum,
  b. the jejunum; and
  c. the ileum.

The walls of the small intestine are generally similar to, albeit somewhat more delicate than, the walls forming other portions of the digestive tract, such as the colon described above. The walls of the small intestine consist of a lining which is smooth in the duodenum, but which has folds and small projections thereafter, whereby to create the greater surface area needed for the enhanced absorption of nutrients.

Although the small intestine is much longer than the large intestine (typically 4-5 times longer), it has a much smaller diameter than the large intestine. On average, the diameter of the small intestine of an adult human measures approximately 2.5 to 3 cm in diameter, whereas the large intestine typically measures about 7.6 cm in diameter.

Due to the significant differences in both the diameters and lengths of the small bowel and the large bowel, traditional endoscopes and the methods used in large bowel applications are not ideal for investigating the small bowel. This is because of the need to gather (or pleat) the small bowel onto the endoscope, which is difficult to accomplish using traditional endoscopes. In addition to the foregoing, and as discussed above, the narrower small bowel also has a very delicate wall lining which is more susceptible to trauma than the lining of the colon.

Current approaches for accessing the small bowel generally utilize balloon devices which are advanced to, and into, the small bowel and then inflated. Once the device is inflated, the device is pulled proximally in order to gather a length of the small bowel onto the device, and then the device is deflated. The device is then advanced further into the small bowel and the process repeated as necessary so as to traverse the entire length of the small bowel. This process is extremely time-consuming for both the physician performing the procedure and the patient undergoing it. Keeping the length of the procedure as short as possible is important since the longer the small bowel tissue is gathered, or "pleated", on the device, the higher the chances for tissue damage or tissue necrosis. Similarly, the longer the procedure, the greater the risk of anesthesia-related complications.

In view of the foregoing, traditional "push-to-advance" endoscopic designs and methods are less than ideal for small bowel applications, and thus there is a need for a novel approach for endoscopically investigating the small bowel.

Summary of Issues with the Prior Art

In summary, there are problems in making present push-in catheters, dilators, and occluders stiff enough for penetration and flexible enough to make the turns without undue risk of trauma to the wall of the passageway when being pushed in;

and once installed, comfortable enough to wear for an extended period of time. The problems with stent encrustation and removal are well known. Self administration is inhibited by all of the short-comings of the prior art. Further injury, infection and discomfort can result from unskilled or improper technique. The problems with colonoscopy have been previously described.

The long history of push-in catheters/dilators and occluders has gradually crystallized into an industry-wide, self-perpetuating, fundamental assumption that catheters are to be mainly pushed through bodily passageways, albeit with some rotational easing. This "fact" is so widely perpetuated and pervasive in the commercially-available products and medical practices as to have stifled original thinking in this art. This, in spite of the well-recorded shortcomings of pain, trauma, risk of rupture, and failed, aborted or incomplete procedures, and the need for skilled practitioners and special equipment for monitoring and safeguarding against the inherent problems.

SUMMARY

For the purposes of this disclosure, including the appended claims, the terms "distal", "distally", and "distal end", as they relate to the devices and methods described herein, refer to the end of the device further from, or in the direction away from, a practitioner who might be applying the device or method to the subject. Stated otherwise, the aforementioned terms refer to the end of the device closer to, or in the direction towards, the subject's interior.

The terms "proximal", "proximally", and "proximal end", as they relate to the devices and methods described herein, refer to the end of the device closer to, or in the direction towards, the practitioner who might be applying the device or method, rather than to the subject.

In accordance with example embodiments of the present invention, an apparatus for accessing a bodily passageway includes: an endoscope including an insertion portion configured to extend into the bodily passageway; a drive tube including a lumen configured to receive the endoscope; a helically-wound thread disposed on an outer wall of the drive tube and configured such that rotation of the drive tube causes the drive tube with the endoscope to move along the passageway; a flexible drive shaft configured to transfer rotary motion generated by a power supply; and a rotatable drive collar disposed on the endoscope and configured to rotate the drive tube relative to the endoscope, the rotatable drive collar including a stator, a rotor rotatable over the stator and detachably coupled to the drive tube, a rotary gear configured to transfer the rotary motion from the flexible drive shaft to the rotor to rotate the drive tube, and a watertight seal disposed between the stator and the rotor.

The seal may include annularly-shaped rubber rings disposed on respective distal and proximal sides of the rotary gear to seal a gap between an inner surface of the rotor and an outer surface of the stator.

The apparatus may further include a joint provided on the drive tube and the rotor to couple a proximal edge of the drive tube and a distal edge of the rotor in an axial direction of the endoscope.

The rotatable drive collar may include a stabilizer disposed on the inner surface of the rotor, and the apparatus may further include a holder disposed on the stator and configured to hold the stabilizing member to restrain the axial and radial movement of the rotor.

The stator may further include a stopper detachably and rotatably coupled to the drive tube to restrain the axial movement of the drive tube.

The watertight seal may include an elastic tubular member that covers an entire outer circumference of the rotary gear, and each end of the elastic tubular member is fixed watertightly to the outer surface of the stator.

The apparatus may further include a boot disposed on a proximal side of the rotatable drive collar and covering the insertion portion of the endoscope around a circumference of the rotatable drive collar.

The boot may be configured to resist bending of the insertion portion about the rotatable drive collar.

The rotor may be configured to rotate with respect to the boot.

The boot may contact the rotor to form a barrier around the circumference of the rotatable drive collar.

The contact between the boot and the rotor may form a watertight seal around the circumference of the rotatable drive collar.

In accordance with example embodiments of the present invention, an apparatus for accessing a bodily passageway includes: an endoscope including a rotatable drive collar rotatable relative to a housing of the endoscope, a handle disposed at a proximal end portion of the endoscope, and a channel extending from the handle to the rotatable drive collar; a drive tube including a lumen configured to receive the endoscope and mounted to the rotatable drive collar; a helically-wound thread disposed on an outer wall of the drive tube and configured such that rotation of the drive tube causes the drive tube with the endoscope to move along the passageway; and a detachable motor unit comprising a flexible drive shaft, a transmission gear on a distal end portion of the flexible drive shaft, and a motor configured to rotate the flexible drive shaft, wherein the flexible drive shaft is inserted into the channel of the endoscope and the transmission gear is positioned to engage with the rotatable drive collar so that the transmission gear is arranged to transfer the rotary motion from the flexible drive shaft to the rotatable drive collar to rotate the drive tube with the rotatable drive collar.

Objects of the present invention include providing and employing screw-based means for rotational advancement and anchoring of catheters, probes, occluders, stents, and dilators into genitourinary and gastrointestinal passageways such as the urethra, ureter, esophagus and fallopian tube, and for the emplacement of suprapubic catheters for draining genitourinary organs such as the bladder, whereby the subject device is applied through a natural body orifice or surgically created opening and is drawn through the passage by the longitudinal pull of a helix on the walls of the passage or organ as the device is rotated. Objects of the present invention also include gathering, or "pleating", bodily passageways (such as the small bowel) on to the screw-based means so as to facilitate movement of the screw-based means relative to the bodily passageways.

This technology is a radical departure from the 4000 year old traditional "push-to-advance" methodology previously discussed.

Indwelling and Intermittent Catheters

In accordance with example embodiments of the present invention, flexible, thin-wall indwelling and intermittent catheters and related devices and delivery stylets, made possible by this rotate-to-advance form of emplacement, are less traumatic and easier for the medical practitioner or patient to use. The catheter of the present invention eliminates the problems of conventional devices by using helix or rotational technology that provides controlled insertion and flexibility to negotiate the urethra. The helix design accomplishes a pre-dilatation of the passageway at a steady rate that relaxes the sphincter and lessens or prevents spasm. Once placed, the device is anchored by the radial displacement and close pitch of the helix, preventing longitudinal migration due to body movement or fluid flow.

In accordance with example embodiments of the present invention, the helix is located on the shaft under a Foley-type balloon and disappears when the balloon is inflated. The flexible, reinforced shaft need be only about half the wall thickness of conventional Foley catheters, which means a smaller outer diameter (OD) catheter can be used. The helix advances the shaft and dilates the urethra as the catheter is inserted. Once the bladder is reached, the balloon is inflated with sterile water, and the helix is engulfed by the balloon. The process is then reversed to remove the catheter. This technology fosters reduced costs for patent care, improved clinical outcomes and enhanced patient quality of life.

Continence Catheter with Valve

In accordance with example embodiments of the present invention, a continence catheter, indicated for bladder outlet obstructions, is intended for BPH patients who are not able to, or choose not to, undergo TURF. Such embodiments of the present invention allow, e.g., the urethra in the area of the prostate to remain open. At the proximal (external) end of the catheter there may be a flow valve which may be depressed or otherwise opened to empty the bladder. The catheter may be produced as a sterile, single-use, and/or disposable item that can be used, e.g., once, and replaced as needed.

The same example embodiments of the catheter of the present invention may provide a female stress urinary incontinence (UI) sufferer with lifestyle benefits that greatly outperform absorbent products intended to manage this condition.

The patient may simply insert the catheter into the urethral opening and rotate the shaft to advance the catheter into the bladder. This may be done in the morning in the convenience of home. When the user needs to urinate, the valve end of the flexible shaft may be exposed through the clothing and the valve opened to empty the bladder. Since the device is not removed and reinserted after each voiding, the risk of infection is reduced. At the end of the day, the catheter is easily removed and disposed of.

Intraurethral Valved Catheter

In accordance with example embodiments of the present invention, the male and/or female intraurethral valved catheter of the present invention is indicated for bladder control. These embodiments of the present invention may allow the flow of urine to be controlled by a valve mechanism that is within the catheter. This valve may be actuated directly by insertion of a tool such as a stylet, or remotely by using a magnetic field device.

The intraurethral device may reduce the potential for infection by eliminating the external tubing which can be an entry path for bacterial contamination. These catheters are typically 3.5 to 6.5 centimeters in length, depending on the anatomy, and have the helical element of the present invention on the outer diameter of the body. The thread height of the helix may vary over its length, as an aid to the advancement and retention characteristics of the device. The sidewall of the catheter may be reinforced to resist collapsing due to contraction pressure. This catheter may be inserted in the urethra under fluoroscopy, using a detachable flexible stylet which keys into the proximal end of the catheter in a non-rotational fitment, and may be inserted in an outpatient procedure using topical anesthesia.

Stents

In accordance with example embodiments of the present invention, a stent, indicated for bladder outlet obstructions, keeps the urethra open in the area of the stricture. The stent body may be between 3.5 cm and 6.5 cm in length, depending on the anatomy, and has a helical element on the outer diameter of the body to advance and retain the stent. The sidewall of the stent may have a reinforcement means to prevent collapsing due to prostate pressure. The stent may be inserted in the urethra under fluoroscopy, e.g., using a detachable flexible stylet which keys into the proximal end of the stent body, and may be inserted in an outpatient procedure, e.g., using topical anesthesia.

The stents in accordance with example embodiments of the present invention are not susceptible to being incorporated by the urethral mucosa in a manner preventing rotation, thereby permitting a lengthy period of emplacement and subsequent removal by the same rotational technique. The stents may also have a sufficiently large internal diameter, or lumen, to permit cystoscopies, thereby allowing examination of the bladder without removing the stent.

Dilators and Occluders

In accordance with example embodiments of the present invention, helically-adapted dilators and occluders are likewise rotatingly advanced and retracted; the helical element performing a dilatory function to some degree. Dilators of respectively larger diameters may be used to achieve a gradually more pronounced effect.

The rotational advancement means may be combined with the push-to-advance methodology in any of these devices. In a dilator, for example, a helically-equipped leader shaft extending distally of the bulbous portion of the device rotatingly advances the device up to the point that the helix passes out of the interior end of the passage; the remainder of the leader shaft then providing a guidewire that leads the bulb through the remainder of the passageway when the dilator is pushed from the proximal end.

Suprapubic Catheters

In accordance with example embodiments of the present invention, a suprapubic catheter, used in a classic transabdominal puncture for the drainage of the bladder or other genitourinary organs, permits the helix on the distal end of the catheter to be emplaced in the wall of the organ far enough so that the helical vane extends from both sides of the organ wall, so that the longitudinal sliding motion of the catheter into and out of the organ is inhibited by the helical vane. This reduces a source of irritation and associated complications at the organ wall entry point.

The helically-adapted suprapubic catheter may be placed in the organ using ultrasound or fluoroscopy to visualize placement, by rotatingly advancing the catheter over a guidewire leading to the organ; the guidewire having been installed through a tubular access created by using a cannula and trocar to reach the organ, the trocar and the cannula having been successively removed.

General Construction

Any embodiment of the present invention may be radiopaque, or have radiopaque features, markers or other components, permitting the use of fluoroscopy to monitor emplacement or removal of the device, or even the rotational orientation and rotational movement of the device.

The thread element may be solid, hollow, or fluid-filled. It may taper in height at various locations to optimize advancement and anchoring. Embodiments or elements of the present invention. may be fabricated, molded, wound, extruded or otherwise constructed of non-toxic, non-corrosive materials, or combinations of materials, e.g., a composite construction, that are otherwise tolerant of bodily fluids and/or durable when implanted in vivo. Such materials may include, but are not limited to, polyurethane, medical grade stainless steel, silicone, bicarbon, polytetrafluoroethylene, tantalum, titanium, or nickel-titanium alloy. Conversely, materials may be specifically chosen to be bioabsorable so as to obviate the need for removal.

The devices in accordance with example embodiments of the present invention may be enhanced with one or a combination of the following coatings: a water-based hydrophilic; antibacterial coatings such as nitrofurazone; bateriostatic coatings such as silver; or other mediations to further enhance their clinical performance.

Threaded Camera Introducer

In accordance with example embodiments of the present invention, the threaded camera introducer system, briefly stated, presents a mechanism for the introduction of visualization sensors and other implements into and through the full length of a bodily passageway, e.g., the colon (for purposes of illustration, the threaded camera introducer system will sometimes hereinafter be discussed in the context of, and with specific reference being made to, the colon; however, it should be appreciated that the threaded camera introducer system also has application for use in other bodily passageways, e.g., the small bowel, and no limitation of use is intended to be inferred). The fundamental structure of the introducer, consistent with the rotate-to-advance structure and methodology of the present invention, is a large, soft, flexible worm-like tubular device with a helix of soft, pliant threads which translate rotational force at the proximal end to a pulling action on the colon wall.

The hollow core or central lumen connects the distal and proximal ends of the tube. A camera head or other visual sensor can be introduced into the device and arranged to "see" forward from the center of the bulbous tip on the distal end. Light bundles or wires connected to the camera pass through the central lumen and out the proximal end of the device to an appropriate control and viewing apparatus.

The distal end of the device is gently urged into the rectum sufficiently far to engage the helix. The device is rotated from just outside the point of entry, to slowly advance into and through the entire length of the colon to the cecum. The helical threads pull the device gently along the interior colon wall; the flexibility of the device allows it to easily negotiate the major turns of the colon. The larger threads at the distal end provide the greatest grip or pull, the smaller threads closer to the proximal end contributing a lesser degree of grip or pull. The device is removed using the same method in reverse.

As illustrated in the figures, the light bundles or cables may be encased in a flexible torque tube or assembly which provides or contributes to the torsional strength necessary to rotatingly advance and withdraw the device.

The interior wall of the main tubular device or introducer may be configured to contain the torque tube or vertebra in a non-rotational manner, such that torque applied at any place on the exterior wall of the introducer is transmitted to the torque tube and hence over the full length of the device.

Various embodiments and enhancements are possible, all within the scope of the present invention; for example:

1. The helical thread or spiral extending the length of the device may be used for auxiliary purposes, including to:
   a) carry fluids into the colon/passage;
   b) provide vacuum to the passageway itself, or vacuum within the device to facilitate the advancement of the camera or endoscope into the device;
   c) convey light bundles or electrical wires for specific purposes, and/or;
   d) provide depth markers to assist the practitioner in determining the general position of the device within the body;
2. the spiral may also be inflated with a fluid during entry to obtain full thread form and rotationally grip or fix the catheter to the camera element, and then deflated to permit non-rotational removal by pulling the device through the colon;
3. the video screen, or the image on the screen as seen through the rotating camera introducer as it advances, may be electronically processed to hold the image in a non-rotating, stationary manner for the benefit of the person administering the procedure;
4. the distal portion of the device may be relatively more flexible to enhance trackability along the path of the colon/passageway;
5. the device may have sufficient torque transmission capability from the proximal to the distal end so the distal portion of the device can be thus rotated at full length in the colon without interior support;
6. the distal tip or zone may have a sufficient thread height to grip the colon wall and provide the primary "pulling power" to advance the device into the body and negotiate the turns, while the somewhat lower thread height along the remainder of the device is adequate to support rotational advancement without drag and avoid bunching or gathering of the colon wall;
7. there are at least three methods of containing and controlling this 160 cm long instrument to ensure it remains within the operating field:
   a) a dispensing device as shown in FIG. 34;
   b) a straight tubular component; or
   c) held by an assistant;
8. material of construction:
   a) the main body may be produced from polyvinylchloride (PVC) plastic and may be reinforced with wire or fabric;
   b) the helix may be made of PVC and may be reinforced with wire or otherwise;
   c) a distal end window may be a fiat, optically clear plastic lens made from PVC, polycarbonate, or acrylic plastic;
9. alternative uses:
   a) variations on the introducer device within the scope of the present invention include, e.g., full length tubes, or short sections analogous to urethral stents, being emplaced in the colon by the rotational structures and techniques of the present invention for temporary purposes such as to aid in the repair of a damaged colon or a related abdominal injury or condition, by providing a supplemental lining and/or form to the colon or to a section of the colon;

10. camera with torque control umbilicus:
   a) the camera body which houses both the camera and the light source may be made of stainless steel or molded with a dimensionally stable plastic such as polycarbonate;
   b) the vertebrae which makes up the torque control umbilicus may be made of a high strength thermoplastic or a metal such as stainless steel or beryllium copper.

By means of example embodiments of the present invention, the entire colon may be examined without the need for a conventional colonoscope or endoscope, and without the attendant expertise, pain, medication, post-procedure recovery time, and cost. The means and method of the present invention require less training and have far greater likelihood of reaching the cecum (far end of the colon) than conventional tools and procedures.

Other body cavities and passageways may be similarly examined.

Among other things, the threaded camera introducer system may be used to gather, or "pleat", bodily passageways (such as the small bowel) on to the threaded camera introducer system so as to facilitate movement of the threaded camera introducer system relative to the bodily passageway, whereby to facilitate visualization and/or treatment procedures.

The camera introducer catheter may be used, for example, in the following four different modes:

1. as an "introducer", it includes the following characteristics and benefits:
   a) it conveys a camera assembly along the entire colon to screen patients for polyps, lesions, cancer sights and other maladies;
   b) the entire colon can be examined without the need for a conventional colonoscope/endoscope;
   c) a total examination of the colon can be successfully performed with significantly less manipulation technique, pain, medication and post procedure recovery time;
   d) it requires less training and has greater success in reaching the cecum;
   e) as a single-use disposable device, it allows the expensive camera with its torque controlled umbilicus to be used repeatedly without danger of sequential infections;
   f) the procedure is less expensive when compared to the cost of cleaning and repairing conventional endoscopes and amortizing the cost of a costly video processing unit;
   g) the procedure can be successfully performed by less-specialized, less-expensive individuals; and
   h) the "introducer" is supplied sterilized and ready for use;

2. as a more "conventional style endoscope"—by adapting a conventional endoscope to the structure and method of the present invention, the benefits of the present invention are coupled with the following conventional functions:
   a) tip articulation;
   b) air and water delivery;
   c) suction of fluids;
   d) illumination of passages;
   e) imaging capability;
   f) drug delivery; and
   g) accessories (e.g., working tools).

3. as a "hybrid catheter" having some of the functions and features of the more "conventional style endoscope" and/or the "introducer" built into the device for procedure-specific applications; also, it could be used in conjunction with, or independent of, conventional endoscopic devices and accessories; and 4. as a "transporter" or "introducer" to deliver a conventional endoscope to any location of the colon or other passageway—this may occur by:
   a) providing a fluid-tight envelope for the endoscope; and
   b) providing a means for the endoscope to exit the distal end of the "introducer" to perform diagnostic/therapeutic procedures normally done with the endoscope.

Thus, in some example embodiments of the present invention, a conventional endoscope may be positioned within an introducer having a generally tubular construction with a helical thread on the exterior, whereby rotation of the introducer will cause the introducer, and hence the endoscope, to be moved longitudinally within a bodily passageway. And in accordance with some preferred embodiments of the present invention, the endoscope may be coupled to the introducer with a rotary coupling, such that the endoscope may remain free from rotation while the introducer is rotated, whereby to stabilize the endoscope image while the introducer is rotated.

And in accordance with other example embodiments of the present invention, a conventional endoscope may be modified so as to provide helical threads along some or all of the exterior sidewall of the endoscope, such that upon rotation of the endoscope, the helical threads will move the endoscope longitudinally within a passageway.

Powered Drive

It should be appreciated that the system in accordance with example embodiments of the present invention may be rotated manually (e.g., by the surgeon rotating the catheter by hand) and/or the system may be power driven. In some preferred embodiments of the present invention, a powered drive may be used to rotate the catheter so as to allow an easier and more precise advancement of the catheter into the bodily passageway or retraction of the catheter from the bodily passageway.

Lavage System

In accordance with example embodiments of the present invention, a lavage system may be provided for clearing away debris from the front of the catheter. In many situations, the bodily passageway receiving the catheter may be obscured with debris, and it may be helpful to have a clear view of the anatomy when advancing an endoscope through the bodily passageway. A lavage system may be provided to flush debris from the cavity passageway with fluid during the insertion of the endoscope. By way of example, the lavage system may be used to break up and remove fecal matter from the colon, thereby enabling a clearer view of the anatomy when the catheter is being advanced through the colon.

Some Preferred Forms of the Present Invention

In accordance with example embodiments of the present invention, there is provided a method for visualizing the interior of a bodily passageway at a remote location, the method comprising the steps of:

providing a visualization system for deployment in the bodily passageway, the visualization system comprising:

an endoscope comprising a rotatable drive collar configured for rotation relative to the endoscope;

a disposable drive tube comprising an elongated tube having a deformable helical thread disposed on an exterior surface of the elongated tube, the elongated tube being configured for coaxial disposition about the endoscope; and a mount for releasably securing the disposable drive tube to the rotatable drive collar of the endoscope;

wherein the helical thread has a sufficient structural integrity, and a sufficient surface profile, such that when the disposable drive tube is disposed in the bodily passageway so that the helical thread engages the interior side wall of the bodily passageway, rotation of the disposable drive tube will induce a relative movement between the disposable drive tube and the side wall of the bodily passageway;

mounting the disposable drive tube coaxially about the endoscope so that the disposable drive tube is secured to the rotatable drive collar of the endoscope;

inserting the visualization system into the bodily passageway at a location remote from the site which is to be visualized, with the deformable helical thread being in a reduced profile configuration;

transforming the deformable helical thread into an expanded profile configuration;

rotating the disposable drive tube so as to bring together the site which is to be visualized and the visualization apparatus; and using the visualization apparatus to visualize the interior of the bodily passageway.

In another preferred form of the invention, there is provided a method for visualizing the interior of a bodily passageway at a remote location, the method comprising the steps of:

providing a visualization system for deployment in the bodily passageway, the visualization system comprising:

an endoscope comprising a rotatable drive collar configured for rotation relative to the endoscope;

a disposable drive tube comprising an elongated tube having a deformable helical thread disposed on an exterior surface of the elongated tube, the elongated tube being configured for coaxial disposition about the endoscope; and a mount for releasably securing the disposable drive tube to the rotatable drive collar of the endoscope;

wherein the deformable helical thread has a sufficient structural integrity, and a sufficient surface profile, such that when the disposable drive tube is disposed in the bodily passageway so that the deformable helical thread engages the interior side wall of the bodily passageway, rotation of the disposable drive tube will induce a relative movement between the disposable drive tube and the side wall of the bodily passageway;

mounting the disposable drive tube coaxially about the endoscope so that the disposable drive tube is secured to the rotatable drive collar of the endoscope;

inserting the visualization system into the bodily passageway at a location remote from the site which is to be visualized;

rotating the disposable drive tube so as to bring together the site which is to be visualized and the visualization apparatus;

using the visualization apparatus to visualize the interior of the bodily passageway;

The method may further include:

transforming the deformable helical thread to a reduced profile configuration; and withdrawing the visualization system from the bodily passageway.

In accordance with example embodiments of the present invention, there is provided apparatus for visualizing tissue, the apparatus comprising:

an endoscope comprising a rotatable drive collar configured for rotation relative to the endoscope;

a disposable drive tube comprising an elongated tube having a helical thread disposed on an exterior surface of the elongated tube, the elongated tube being configured for coaxial disposition about the endoscope; and a mount for releasably securing the disposable drive tube to the rotatable drive collar of the endoscope;

wherein (i) the deformable helical thread is transformable between a reduced profile configuration and an expanded profile configuration, and (ii) when in its expanded profile configuration, the deformable helical thread has a sufficient structural integrity, and a sufficient surface profile, such that when the disposable drive tube is disposed in the bodily passageway so that the deformable helical thread engages the interior side wall of the bodily passageway, rotation of the disposable drive tube will induce a relative movement between the disposable drive tube and the side wall of the bodily passageway; and wherein the disposable drive tube is mounted coaxially about the endoscope so that the disposable drive tube is secured to the rotatable drive collar of the endoscope.

In accordance with example embodiments of the present invention, there is provided an apparatus for inducing relative movement between an endoscope and the side wall of a bodily passageway within which the endoscope is disposed, wherein the endoscope comprises a rotatable drive collar configured for rotation relative to the endoscope, the apparatus comprising:

a disposable drive tube comprising an elongated tube having a deformable helical thread disposed on an exterior surface of the elongated tube, the elongated tube being configured for coaxial disposition about the endoscope; and means for releasably securing the disposable drive tube to the rotatable drive collar of the endoscope;

wherein (i) the deformable helical thread is transformable between a reduced profile configuration and an expanded profile configuration, and (ii) when in its expanded profile configuration, the deformable helical thread has a sufficient structural integrity, and a sufficient surface profile, such that when the disposable drive tube is disposed in the bodily passageway so that the deformable helical thread engages the interior side wall of the bodily passageway, rotation of the disposable drive tube will induce a relative movement between the disposable drive tube and the side wall of the bodily passageway; and wherein the disposable drive tube is mounted coaxially about the endoscope so that the disposable drive tube is secured to the rotatable drive collar of the endoscope.

Still other objects, features and advantages of the present invention will become readily apparent to those skilled in this art from the following detailed description, wherein there are shown and described preferred and other embodiments of the present invention by way of illustration of the best mode contemplated for carrying out the present invention. As will be realized, the present invention is capable of other and different embodiments, and its several details are capable of modifications in various obvious respects, all without departing from the present invention. In this regard, although the present invention is been described with reference to particular examples and exemplary embodiments, it should be understood that the description is in no manner limiting. Moreover, the features described herein may be used in any combination.

BRIEF DESCRIPTION OF THE DRAWINGS

FIG. 5 is a perspective view of a threaded catheter for a female;

FIG. 6 is a cross-sectional view of the threaded portion of the catheter of FIG. 5;

FIG. 7 is a perspective view of a threaded catheter and a flexible shaft stylet with which it is installed;

FIG. 30 is a front perspective diagram of a threaded camera introducer catheter advanced into the transverse colon area;

FIG. 31A is a partial side view of the distal end of the catheter of FIG. 30, showing the larger thread height of the thread in the distal area of the catheter's length;

FIG. 31B is a partial side view of the mid-section of the catheter of FIG. 30, showing the reduced thread height of the thread in other than the distal area of the catheter's length;

FIGS. 39A-39D are schematic views showing another construction for a camera introducer with rotary coupling;

FIGS. 41-43 are schematic views of an access device formed in accordance with the present invention.

FIGS. 63-74 show a camera introducer system comprising a powered helical drive;

FIG. 75 is a schematic view showing a novel visualization system formed in accordance with the present invention;

FIG. 78 is an enlarged view of a portion of the endoscope shown in FIG. 77;

FIG. 79 is an enlarged sectional view of a portion of the endoscope shown in FIG. 77;

FIG. 80 is another enlarged sectional view of a portion of the endoscope shown in FIG. 77;

FIG. 81 is a view taken along line 81-81 of FIG. 80;

FIG. 82 is an enlarged view of a portion of the structure shown in FIG. 81;

FIG. 89 is a partial view of the drive collar of FIG. 88.

DETAILED DESCRIPTION

To those skilled in the art, the present invention admits of many variations and appellations in apparatus and methodology. By way of example, there is provided, in accordance with the present invention, a rotate-to-advance structure and methodology applicable to a range of medical devices that have heretofore relied entirely or substantially on a push-to-advance technique for penetration of bodily passages. Such devices include catheters, dilators, and occluders for mammalian genitourinary or gastrointestinal passages such as the urethra or ureter for the usual purposes associated with such devices where no incising or rupture of passage walls or membranes is intended.

Catheters

Figure 1:
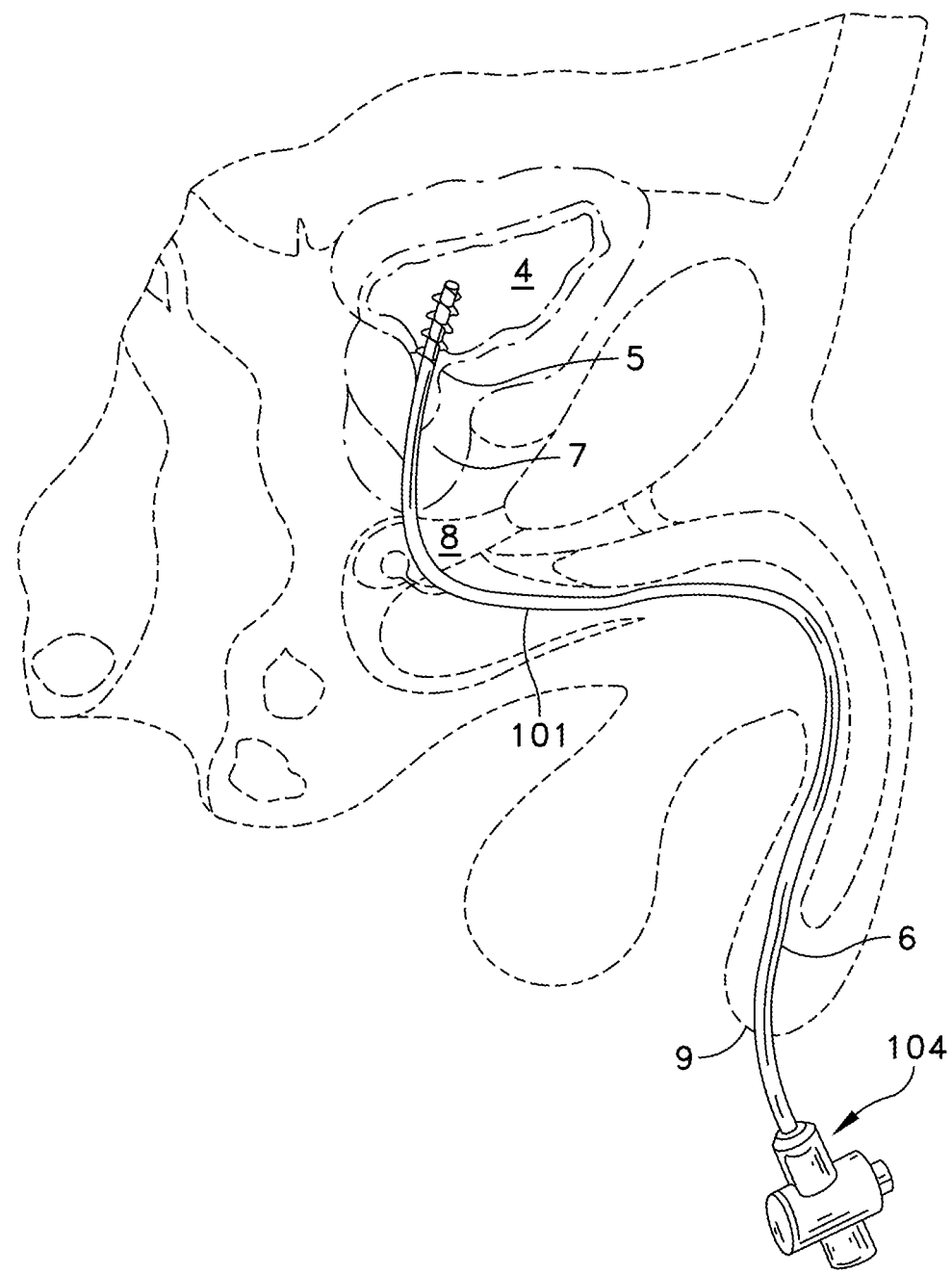
FIG. 1 is an illustration of the lower abdominal anatomy of a male subject, with the threaded portion of the catheter of FIG. 2 extending into the bladder.
Figure 2:
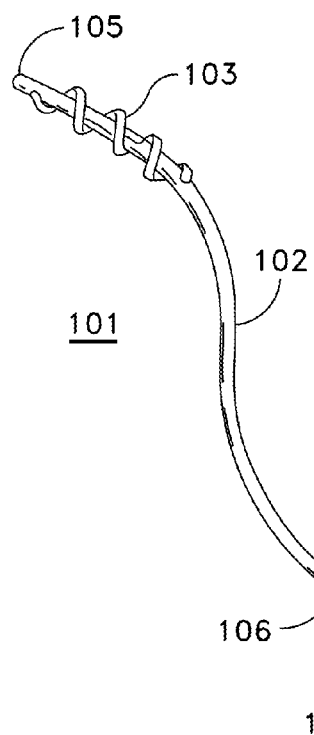
FIG. 2 is a perspective view of a threaded catheter for a male.
Figure 3:
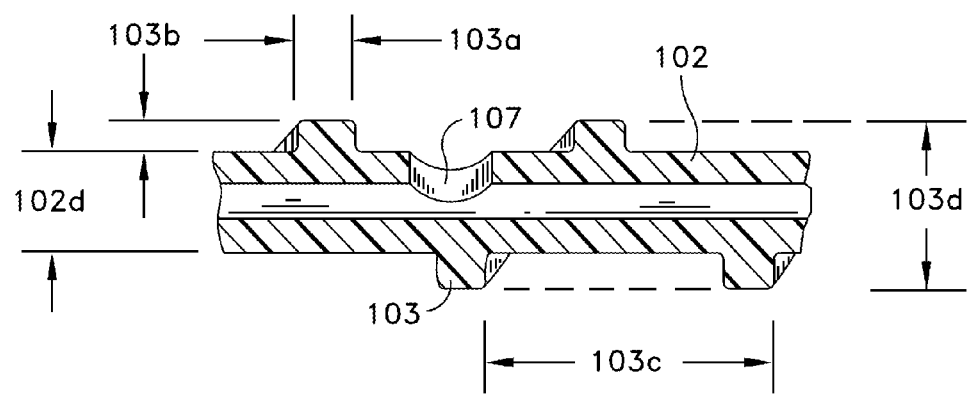
FIG. 3 is a cross-sectional view of the threaded portion of the catheter of FIG. 2.

Referring now to FIGS. 1, 2 and 3, a threaded catheter 101 for males is made up of a tube 102 with an external thread 103, attachable to a flow control device 104. Tube 102 is extruded from a polyurethane material, has an inside diameter of 0.06 inches, an outside diameter 103d of 0.125 inches, and is approximately 13 inches long. The durometer, as measured on the smooth, outside wall of the tube, is 85 Shore A. Distal end 105 is closed off, with its tip rounded to a uniform radius of about 0.06 inches. Proximal end 106 of tube 102 is cut off square and attached to flow control device 104. Tube 102 is sufficiently strong such that when the majority of its length is contained within the urethra, it will withstand and transmit torque, as applied by finger force at the lower end of the tube external of the urethra, to the thread.

Referring to FIGS. 2 and 3, external thread 103 is formed from a strip of polyurethane material with a rectangular cross-section of width 103a, 0.05 inches, and height 103b, 0.032 inches, and continuously attached over its length to tube 102, starting 0.2 inches from distal end 105 and extending four complete turns around tube 102 in a clockwise direction towards proximal end 106 at a uniform pitch 103c of 0.25 inches, resulting in a four-turn thread or helix about one inch long.

It is readily apparent from the dimensions of FIGS. 2 and 3 that the thread height 103b of catheter 101 is greater than twenty percent (20%) of the 103d thread diameter. This relative height is desirable to expand and penetrate the longitudinal folds of the urethra to a sufficient depth to achieve a useful grip by the thread.

The diameter of the helix formed by thread 103 of catheter 101 is referred to as thread diameter 103d, and is equal to two thread heights 103b plus the outside diameter 102d of catheter tube 102 or, in this case, 2 times 0.032 inches plus 0.125 inches, or approximately 0.19 inches. The circumference C of the helix formed by thread 30 is calculated as Π (pi) times thread diameter 103d or, in this case, 3.14 times 0.19, or approximately 0.6 inches.

$$C = \pi \times \text{thread diameter } 103d$$

The ratio R of thread pitch 103c, 0.25 inches, to the circumference of thread diameter 103d, at 0.6 inches, is much less than 1 to 1, thereby improving the leverage of the screw thread for converting rotation into longitudinal pulling power, as compared to ratios larger than 1/1.

$$R = \frac{\text{thread pitch } 103c}{C}$$

The shoulders of thread 103 have a radius of 0.015 inches. In small quantities, thread 103 may be attached to tube 102 by wicking tetrahydrofuran (THF) solvent under the thread using a fine hollow tube. Catheter 101 may be molded in large quantities with thread 103 being an integral part of the molded structure.

Figure 4:
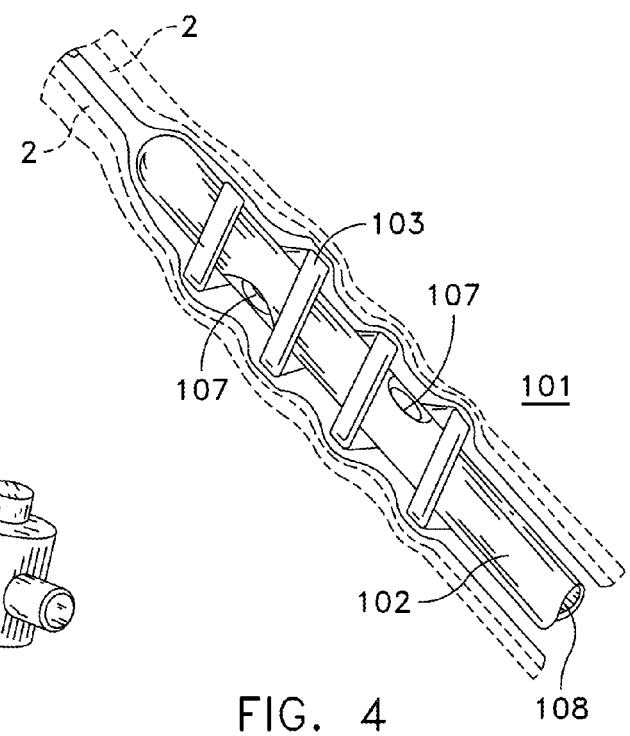
FIG. 4 is an illustration of the threaded end of the catheter of FIG. 1 engaged in the urethra.

Referring to FIG. 4, two drainage ports 107, connecting to lumen 108, are oval in shape, the major axis of the oval being parallel to the axis of tube 102 and about 1.5 times the minor axis, which is about equal to the diameter of the lumen. The two ports are configured 180 degrees apart radially, and spaced longitudinally to fit between the turns of thread 103.

Both ends of thread 103 are tapered from zero to full height in one-half turn of the helix, to facilitate gentle, gradual displacement of urethra wall 2 by thread 103 when catheter 101 is rotated clockwise for advancement into the urethra and counterclockwise for retraction. The difference between thread height 103b and pitch 103c shown in FIG. 3 is sufficient that the urethra wall 2 does not bridge between adjacent turns of thread 103, but rather is only displaced in a manner closely conforming to the cross-section of thread 103, thereby providing the longitudinal grip on urethra wall 2 for advancing and retracting the catheter.

Referring to FIG. 1, catheter 101 is shown in proper position for draining bladder 4, after it has been advanced through the urethra 6 until the helix passes out of the urethra into the bladder.

It is apparent from the anatomy shown in FIG. 1 that thread 103 must be limited in length to be advanced to any point above the sphincter 8, so that the sphincter may contract directly onto the smooth, round, exterior of tube 102, thereby preventing leakage around the tube, and further constraining catheter 101 from migrating or being forced out of the urethra by pressure from urine in the bladder. It is further apparent from the anatomy shown in FIG. 1 that there is a limit to the length of thread 103 on a catheter that can be advanced to a position above the sphincter 8, not more than about six turns within the optimal range of thread pitch, and still fit within the bladder 4 without interference. A limited length of thread 103 also localizes the area of pulling force to the upper end of catheter 101, thereby assuring that the trailing length of the catheter is drawn, not pushed, through the passage.

A useful alternative embodiment of catheter 101 incorporates the recited external thread 103 for rotational advancement, but provides for the central lumen to connect to or terminate in a straight-through or axially-aligned drainage port at the distal tip of the catheter, similar to the most basic conventional catheters. This is likewise useful for drainage and also enables the insertion or passage of guidewires or other devices where specific procedures require it.

Referring next to FIGS. 5 and 6, a threaded catheter 111 for females, similar to catheter 101 for males, is made up of a tube 112 with a thread 113, attachable to a flow control device 114. Tube 112 is extruded from polyurethane material, has an inside diameter of 0.063 inches, an outside diameter 112d of 0.125 inches, and is approximately seven inches long. The durometer, as measured on the smooth, outside wall of the tube, is 85 Shore A. Distal end 115 is closed off, with its tip rounded to a uniform radius of about 0.06 inches. Proximal end 1.16 of tube 112 is cut off square and attached to flow control device 114. Tube 112 is sufficiently strong such that when the majority of its length is contained within the urethra, it will withstand and transmit torque, as applied by finger force at the lower end of the tube external of the urethra, to the thread or helix.

Referring to FIGS. 5 and 6, thread 113 of catheter 111 is formed from a strip of polyurethane material with a rectangular cross-section of width 113a of 0.05 inches and height 113b of 0.10 inches, attached to tube 112 starting 0.2 inches from distal end 115 and extending four turns around tube 112 in a clockwise direction towards proximal end 116 at a uniform pitch 113c of 0.25 inches, resulting in a four-turn thread or helix about one inch long.

It is readily apparent from FIGS. 5 and 6 that the thread height 113b of catheter 111, at 0.10 inches, is much greater than twenty percent (20%) of tube diameter 112d, at 0.125 inches. This relative thread height is desirable in order to expand and penetrate the longitudinal folds of the female urethra sufficiently far to achieve a useful grip by the thread.

Similar to the description of threaded catheter 101, the diameter 113d of the helix formed by thread 113 is equal to two thread heights 113b plus the diameter 112d or, in this case, 2 times 0.10 plus 0.125, or approximately 0.33 inches. The circumference C of the helix formed by thread 113 is calculated as Π (pi) times the thread diameter 113d or, in this case, 3.14 times 0.33, or approximately 1.0 inches. The ratio R of thread pitch 113c, at 0.25 inches, to the circumference C, at 1.0 inches, is again much less than 1 to 1, thereby improving the leverage of the thread for converting rotation into longitudinal pulling power as compared to larger ratios.

The shoulders of thread 113 have a radius of 0.015 inches. Catheter 111 may be constructed or fabricated by the same means as catheter 101.

Referring to FIG. 5, two side drainage ports 117, connecting to lumen 118, are oval in shape, the major axis of the oval being parallel to the axis of tube 112 and about 1.5 times the minor axis, which is about equal to the diameter of the lumen. The two side ports 117 are configured 180 degrees apart radially, and spaced longitudinally to fit between the turns of the thread.

Referring to FIGS. 5 and 6, the ends of thread 113 are tapered from zero to full height in three-quarters turn of the helix, to facilitate gentle, gradual displacement of the urethra wall by the thread when the catheter is rotated clockwise for advancement and counterclockwise for retraction. The difference between width 113a and pitch 113c is sufficient that the urethra wall does not bridge between adjacent turns, but rather is displaced in a manner closely conforming to the profile of the thread, thereby providing the longitudinal grip on the urethra wall for advancing and retracting the catheter, in the same manner as the thread of catheter 101 of FIGS. 2 and 3.

The optimal position for threaded catheter 111 for draining the bladder of a female subject is where it is advanced through the urethra until the thread passes out of the urethra into the bladder, similar to how catheter 101 is illustrated in FIG. 1, but for females.

A detailed method for the self administration of the appropriate respective threaded catheter 101 or 111, or other similar threaded devices, will now be explained.

First, the user assembles materials including a sterile threaded catheter 101 or 111, a container for urine, soap and water, a water soluble lubricant (if the catheter is not pre-lubricated), a mirror (for females), and tissues. The user will then wash the hands and urethral opening with soap and water, squeeze out a small amount of lubricant into clean tissue, dip the distal end tip of the catheter into the lubricant, and manually engage the tip of the catheter into the urethral opening (the mirror may be helpful for females to assist in locating the opening).

The user will then gently push and turn the catheter in, far enough to engage the thread about one full turn with the urethra, and then gently rotate the tube of the catheter in the direction of the thread, preferably clockwise, to advance the catheter into the urethra until urine appears in the tube. The user then pauses to drain the bladder, directing the urine into the container, then resumes rotation of the catheter until it is no longer advanced by the rotation, indicating that the thread of the catheter has passed into the bladder and the catheter is in proper position.

The user then places a flow control device on the proximal end of the catheter and empties the bladder periodically as required. The catheter is removed, when appropriate, using similar precautions for cleanliness and containment, by rotating the catheter in a direction opposite the direction of insertion, presumably counterclockwise.

Figure 8:
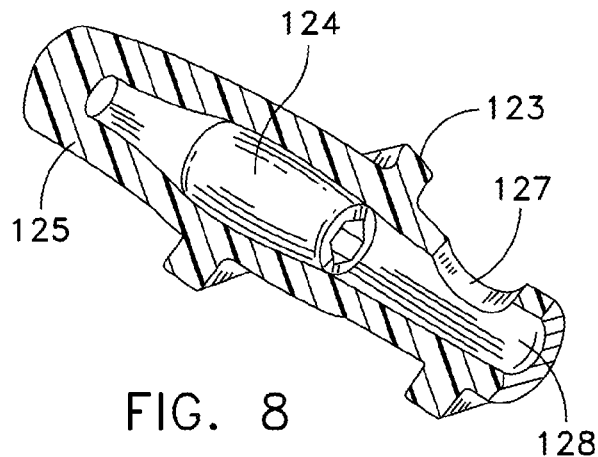
FIG. 8 is a cross-sectional view of the tip of the catheter of FIG. 7, showing the non-rotational fitment that receives the tip of the stylet of FIG. 7.
Figure 9:
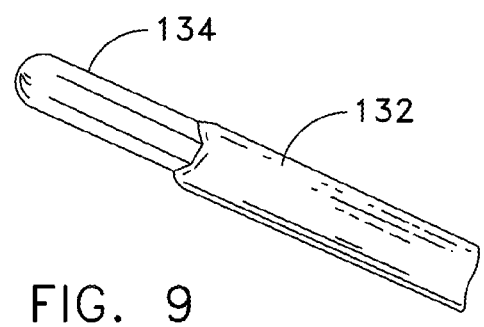
FIG. 9 is a perspective view of the tip of the stylet of FIG. 7 that is insertable into the fitment of FIG. 8.

Referring next to FIGS. 7, 8 and 9, another embodiment of the present invention is illustrated by a catheter 121, which is made up of tube 122 with thread 123 applied in the form of a helix, and utilizing a flexible shaft stylet 131 as an insertion and retraction tool. Stylet 131 has a grip 133 at its proximal end for turning the device. Tube 122 is configured with non-rotational fitment 124 (FIG. 8) near its distal end 125 so that stylet 131 can be inserted through the tube's proximal end 126, passed up through lumen 128 of tube 122, and the tip 134 of stylet 131 engaged with fitment 124 in a manner that allows rotation of grip 133 in one direction to rotate catheter 121 for advancement into the urethra, and in the other direction for retraction.

The flexible shaft 132 of stylet 131 is sufficiently strong such that when it is fully inserted into catheter 121, shaft 132 will withstand and transmit torque, as applied by finger force to knurled knob grip 133 external of the urethra, to the thread 123. Stylet 131 is removed after catheter 121 is installed, and reinserted for retracting the catheter when required.

Fitment 124 is an elongated collar with a multi-faceted interior wall, securely anchored within tube 122, and configured to receive, in a non-rotational relationship, tip 134. Tip 134 is configured with a corresponding elongated, multi-faceted exterior shape and rounded end, to readily enter fitment 124. Stylet tip 134 and fitment 124 can be alternatively configured and connected by various means to provide a non-sliding, as well as non-rotational, connection.

Figure 11:
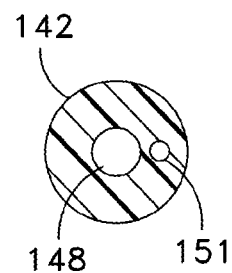
FIG. 11 is a cross-sectional view of the shaft of the catheter of FIG. 10, showing the central drain lumen and the smaller inflation lumen.
Figure 10:
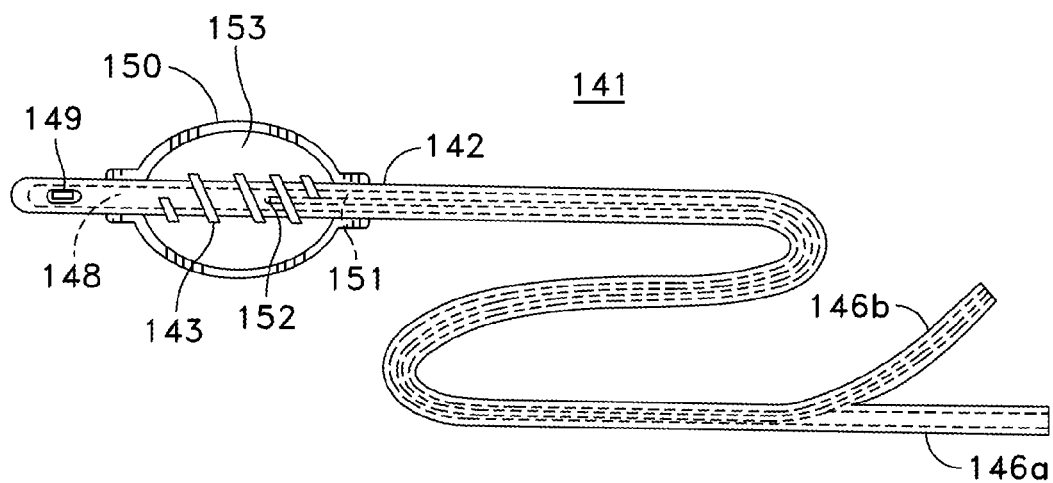
FIG. 10 is a diagrammatic, longitudinal cross-sectional view of a threaded balloon catheter showing the thread element inside the inflated balloon, with lumens shown as dashed lines.
Figure 12:
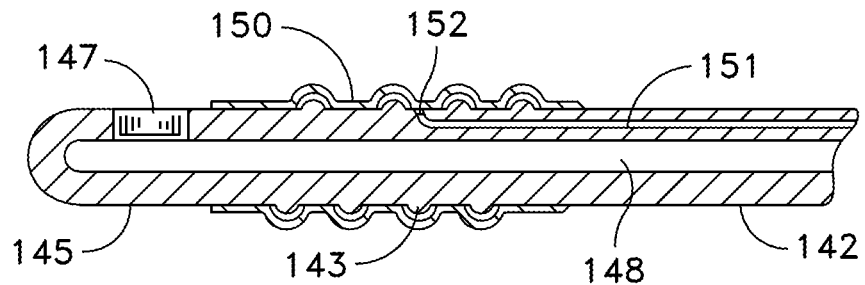
FIG. 12 is a longitudinal cross-sectional view of the distal end of the catheter of FIG. 10, showing the balloon contracted around the helical element.

Referring next to FIGS. 10, 11 and 12, a threaded Foley-type catheter 141 of the present invention is made from polyurethane material. Catheter 141 comprises a flexible tube 142 with an axial drainage lumen 148 running from a drainage port 149 to its proximal end 146a, and a thread 143 applied to its external surface near its distal end 145 in the manner of the threaded catheters previously described. Catheter 141 has a thin-walled inflatable elastic balloon 150 encasing the helical thread 143 and sealed to tube 142 above and below (i.e., distal and proximal to) the thread 143. Drainage port 149 is located above (or distally) from balloon 150. A smaller inflation lumen 151 within tube 142 communicates between inflation port 152 (within the envelope of balloon 150) and the distal end 140 of the catheter. Lumens 148 and 151 are isolated from each other, as indicated by FIGS. 11 and 12.

Balloon 150, when uninflated, is normally contracted tightly about helical element 143 as illustrated in FIG. 12, and may be inflated as in FIG. 10 by injecting fluid through lumen 151 and into the balloon cavity 153. The flexible tube 142 is of sufficient torsional strength to withstand and transmit rotational finger force, applied at the proximal end of tube 142, to thread 143.

Dilators and Occluders

Figure 13:
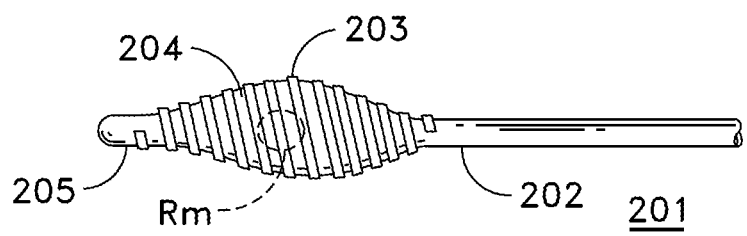
FIG. 13 is a side elevation of a threaded dilator.
Figure 14:
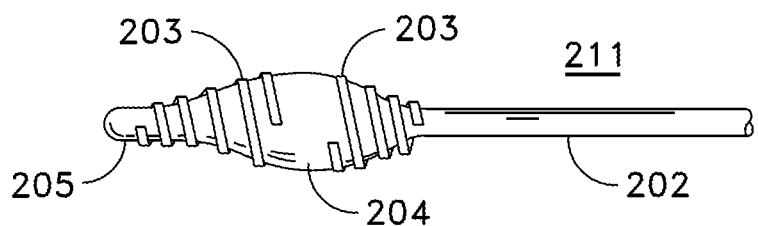
FIG. 14 is a side elevation of a threaded occluder.
Figure 15:
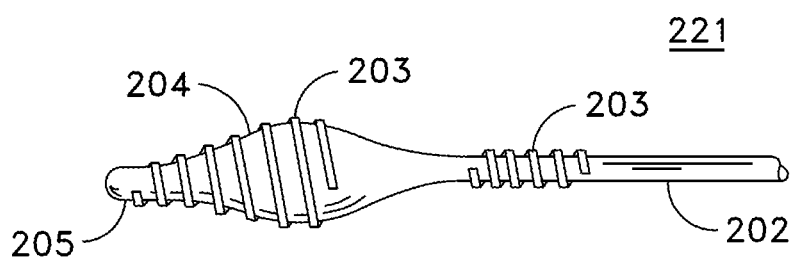
FIG. 15 is a side elevation of another variation of a threaded occluder.

Referring now to FIGS. 13, 14 and 15, a dilator 201 and occluders 211 and 221 are similarly constructed by configuring the upper end 205 of a flexible shaft 202 with a tapered bulb 204 near its distal end, and disposing thereon one or two sections of thread 203. These threads are similar to thread 103 on catheter 101 of FIGS. 2 and 3, wherein the height of the thread is at least twenty percent (20%) of the diameter of the shaft 202, and the ratio of thread pitch to the circumference of the thread diameter at any given point on the bulb or shaft is less than one to one (1/1). The ends of threads 203 are tapered for ease of advancing and retracting, again similar to the threaded catheter of FIGS. 2 and 3.

Dilator 201, of FIG. 13, is configured with multiple turns of thread 203 extending over both ends of tapered bulb 204, and is used to dilate a constricted passage by being rotatingly advanced and retracted through the obstructed area of the passage in the same fashion as the threaded catheters of the present invention.

Occluder 211, of FIG. 14, is configured with two sections of thread 203, leaving the midsection or bulbous portion of tapered bulb 204 smooth and round in order to provide a uniform occluding surface. This occluder is used to plug or constrict a passageway at an interior point, being rotatingly advanced to and refracted from that point in the same fashion as the threaded catheters of the present invention.

Occluder 221, of FIG. 15, is configured with two sections of thread 203, the lower or proximal end thread 203 being disposed on the shaft 202 below the tapered bulb 204, leaving the lower tapered end of bulb 204 smooth and round in order to provide a uniform occluding surface. This occluder is used to plug a passageway at the interior end neck or entrance, being rotatingly advanced until the tapered bulb passes entirely through the passage while the lower thread remains engaged in the passage, and being then rotatingly retracted to seat the tapered bulb against the neck of the passage. The occluder is then rotatingly retracted when appropriate.

Stents and Intraurethral Valve Catheters

Figure 16:
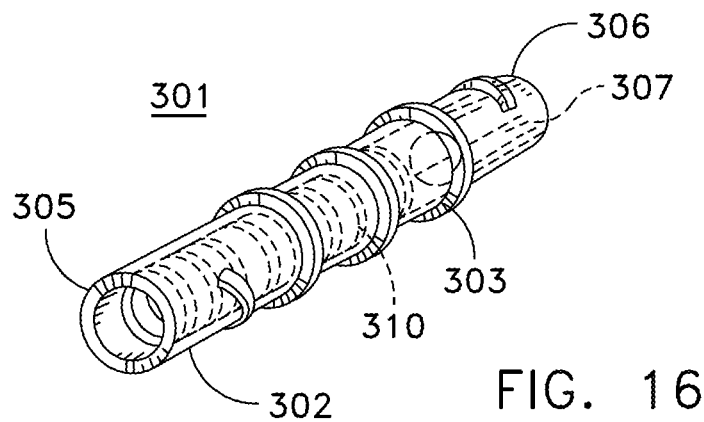
FIG. 16 is a perspective view of a threaded stent, dashed lines showing an internal sidewall reinforcement member and a bushing with a hexagonal drive socket.
Figure 17:
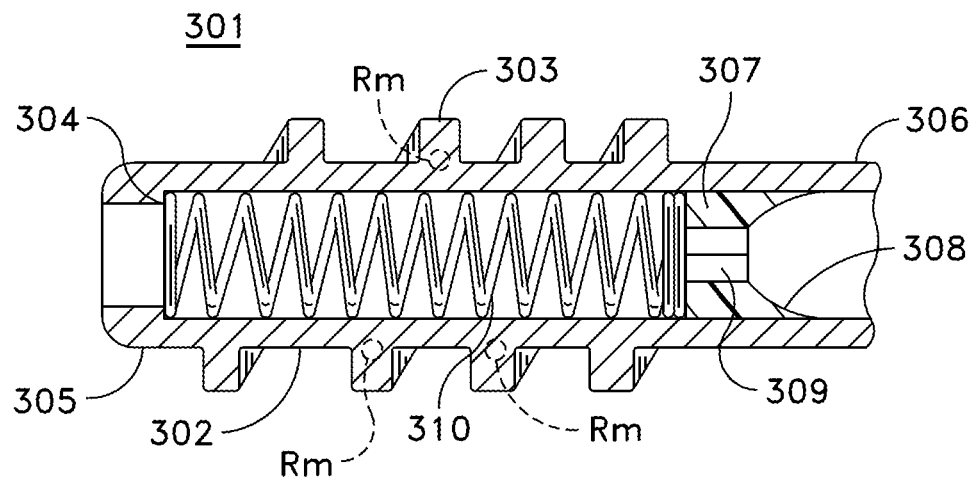
FIG. 17 is a cross-sectional view of the stent of FIG. 16.
Figure 18:
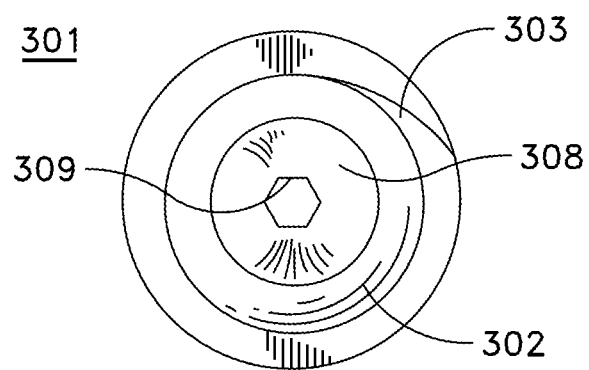
FIG. 18 is a proximal end view of the stent of FIG. 16, with the hexagonal drive socket visible at the center.

Referring now to FIGS. 16-18, a threaded urethral stent 301 made from polyurethane material has a tube 302 with an external thread 303 of uniform pitch. Thread 303 is similar to thread 103 of catheter 101 of FIGS. 2 and 3, wherein the height of the thread is at least twenty percent (20%) of the diameter of the shaft 302, and the ratio of thread pitch to the circumference of the thread diameter is less than one to one (1/1). The ends of thread 303 are tapered for ease of advancing and retracting through a passage. There is an interior shoulder 304 (FIG. 17) at the distal end 305 of the stent, and a bushing 307 (FIG. 17) of relatively harder material disposed proximal to interior shoulder 304. Bushing 307 has a tapered interior wall 308 extending from the bushing's full diameter at one end to a uniform hexagonal aperture 309. Coiled sidewall reinforcement member 310 is secured within stent 301 intermediate bushing 307 and interior shoulder 304. Alternative embodiments may have a section of the thread being tapered to a lesser height or no height, so as to provide a "waist" for gripping by a muscular zone such as the prostate or sphincter. Also, reinforcement member 310 could be configured or molded into the sidewall of tube 302.

Figure 19:
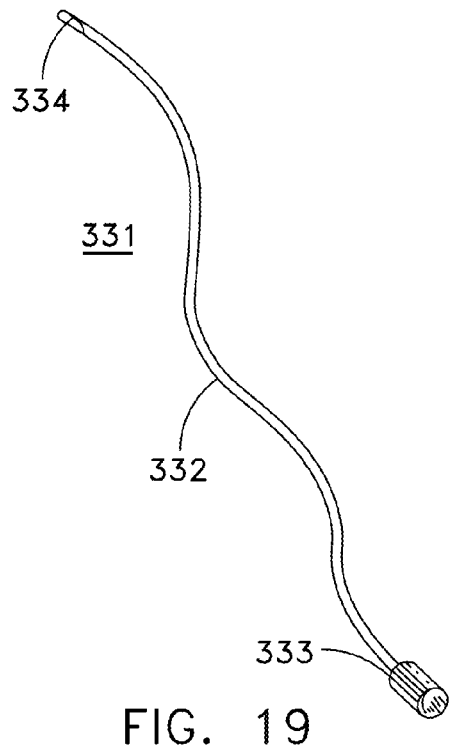
FIG. 19 is a perspective view of a stylet, with a grip on the proximal end and a hexagonal drive tip on the distal end.
Figure 20:
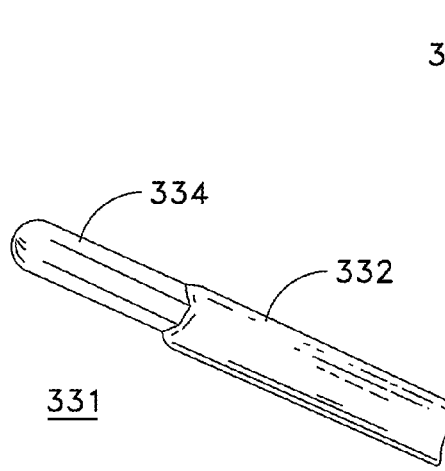
FIG. 20 is a perspective view of the hexagonal drive tip of the stylet of FIG. 19.

Referring now to FIGS. 19 and 20, a stylet 331, similar to the stylet 131 of FIG. 7, has a flexible shaft 332 with a grip 333 at the proximal end for turning, and a hardened hexagonal tip 334 at the distal end which closely fits into aperture 309 of stent 301 in a non-rotational manner for emplacement of the stent by the method of the present invention. The flexible shaft 332 of the stylet is sufficiently strong such that when tip 334 is inserted into aperture 309, the shaft will withstand and transmit torque, as applied by rotational finger force at grip 333, to thread 303.

Figure 21:
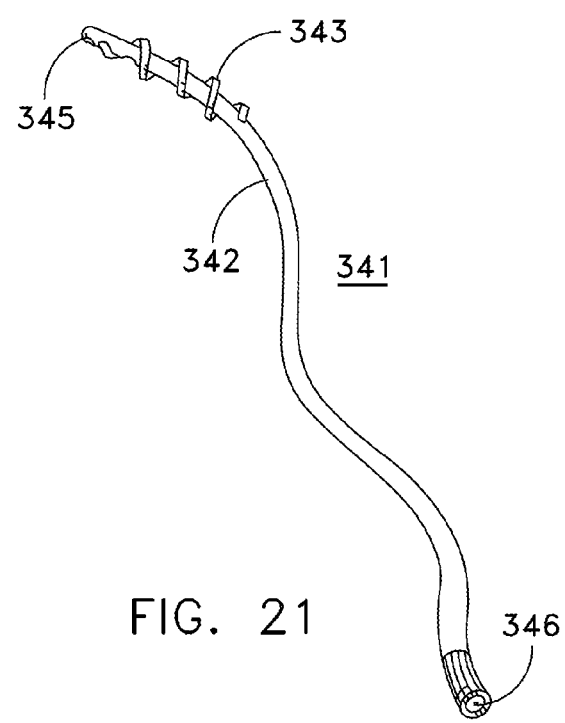
FIG. 21 is a perspective view of a stent-follower with a helical element at the distal end.
Figure 22:
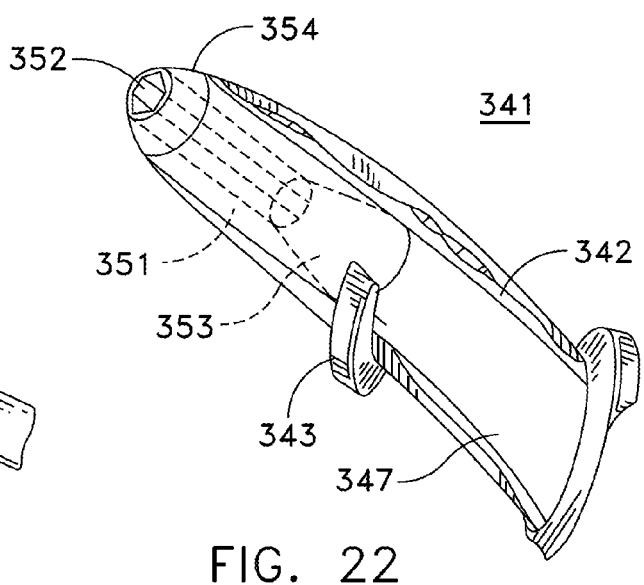
FIG. 22 is an enlarged, cross-sectional view of the distal end of the stent-follower of FIG. 21, showing the hidden portion of the bushing, with the hexagonal drive aperture in dashed lines.

Referring now to FIGS. 21 and 22, a threaded stent-follower 341 has a flexible tube 342, the lumen 347 (FIG. 22) of which is sized to accept the ready insertion of tip 334 and shaft 332 of stylet 331 of FIG. 19. Tube 342 is of sufficient torsional strength to accept and transmit rotational finger force applied at its proximal end 346 to its distal end 345. A thread 343 of uniform pitch, and not more than six turns, is applied to the external surface of tube 342 near distal end 345. Thread 343 preferably conforms to the same twenty percent (20%) "rule" of thread height to tube diameter, and the ratio of thread pitch to thread circumference of less than one to one (1/1), as thread 103 in FIGS. 2 and 3 as described above. The ends of thread 343 are tapered for ease of advancing and refracting.

Referring to FIGS. 17 and 22, bushing 351 (FIG. 22) has a uniform hexagonal aperture 352 which is the same size as aperture 309 in bushing 307 of stent 301, and a tapered interior wail 353 extended from its full diameter at its proximal end to aperture 352. Bushing 351 also has an external tapered tip 354 at its distal end. Bushing 351 is affixed within the distal end 345 of tube 342, with tip 354 protruding, such that the distal end 345 of stent-follower 341 mates with a self centering action with the proximal end of stent 301 when the two devices are brought into contact with approximate axial alignment. When stent-follower 341 and stent 301 are thus mated, tip 334 (FIG. 19) of stylet 331 may be extended through aperture 352 (FIG. 22) and into aperture 309 (FIG. 17), thereby locking stent 301 and stent-follower 341 into a fixed rotational relationship. In this condition, the rotation of the proximal end of stylet 331 and stent-follower 341 causes the concurrent rotation of stent 301, whether to rotatingly advance or retract the stent. Stylet 331 may be withdrawn and stent-follower 341 rotatingly retracted, leaving stent 301 positioned at any useful point within a passageway.

Figure 23:
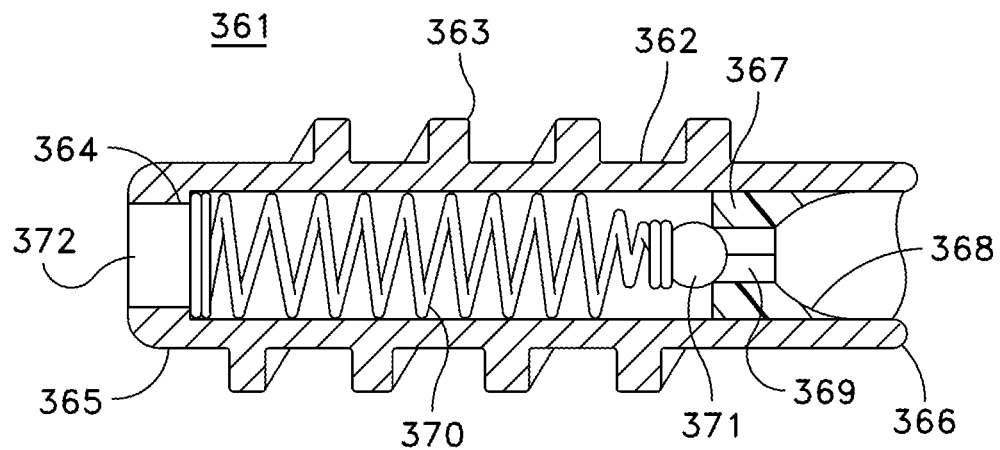
FIG. 23 is a cross-sectional view of an intraurethral catheter with flow control, showing the coiled wall reinforcement member acting as a spring on the ball of the check valve.
Figure 24:
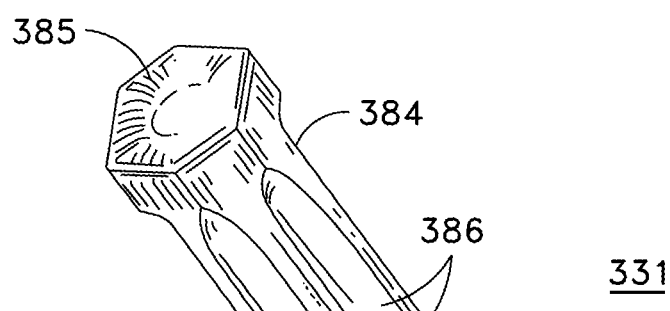
FIG. 24 is an enlarged perspective view of a stylet tip for operating the check valve of the intraurethral catheter of FIG. 23.

Referring now to FIG. 23, threaded intraurethral catheter 361, shown in cross-section, incorporates means for flow control. The catheter has a tube 362 made from a section of extruded polyurethane tubing material, with thread 363 of uniform pitch and not more than six turns applied to its external surface. Thread 363 preferably conforms to the same twenty percent (20%) "rule" of thread height to tube diameter, and ratio of thread pitch to thread circumference of less than one to one (1/1), as thread 103 in FIGS. 2 and 3 as described above.

Alternative embodiments may have a section of the thread being tapered to a lesser height or no height, to provide a "waist" for gripping by a muscular zone such as the prostate or sphincter. Also, a portion of reinforcement member 370 could be configured or molded into the side wall of tube 362.

There is an interior shoulder 364 at the distal end 365 of catheter 361, and a bushing 367 of relatively harder material disposed proximal to interior shoulder 304. Bushing 367 has a tapered interior wall 368 extending from the bushing's full diameter at one end to a uniform hexagonal aperture 369.

A coiled sidewall reinforcement member 370 and a check ball 371 are secured between interior shoulder 364 and bushing 367 so that coiled member 370 holds ball 371 in compression against the upper (proximal) end of bushing 367 in the manner of a check valve, whereby to prevent outward (proximal) flow through the lumen 372 of the stent. Coiled member 370 may be compressed by upward movement of ball 371, thereby opening the check valve to flow.

Referring next to FIGS. 19, 21, 23 and 24, alternate hexagonal tip 384 for stylet 331 has a slightly concave proximal end 385 and flutes 386. When used in conjunction with stent-follower 341 to actuate the check valve of catheter 361, tip 384 is adapted to be inserted through aperture 369 of catheter 361 to push ball 371 upward against coil member 370, thereby opening the check valve function and permitting outward flow of fluid through flutes 386 and aperture 369 and then into and through stent-follower 341.

Suprapubic

Figure 25:
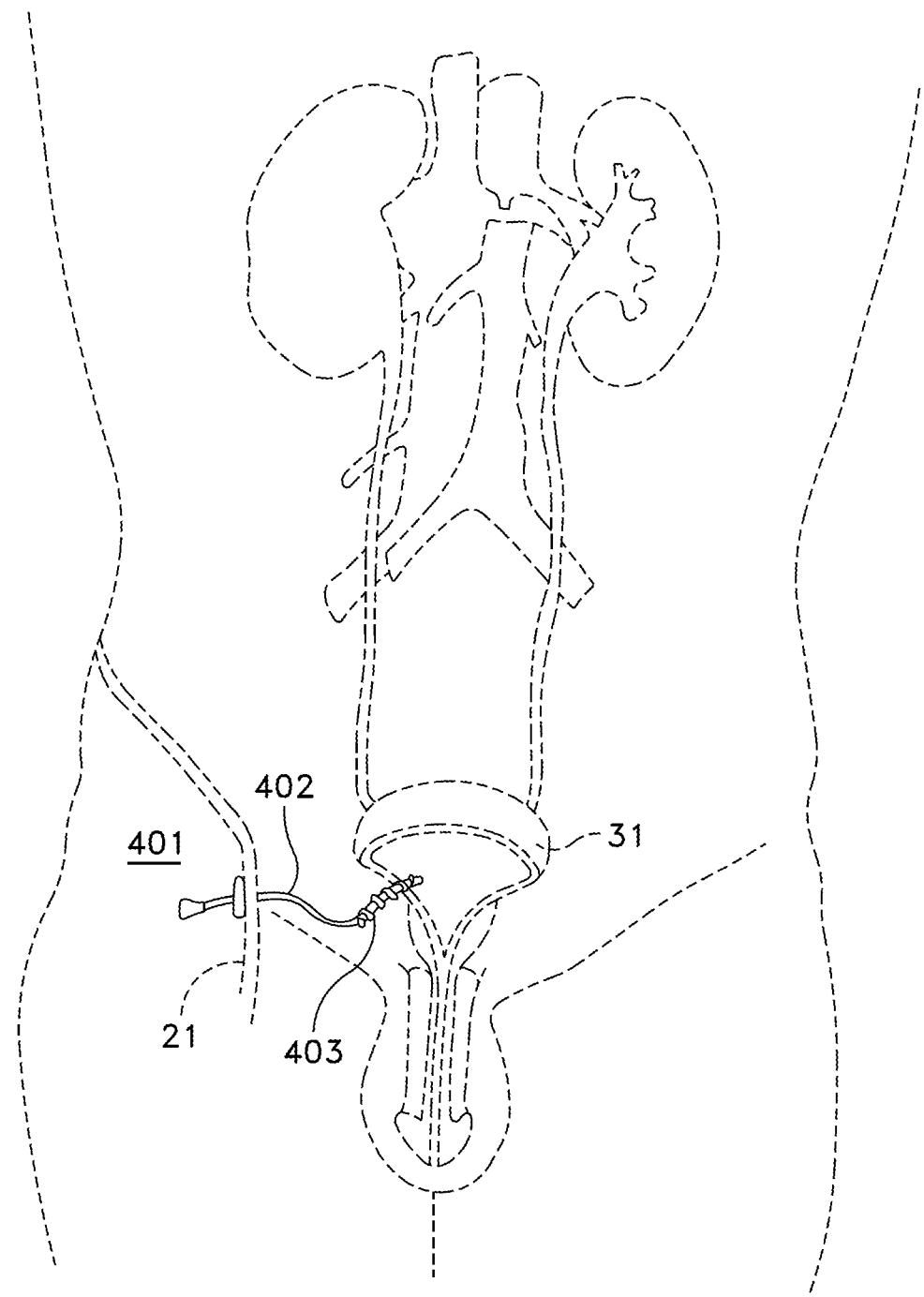
FIG. 25 is a diagrammatic illustration of a suprapubic catheter emplaced through the abdomen, with the distal end anchored by the helical thread in the bladder wall.
Figure 26:
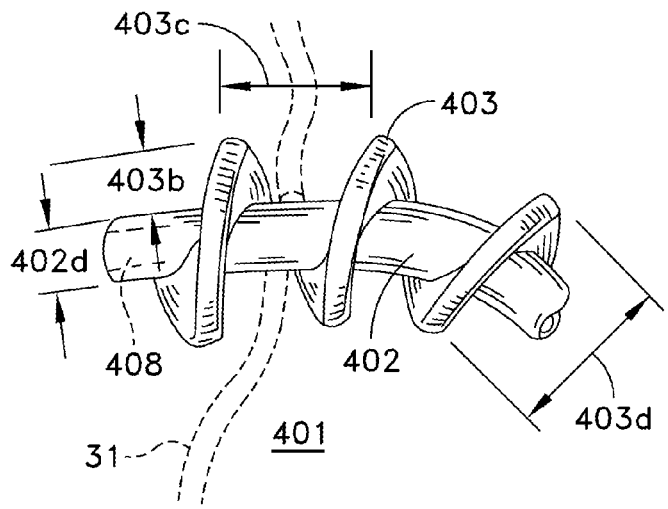
FIG. 26 is a partial side perspective view of the helical thread of the suprapubic catheter of FIG. 25, anchored by the helical thread in a hole in the bladder wall.

Referring now to FIGS. and 25-29, the threaded suprapubic catheter 401 of FIGS. 25 and 26 is constructed with a flexible tube 402, with a lumen 408 connecting axial ports at the proximal end and the distal end, and an external thread 403 of uniform pitch applied at its distal end. As described previously for catheter 101 of FIGS. 2 and 3, the ratio of thread pitch 403c to the circumference of thread diameter 403d is much less than one to one (1/1). Tube 402 is of sufficient torsional strength to accept and transmit rotational finger force, applied at the proximal end, to the distal end. The ends of thread 403 are tapered for ease of advancing and retracting the catheter through the abdomen and into the bladder wall.

Figure 27:
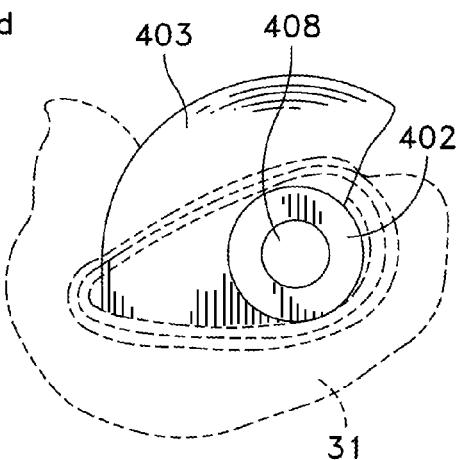
FIG. 27 is a partial front perspective view of the suprapubic catheter of FIGS. 25 and 26 anchored in a hole in the bladder wall, the hole being stretched and deformed to fit tightly about the tube and thread of the catheter.

Referring to FIGS. 26 and 27, relative thread height 403b, as a percentage of tube diameter 402d, is greater than in the case of catheter 101 of FIGS. 2 and 3; preferably greater than fifty percent (50%). This is because suprapubic catheter 401 is being advanced by the rotation of thread 403 along an unlined path through the abdomen, and being anchored against longitudinal displacement by the engagement of pitch 403c of thread 403 in a hole pierced into the wall of organ 31 that must encompass tube 402 plus thread 403 passing through the plane of the organ wall 31. This is distinguished from the longer gripping surface available in a lined passageway as is the case for the catheter 101 of FIG. 4.

Figure 28:
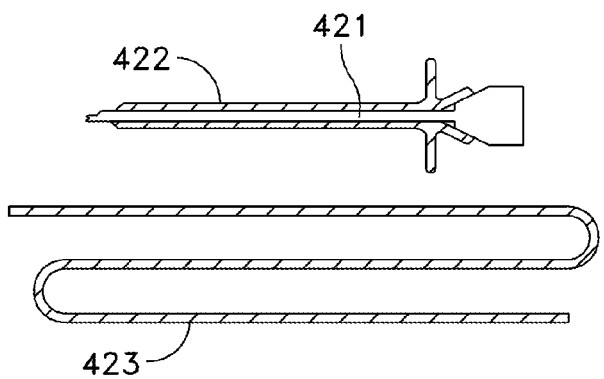
FIG. 28 is a diagrammatic view of a trocar, cannula and guide wire used to install the suprapubic catheter of FIG. 25.

Referring to FIG. 28, the method by which suprapubic catheter 401 is deployed is conventional to the extent that trocar 421 and cannula 422 are used with ultrasound or fluoroscopy to create the path through abdomen wall 21 into the bladder organ 31; trocar 421 is removed and temporary guidewire 423 is then inserted through cannula 422, extending from outside the abdomen wall 21 to inside the bladder organ 31. Cannula 422 is then withdrawn, leaving guidewire 423 as a connecting path, extending from outside the body, passing through the abdominal wall 21, and into the bladder organ 31.

Suprapubic catheter 401 is then threaded over the proximal end of guidewire 423, and gently started into the abdomen wall 21 with a rotating motion of about one turn until thread 403 is firmly engaged. The catheter is then rotatingly advanced along the guidewire through the unlined pathway in the same manner as other threaded devices of the present invention, until thread 403 penetrates the wall of organ 31 about one full turn, as determined by ultrasound, fluoroscopy or equivalent means. The distal end of catheter 401 is then secured in a non-rotatable fashion to abdomen wall 21 using conventional adhesive means or equivalent means, thereby locking thread 403 at the distal end of the catheter in position in the wall of organ 31. Guidewire 423 is then withdrawn. Threaded suprapubic catheter 401 is then available for use.

Figure 29:
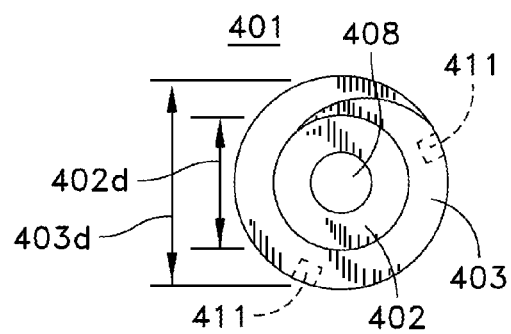
FIG. 29 is a distal end view of the suprapubic catheter of FIG. 21, showing rotational orientation markers.

Referring to FIG. 29, radiopaque markers 411, embedded at select points displaced along the perimeter of thread 403, provide the capability for external detection and monitoring (through fluoroscopy or other means) of the orientation and movement of the distal end of the catheter.

Threaded Camera Introducer

Referring next to FIGS. 30, 31A and 31B, threaded camera introducer catheter 500, suitable for an average size adult's colon or other bodily passageway, consists of a bulbous tip 501 connecting to a soft, flexible tube 502 which is about 5 feet long with a tube diameter 502d of 1 inch. Lumen 508 extends from the interior face of a window 511 on the distal end of tip 501, through tip 501 and tube 502 to the proximal end of tube 502.

Still referring to FIGS. 30, 31A and 31B, for a lower GI (gastrointestinal) application, external thread 503, preferably with uniform pitch 503c of 1.75 inches, begins at the edge of window 511, tapering from nothing to a height of about 0.5 inches, and continuing proximally for about 8 inches or more along tube 502.

An alternative embodiment of the introducer 500 may have a relatively diminutive tip, but maintain an external thread of equal or greater height and total circumference. Another variation of introducer 500 may have thread 503 applied only to the introducer's distal end, the thread terminating after a few turns, e.g., approximately 8 inches or less, analogous to catheter 101 of FIG. 2.

A thread major diameter in the range of 0.5 inches to 2.5 inches, and more preferably 1 inch to 2 inches, is desirable to expand and engage the walls of the colon of the adult intestinal tract to a sufficient depth to achieve a useful grip by the thread in accordance with the rotate-to-advance technology of the present invention. For other bodily passageways, other thread major diameters may be used. If desired, a trailing portion of the helical thread may have a lower thread height. The relatively lower thread height of the continuing thread may be employed to assist in the rotational advancement of the trailing length of the device without exerting undue forward pressure on the distal end.

It will be further apparent, consistent with the techniques, structure and methodology of the present invention, that the thread pitch 503c, is designed to produce the necessary leverage to translate rotational effort at the proximal end to a forward force greater than the friction against the wall of the colon or other bodily passageway. Simple vector analysis confirms this result.

Figure 32:
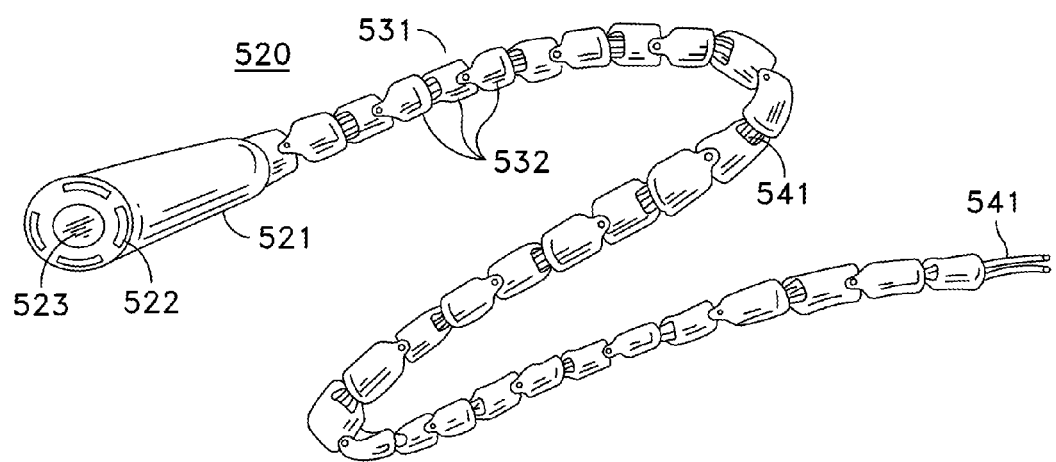
FIG. 32 is a perspective view of a camera assembly with a video camera or visual sensor head attached to a flexible torque tube or assembly within which run electrical cables and/or light bundles.

Referring to FIG. 32, a camera assembly 520 consists of camera 521, with light lens 522 and image lens 523, attached to a flexible, hollow, jointed spine 531. A cable harness 541, connected to camera 521, passes through spine 531, extending out the proximal end and connecting to the necessary power, control and display equipment. Spine 531 is constructed of a chain of vertebrae 532, connected by universal joints which combine flexibility with torsional strength.

Figure 33:
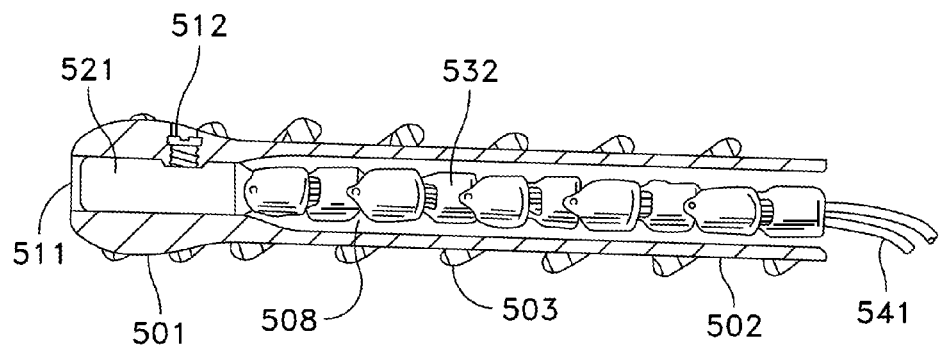
FIG. 33 is a partial cross-sectional view of the distal end of the preferred embodiment of FIG. 31A, with the camera assembly of FIG. 32 installed as it would be used.

Referring to FIG. 33, camera assembly 520 is shown installed in camera introducer catheter 501, with camera 521 secured within tip 501 by set screw 512, so that the camera views forward through the window. The camera assembly and catheter are combined here as a camera introducer system.

Figure 34:
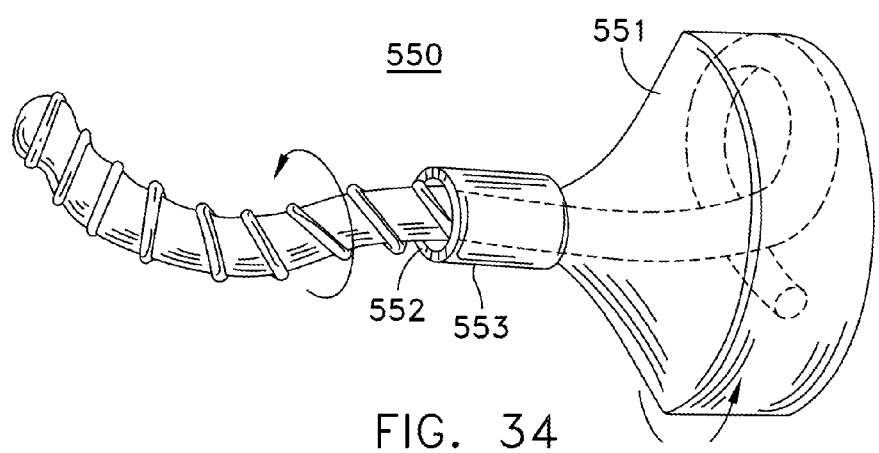
FIG. 34 is a rotating container and dispensing device by which the catheter of FIG. 30 may be managed and administered during application to a patient.

Referring next to FIG. 34, rotating container and dispensing system 550 consists of drum 551 with axial opening 552 around which handle 553 is rotatably attached. Catheter 501 is rotatingly dispensed during application by holding handle 553 and rotating drum 551 while catheter 501 is being rotatingly advanced in the subject colon or other bodily passageway.

As will be realized, the present invention is capable of other and different embodiments, and its several details are capable of modifications in various obvious respects, all without departing from the present invention. The objects and advantages of the present invention may be further realized and attained by means of the instrumentalities and combinations particularly pointed out in the appended claims. Accordingly, the drawings and description are to be regarded as illustrative in nature, and not as restrictive.

Threaded Camera Introducer with Rotary Coupling

In FIGS. 30-34, there is shown a threaded camera introducer catheter 500 which may be used to position a camera assembly 520 within a body passageway, e.g., the colon. Among other things, a significant advantage of the helical camera introducer is the ability to stabilize the visualization apparatus (e.g., endoscope) within the bodily passageway to improve visualization diagnostic yield. By way of example, the helical camera introducer can help stabilize a colonoscope during withdrawal around flexures in the mucus-lined colon, which reduces the risk of missing significant pathologies.

However, with the aforementioned assembly of (i) threaded camera introducer catheter 500 and (ii) camera assembly 520, camera assembly 520 is secured, both longitudinally and rotationally, to threaded camera introducer catheter 500, e.g., by means of set screw 512 (FIG. 33). Thus, when threaded camera introducer catheter 500 is rotated so as to advance camera assembly 520 within the colon or other bodily passageway, camera assembly 520 is also rotated. This presents two issues.

First, if camera assembly 520 is rotated during passage through a bodily passageway, e.g., the colon, the image observed by the medical practitioner (on either a video monitor or through an eyepiece) will also be rotating. This rotation can make it difficult for the medical practitioner to effectively use the visualization provided by the camera assembly during passage through the colon. At the very least, this rotation makes it difficult for the medical practitioner to maintain their sense of direction (i.e., up/down/left/right) during deployment. This latter point is significant, since the medical practitioner frequently relies on their sense of spatial orientation in order to navigate a tortuous passageway such as the lower GI tract. Stabilizing this image electronically requires complex additional circuitry and/or computer software in an already-costly scope and image processor system.

Second, if camera assembly 520 is rotated during passage through the colon, the camera assembly's umbilage connections (e.g., light, electrical, fluid, etc.) become complex. By way of example but not limitation, in such a situation, water connections to the distal end of the endoscope must be designed to rotate freely about the axis of the endoscope, with a leak-proof seal, etc. Again, this can add significant cost and complexity to an already costly and complex endoscope system.

The aforementioned issues are addressed by a new threaded camera introducer catheter which has a rotary coupling at its distal and/or proximal ends (and, if desired, at one or more intermediate locations) which is free to rotate relative to the body of the introducer. This new camera introducer catheter is installed over the distal end the endoscope, with the distal and/or proximal ends (and, if desired, one or more intermediate portions) of the endoscope being secured to the rotary coupling. Due to the fact that the endoscope is attached to the camera introducer catheter by means of the rotary coupling, the camera introducer catheter is free to rotate about its axis while the endoscope remains rotationally stationary.

This new arrangement allows the camera introducer catheter to rotate about its longitudinal axis, whereby to advance or retract the introducer (and hence the endoscope) within a bodily passageway, e.g., the colon; at the same time, however, inasmuch as rotation of the camera introducer catheter is not transferred to the endoscope, the endoscope (and hence all of its associated input and output connections) remains rotationally stationary. As a result, the new camera introducer catheter allows the medical practitioner to hold the proximal end of the endoscope in the customary manner, i.e., rotationally fixed, while deploying the endoscope using the rotate-to-advance methodology of the present invention. This is a significant advance in the art.

Figure 35:
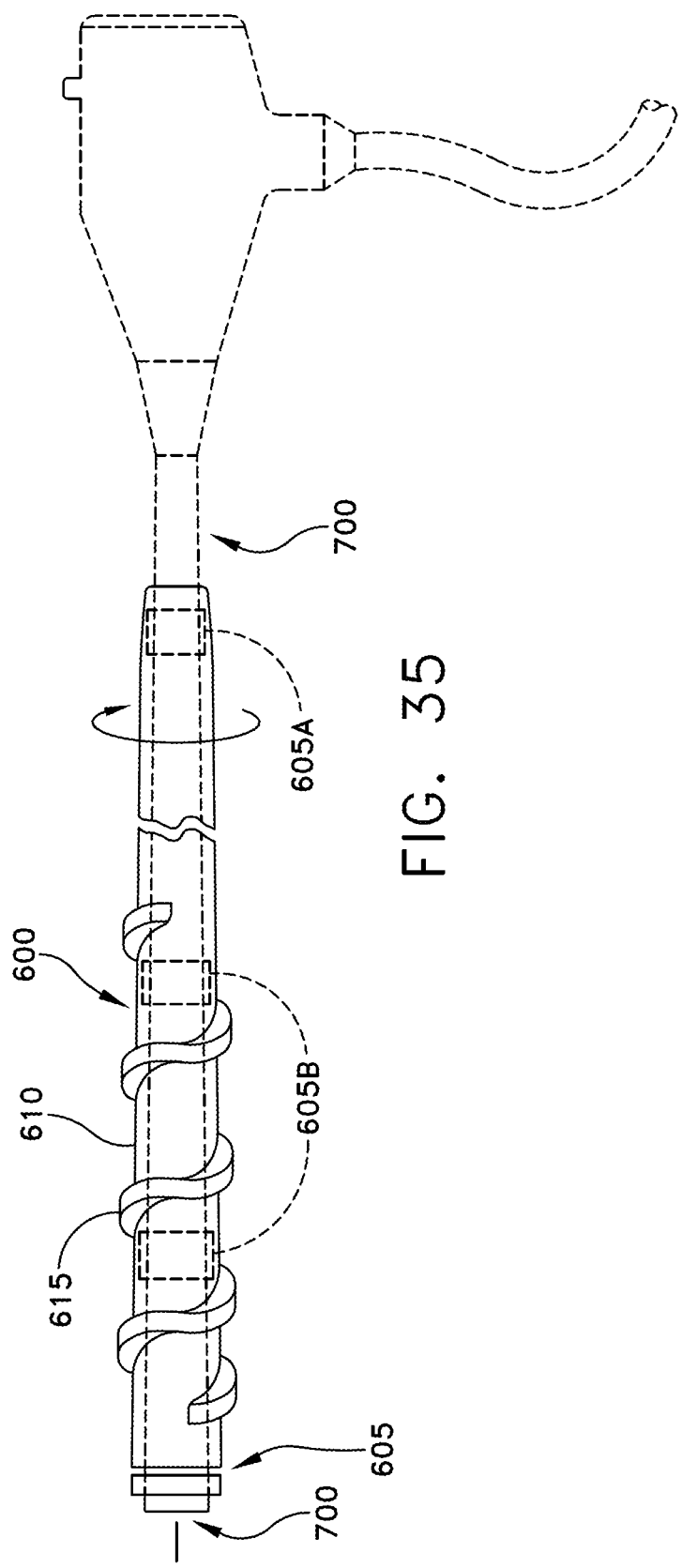
FIGS. 35-39 are schematic views showing various constructions for a camera introducer with rotary coupling.
Figure 36:
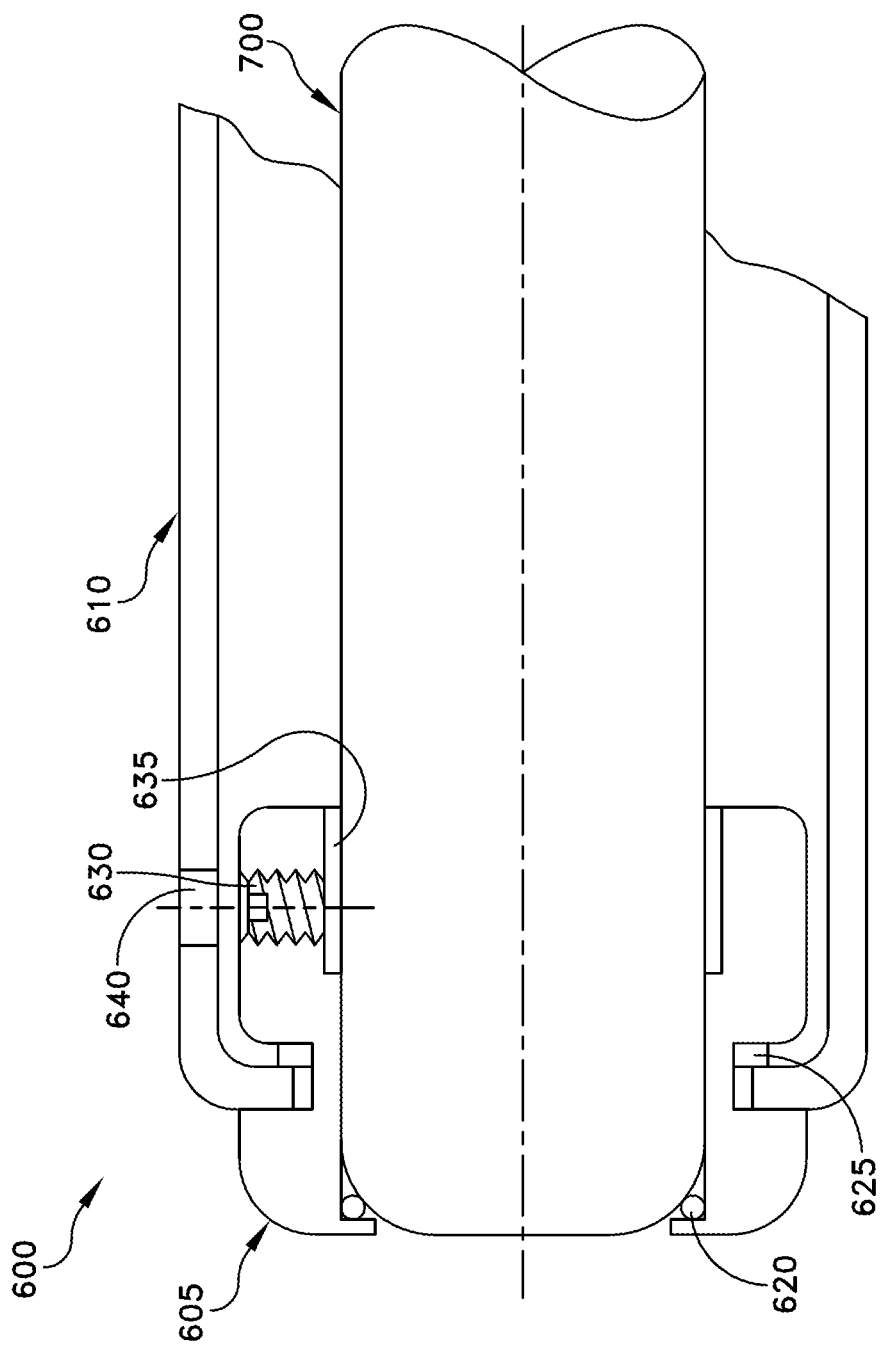

Looking next at FIGS. 35 and 36, there is shown a threaded camera introducer catheter 600 which may be used to position a camera assembly or endoscope 700 within the colon or other bodily passageway.

In one form of the present invention, camera introducer catheter 600 is preferably substantially the same as the camera introducer catheter 500 described above, except for the provision and use of one or more rotary couplings 605 which will hereinafter be discussed in further detail. More particularly, camera introducer catheter 600 generally comprises a tube 610 upon which is formed a helical thread 615. Tube 610 has sufficient rigidity that rotation applied to the proximal end of the tube will be transmitted to the distal end of the tube; at the same time, tube 610 also has sufficient flexibility that the tube may bend around curves in the colon. Furthermore, helical thread 615 has a geometry such that when the camera introducer catheter 600 is positioned within the colon, rotation of the proximal end of the catheter will cause helical thread 615 to pull the camera introducer catheter 600 along the colon, in the rotate-to-advance fashion of the present invention.

As referred to above, camera introducer catheter 600 includes one or more rotary couplings 605. In one preferred form of the present invention, a rotary coupling 605 is rotatably attached to the distal end of tube 610, such that the rotary coupling may rotate freely about the axis of the tube while being fixed, longitudinally, to the tube. Additional rotary couplings 605 may be disposed along the length of tube 610 and endoscope 700.

Preferably camera introducer catheter 600 is constructed so as to minimize friction between rotary coupling 605 and tube 610 when tube 610 is rotated. For example, low friction bushings or bearings may be used, and/or appropriate lubricants and/or coatings may be applied to contacting surfaces.

The joinder between tube 610 and/or endoscope 700 and/or rotary coupling 605 may be sealed to prevent fluid infiltration. This is particularly important at a distal end of the construction which is the portion most exposed to fluid ingress. A design addressing this feature may include labyrinth, point-contact and wiper configurations. See, for example, FIG. 36, where a pair of O-ring seals 620 and 625 seal the construction against fluid penetration.

The camera assembly or endoscope 700 is intended to be secured to rotary coupling 605 so that the endoscope will be longitudinally fixed to camera introducer catheter 600 but free to rotate relative to the camera introducer catheter. By way of example but not limitation, camera assembly or endoscope 700 may be mounted to rotary coupling 605 by means of a set screw 630 which causes a protective ring liner 635 into binding engagement with endoscope 700. Access to set screw 630 may be through an opening 640 in tube 610.

As a result of the foregoing construction, camera assembly or endoscope 700 may be secured to one or more rotary couplings 605 of camera introducer catheter 600 whereby, when the camera introducer catheter 600 is thereafter placed within the colon and the proximal end of the catheter's tube 610 is rotated, the distal end of tube 610 will turn, whereby helical thread 615 will pull the catheter (and hence endoscope 700) distally along the colon. At the same time, however, inasmuch as rotary coupling 605 is free to rotate with respect to tube 610, endoscope 700 will remain rotationally stationary with respect to the rotating catheter. In this way, endoscope 700 may be advanced within the colon using the rotate-to-advance technique of the present invention, without requiring any corresponding rotation of the endoscope itself. As a result, the medical practitioner will be able to maintain effective visualization of the colon as the endoscope is advanced (or retracted, with reverse rotation) within the colon. Furthermore, inasmuch as the endoscope per se does not to rotate, the endoscope's umbilage connection (e.g., light, electrical, fluid, etc.) are significantly simplified.

If desired, threaded camera introducer catheter 600 may be provided with multiple rotary couplings, with the additional rotary couplings being positioned anywhere along the length of catheter 600. By way of example but not limitation, and looking now at FIG. 35, a relatively short introducer catheter 600 might utilize a pair of rotary couplings, one (i.e., 605) at the distal end of the catheter and one (i.e., 605A) at the proximal end of the catheter; a longer introducer catheter 600 might include several additional rotary couplings, with the additional rotary couplings (i.e., 605B) being disposed between the two end rotary couplings. In this respect it should be appreciated that rotary couplings 605 may have varying lengths, depending on their construction. Thus, in one form of the present invention, a single rotary coupling 605 may extend along substantially the entire length of tube 610.

Figure 37:
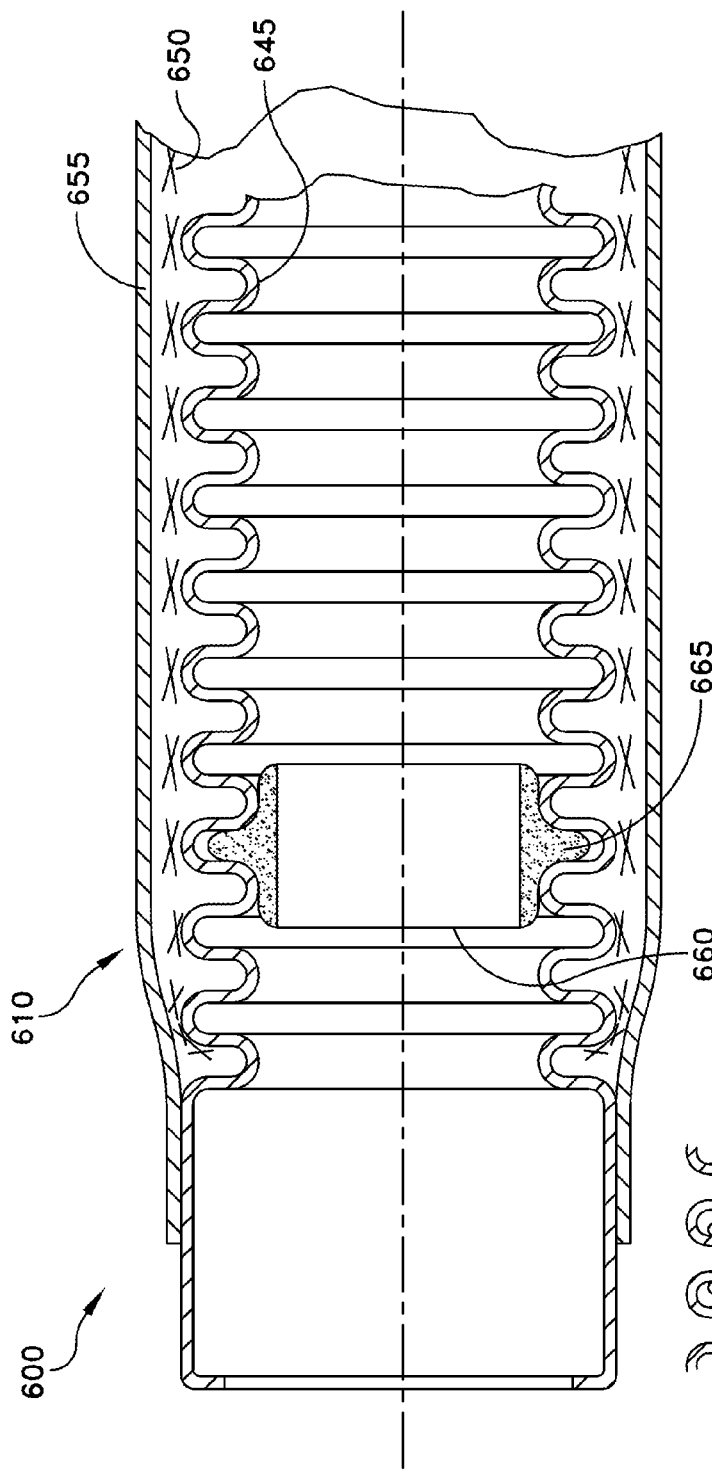
Figure 38:
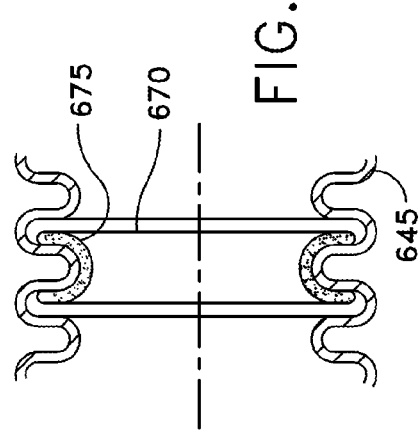

Furthermore, if desired, threaded introducer catheter 600 may include design features designed to maximize the torsional stiffness of its tube 610 while minimizing bending stiffness of the tube. By way of example but not limitation, and looking now at FIG. 37, tube 610 may be formed with a composite construction comprising an inner convoluted or corrugated tube 645, with or without a braided fiber layer 650, and with or without flexible outside layer 655. The term "corrugated tube" is intended to denote a tube configured with a plurality of parallel rings connected together by recessed floors. The term "convoluted tube" is intended to denote a tube configured with a continuous peak and floor that runs along the length of the tube in a helical configuration. The torsional and bending characteristics of the corrugated or convoluted tube may be optimized by varying the geometry and/or the material along the length of the device. Where such a construction. is used, one or more low friction bearings 660 (FIG. 37) may be positioned within the catheter's interior lumen so as to reduce surface contact with the endoscope (not shown in FIG. 37), where bearings 660 include a protrusion 665 which is adapted to ride in the helical trough of the convoluted or corrugated tube 645. Alternatively, and looking now at FIG. 38, one or more low friction bearings 670 may be provided, where bearings 670 include a recess 675 for receiving the helical peak of convoluted corrugated tube 645. Another embodiment utilizes a smooth liner disposed within the internal diameter of the corrugated tube 645 so as to reduce friction when a visualization device or instrument is disposed within the tube. This liner may be composed of multiple layers to allow for bending without kinking, such as an elastic layer supporting a low friction layer. The liner may employ a coating to reduce frictional drag, or be composed of a lubricant blended compound. By way of example but not limitation, one such compound may be polyethylene oxide which, when hydrated, produces a lubricating film on the liner surface.

Figure 39:
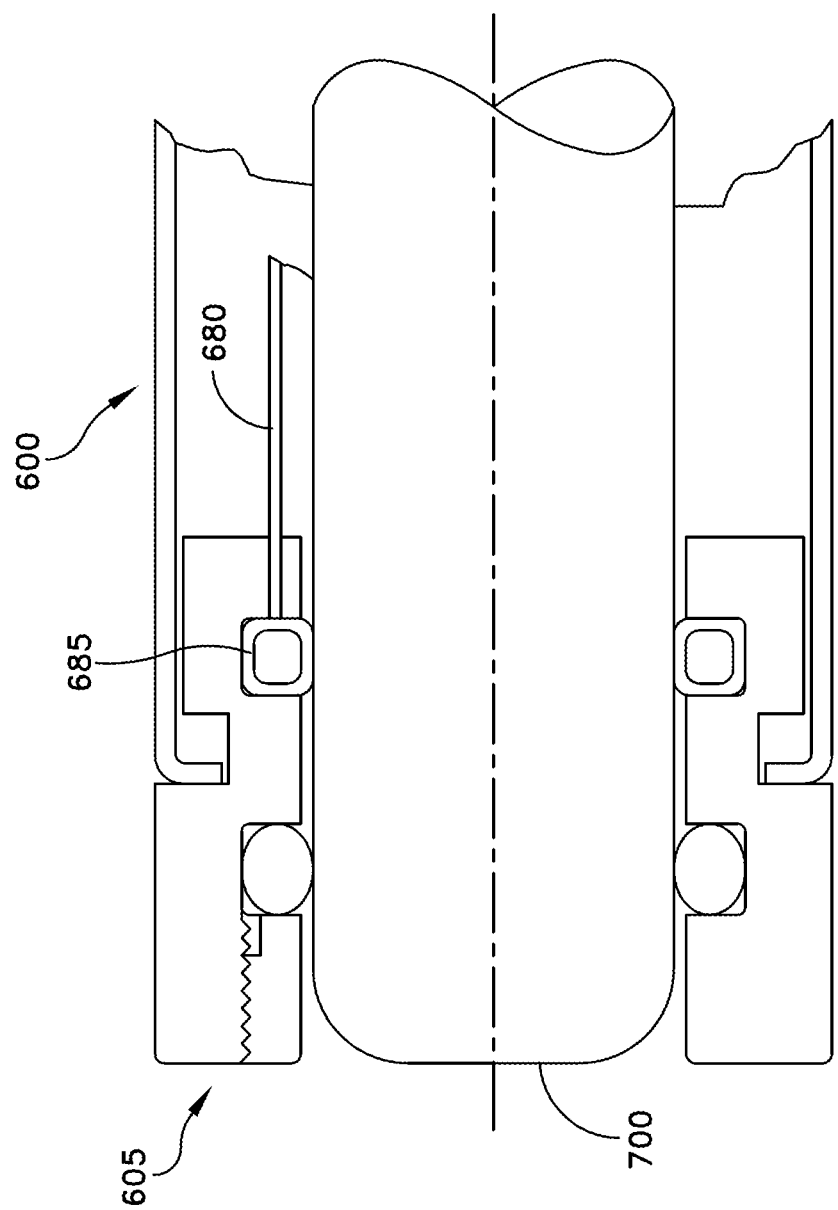
Figure 39A:
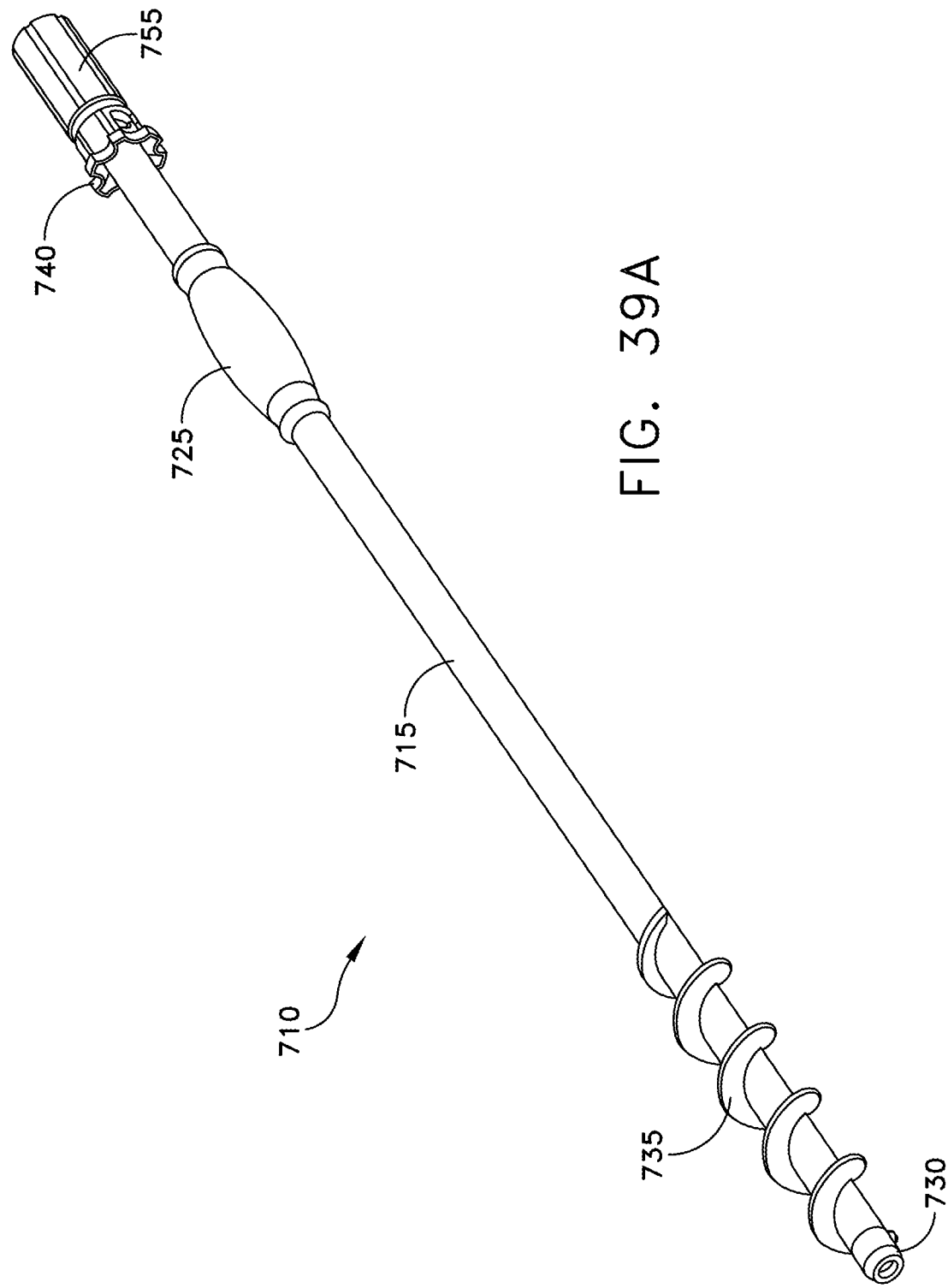
Figure 39C:
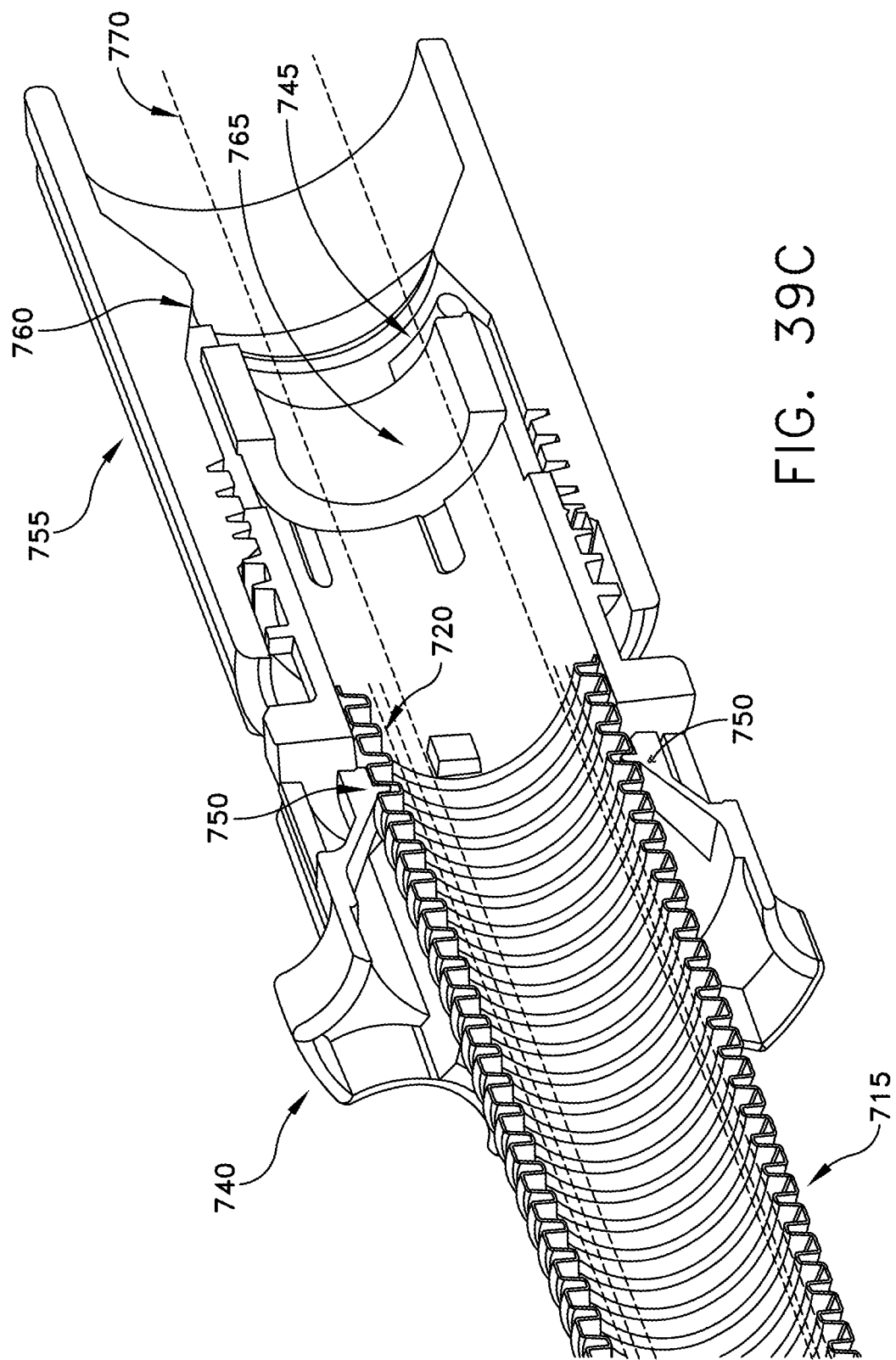
Figure 39D:
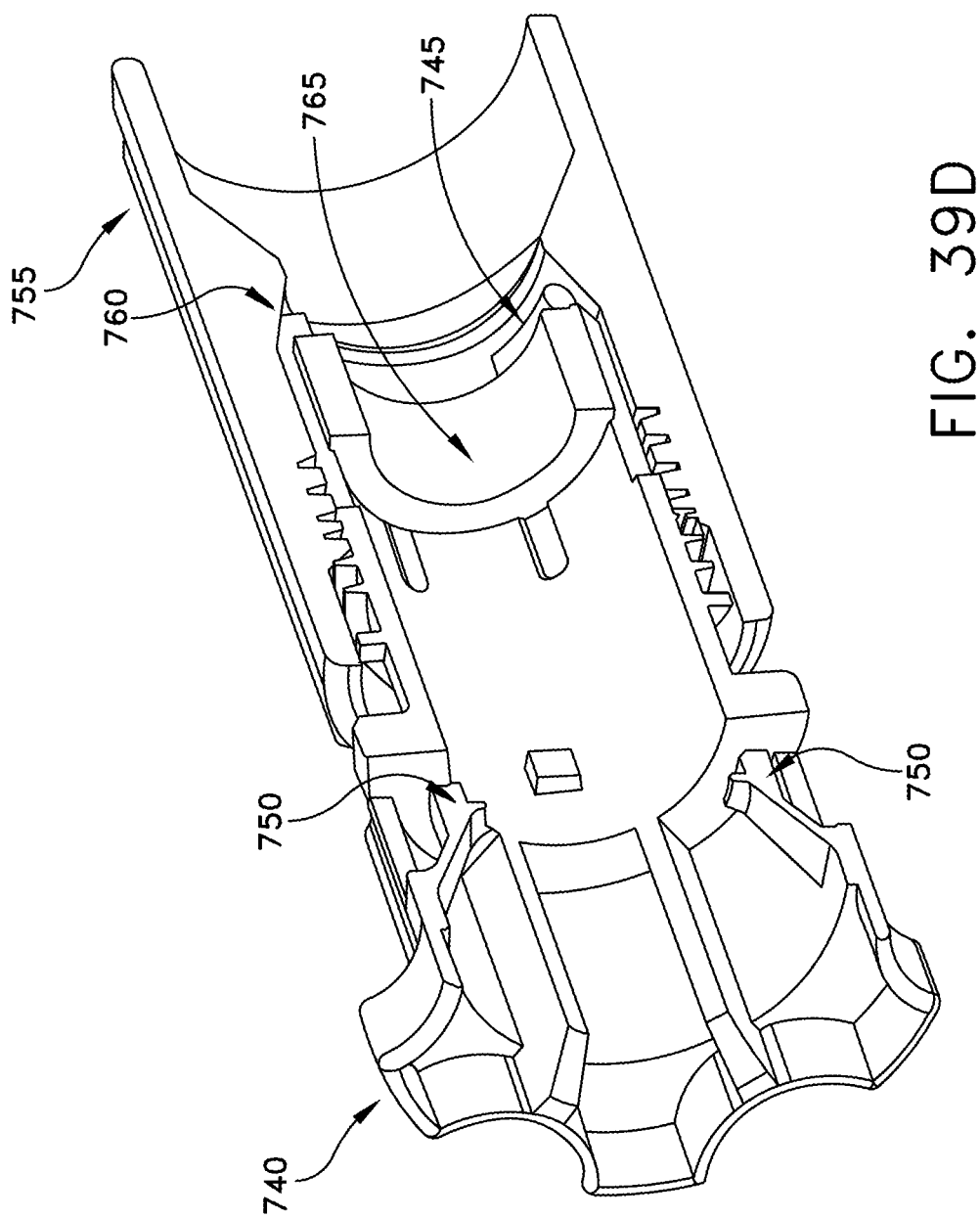

The threaded camera introducer catheter 600 may also include a feature to disconnect the rotary coupling 605 from the endoscope while the catheter 600 is deployed within the body. This disconnect may be effected via fluid, mechanical, electrical or other means. See, for example, FIG. 39, where a fluid line 680 is used to expand and deflate a bladder 685 so as to selectively bind and release, respectively, the endoscope 700 to and from rotary coupling 605.

It should also be appreciated that threaded introducer catheter 600 may be used to deploy objects other than an endoscope 700. For example, introducer catheter 600 may be used to deploy other visualization apparatus (e.g., ultrasound devices) and other objects which have umbilage associated therewith, e.g., a fluid dispenser apparatus, a vacuum snare, surgical instruments, etc.

Looking next at FIGS. 39A, 39B, 39C and 39D, there is shown a threaded camera introducer system 710 which comprises a corrugated tube 715 having a liner 720 disposed therein and a handle 725 positioned thereon. At the distal end of corrugated tube 715, there is disposed a nose cone 730 having helical threads 735 extending therefrom. Nose cone 730 is secured to the distal end of corrugated tube 715, and the helical threads 735 are secured to the outer wall of corrugated tube 715. A collet 740, having a plurality of flexible collet fingers 745, is rotatably mounted to the proximal end of corrugated tube 715. More particularly, collet 740 comprises a plurality of flexible snap lock fingers 750 which (i) flex to receive longitudinal advancement of the corrugated tube 715 into the collet body, but prevent withdrawal therefrom, and (ii) permit corrugated tube 715 to rotate relative to the collet body. A nut 755 threadingly engages collet fingers 745. Nut 755 includes an annular inclined surface 760, such that (i) when nut 755 is screwed distally, collet fingers 745 are driving radially inward, and when nut 755 is screwed proximally, collet fingers 745 are permitted to relax radially outwardly. An elastomeric ring 765 is disposed internally of collet fingers 745. As a result of this construction, an endoscope 770 may be inserted within corrugated tube 715, with nose cone 730 providing a sliding seal about the perimeter of the endoscope 770. Then nut 755 is screwed distally so as to close collet fingers 745, and hence elastomeric ring 765, into secure engagement with the endoscope 770. Thereafter, handle 725 may be turned whereby to rotate helical threads 735 and thereby move the system 710 within a bodily passageway. As this rotation of corrugated tube 715 occurs, endoscope 770 will be permitted to remain rotationally stationary, due to its ability to rotate within liner 720 and by virtue of the freedom of collet 740 to rotate freely relative to the distal end of corrugated tube 715. Thus, with this construction, liner 720 and collet 740 effectively provide the rotary coupling which permits endoscope 770 to remain rotationally stationary even as corrugated tube 715 rotates to move the system within the bodily passageway. If it is thereafter desired to free endoscope 770 from corrugated tube 715, nut 755 is screwed proximally so as to release collet fingers 745, and hence elastomeric ring 765, from gripping engagement with endoscope 770.

It should be appreciated that endoscope 770 may be secured within corrugated tube 715 so that the distal end of the endoscope projects out of the distal end of corrugated tube 715, so as to expose the angulation portion of the endoscope beyond the distal end of corrugated tube 715. Alternatively, endoscope 770 may be secured within corrugated tube 715 so that the distal end of the endoscope projects substantially beyond (e.g., greater than 6 inches or so) the distal end of corrugated tube 715.

Conventional Endoscope with Helical Threads

Figure 39E:
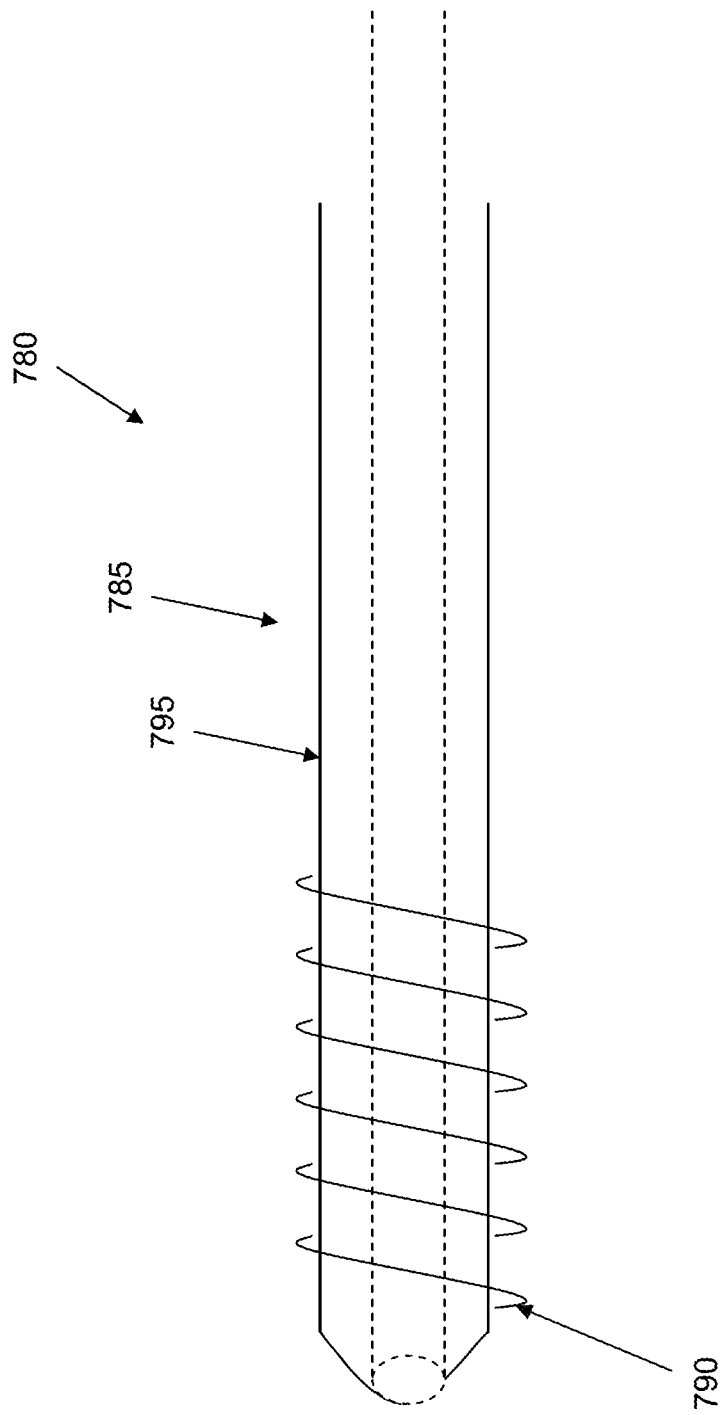
FIG. 39E is a schematic view showing a conventional endoscope with helical screw threads formed on its exterior sidewall.

In another form of the present invention, and looking now at FIG. 39E, there is shown a rotate-to-advance endoscope 780 which comprises a conventional endoscope 785 which has helical screw threads 790 along some or all of the exterior sidewall 795 of the endoscope, such that upon rotation of the endoscope, the helical threads will move the endoscope longitudinally within a bodily passageway. In other words, in this form of the present invention, helical screw threads 790 are disposed on the exterior surface of the endoscope itself.

Apparatus for Brachytherapy and Chemotherapy

The treatment of cancerous growths with brachytherapy is well documented. One approach is to surgically implant radioactive material into the cancerous growth in order to position the radiation source as close as possible to the target tissue. Such implantation can be difficult and time-consuming to effect. Furthermore, if the need subsequently arises to modify the radiation dosage or to limit the exposure to only a short time period, the implantation process can be difficult to reverse.

Thus, in accordance with the present invention, there is provided novel apparatus for effecting brachytherapy, that is, for directing radioactive material to a target site within the body, while allowing for easy implantation and removal.

Such novel brachytherapy apparatus may be cannulated or non-cannulated, depending on the anatomy which is to be targeted.

By way of example but not limitation, in one preferred application of the novel brachytherapy apparatus, the device may be used for the treatment of prostate cancer where the radioactive material must be delivered to the region of the affected prostate gland. In this case, it will generally be desirable to use a cannulated form of the present invention to effect delivery of the radioactive material.

More particularly, in this case, the novel brachytherapy apparatus may comprise a stent such as the stent 301 shown in FIGS. 16-18, along with its associated threaded scent-follower 341 shown in FIGS. 21 and 22, as well as its associated stylet 331 shown in FIGS. 19 and 20, except that the stent includes radioactive materials RM (FIG. 17) incorporated into its construction. As a result, when brachytherapy stent 301 is emplaced within the urethra adjacent to the target prostate tumor, the brachytherapy stent may irradiate the tumor so as to effect the desired brachytherapy.

By way of further example but not limitation, in another preferred application of the novel brachytherapy apparatus, the device may be used for the treatment of breast cancer, where the therapeutic radiation must be delivered to the breast. In this case, it may be desirable to use a non-cannulated form of the present invention.

More particularly, in this case, the novel brachytherapy apparatus may comprise a threaded solid element such as the dilator 201 shown in FIG. 13, except that the dilator may include radioactive materials RM (FIG. 13) incorporated into its construction. As a result, when brachytherapy dilator 201 is advanced through a mammary canal (accessed through an opening on the nipple) and into the interior of the breast, whereby it may reside adjacent to a target tumor, the brachytherapy dilator may irradiate the tumor.

It is also anticipated that the radioactive materials RM of the aforementioned brachytherapy stent 301 and/or the aforementioned brachytherapy dilator 201 may be replaced by a therapeutic agent capable of leaching out of the wall of the delivery device and thereby be delivered to the target tumor. Additionally, the therapeutic agent may be coated onto a wall of the delivery device for delivery to the target region.

Conduit Fitting

Figure 40:
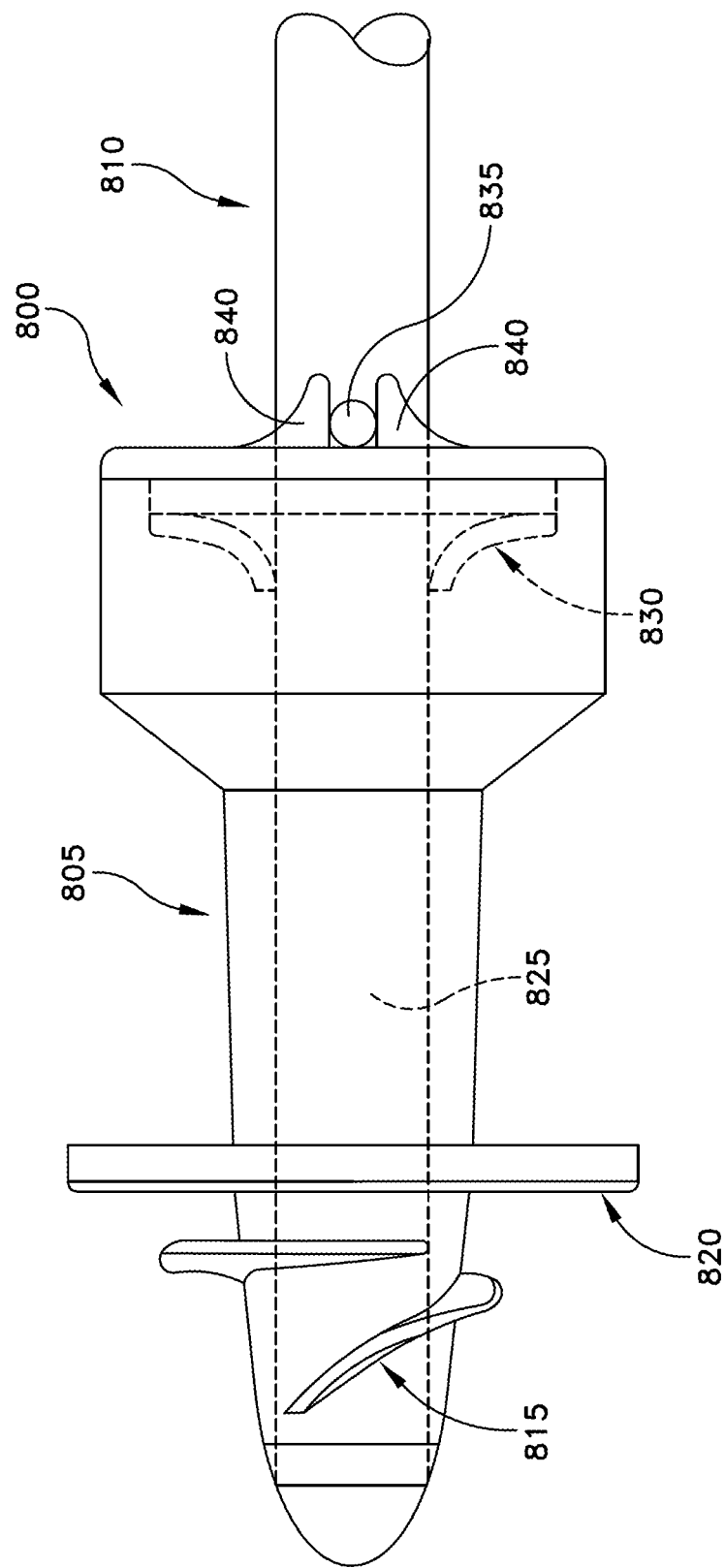
FIG. 40 is a schematic view of a conduit fitting formed in accordance with the present invention.

Looking next at FIG. 40, there is shown a conduit fitting 800 which can be used to provide a quick and effective access to a corporeal conduit such as an artery or vein, etc.

Conduit fitting 800 generally comprises a body 805 and an obturator 810. Body 805 has a helical thread 815 formed on its distal end, and an enlarged flange 820 formed on body 805 proximal to helical thread 815. A central lumen 825 extends the length of body 805. A fluid valve 830, preferably in the form of one or more deformable seals, is disposed at the distal end of the device so as to selectively close off lumen 825.

Obturator 810 is sized to fit within, and close off, lumen 825 of body 805. In addition, obturator 810 is adapted to drivingly engage body 805, whereby rotation of obturator 810 may be converted into corresponding rotation of body 805. By way of example but not limitation, obturator 810 may be drivingly connected to body 805 by an obturator pin 835 which engages a pair of body ears 840.

In one contemplated manner of use, a small hole is first made into a corporeal conduit, e.g., a blood vessel. The distal end of body 805, with obturator 810 in place, is then inserted into the hole. Next, obturator 810 is turned so as to cause body 805 to turn, whereupon thread 815 will pull the distal end of body 805 into the interior of the blood vessel. Engagement of flange 820 with the outer surface of the blood vessel will prevent further movement of body 805 into the blood vessel.

Engagement of flange 820 can also assist in sealing the blood vessel against leakage. To this end, flange 820 may comprise a compliant seal and/or may comprise a thrombogenic agent. Obturator 810 may then be removed; however, blood will not pass out of the proximal end of body 805 due to the presence of fluid valve 830. Thereafter, when instruments or the like are to be introduced into the blood vessel by means of body 805, they may be pushed through the fluid valve 830 and lumen 825.

When access to the blood vessel is no longer required, body 805 may be backed out of the blood vessel, e.g., by reinserting obturator 810 into body 805 so that obturator pin 835 engages body ears 840, and then appropriately turning the distal end of the obturator so as to unscrew body 805 from the wall of the blood vessel.

Body 805 is preferable absent of perforations so as to minimize any ingrowth of tissue into the body, which may render subsequent removal more difficult. Additionally, various materials and/or coatings may be used to minimize tissue ingrowth to body 805.

Access Device

Visual examination of the large intestine (colonoscopy) is performed by passing a colonoscope, retrograge, the entire length of the intestine, starting at the rectum and advancing to the cecum.

Standard practice is to lubricate the colonoscope and the entry site (i.e., the anal sphincter) prior to inserting the colonoscope with a combination of push-and-quarter turn twisting motion.

This insertion can be especially challenging where the patient is not relaxed and the sphincter muscle is held tightly closed. Hemorrhoids can also cause discomfort when the instrument is advanced into the anal sphincter. Also, to the extent that a helically-threaded introducer (such as the threaded introducer catheter 500 described above) is used to deploy the endoscope, the presence of the introducer's helical threads can add to the challenge of inserting the colonoscope into the rectum.

To this end, and looking now at FIGS. 41-43, a novel access device 900 is provided. Access device 900 comprises two main elements, a liner 905 having a central lumen 907 and an obturator 910 sized to selectively close off lumen 907.

In use, obturator 910 is first positioned in lumen 907 of liner 905, and then the assembly is inserted into the rectum. Once access device 900 is inserted in the rectum, obturator 910 is removed, thereby providing a tubular access into the rectum. Then the colonoscope (with associated threaded introducer catheter 500 if desired) can be passed freely into the rectum.

Liner 905 may or may not have a helical thread or other surface geometry on the exterior of the tube to help advance the liner into the rectum or to help keep it in place. Additionally, liner 905 may be designed with a feature to cause it to split so it can be easily removed from the procedure site once the colonoscope has entered the rectum.

Powered Drive

Figure 44:
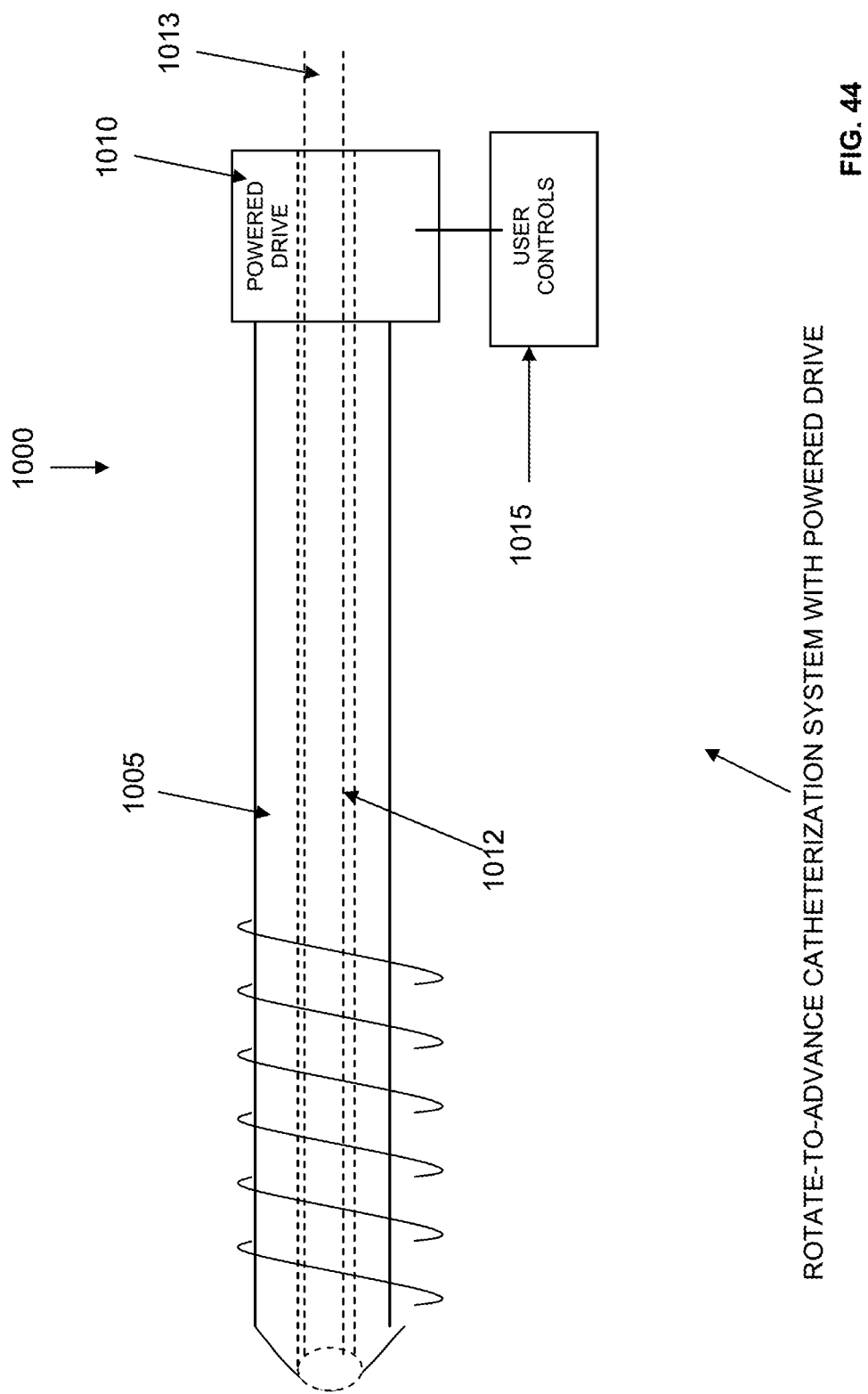
FIG. 44 is a schematic view of a power driven catheter system formed in accordance with the present invention.

In accordance with some preferred embodiments of the present invention, and looking now at FIG. 44, there is shown a catherization system 1000 which comprises a threaded catheter 1005 and a powered drive 1010. The threaded catheter 1005 comprises a central lumen 1012 for receiving instruments therewithin, e.g., an endoscope 1013. The powered drive 1010 may be used to rotate the threaded catheter 1005 and thereby advance the threaded catheter 1005 along the bodily passageway.

The powered drive 1010 can be detachably attached to the threaded catheter 1005 either before or after the initial insertion of the threaded catheter 1005 into a bodily passageway. Furthermore, the powered drive 1010 may be placed anywhere along the length of the threaded catheter 1005. In one preferred form of the present invention, the power drive is placed at the proximal end of the threaded catheter.

The energy input to the powered drive 1010 may be one source or a combination of sources. By way of example but not limitation, the energy source may comprise electrical, hydraulic, pneumatic, ultrasonic, magnetic and/or other energy sources. It should be appreciated that these energy sources may be disposed anywhere along the length of catherization system 1000, or they may be remotely located. The energy from the energy source(s) may be transmitted to the rotating helix via a permanent or detachable coupling mechanism. This coupling mechanism is preferably used in conjunction with the rotary bearing mechanism disclosed above.

The powered drive 1010 may be constructed in a configuration which minimizes its external size so as to accommodate the body orifice that the device is traversing. Additionally, the powered drive 1010 may include "coreless motors" or "coreless drive mechanisms" which may provide a lumen for passing tools, fluids, optical devices, etc. through the threaded catheter to the surgical site.

In accordance with some preferred embodiments of the present invention, the powered drive 1010 may be controlled directly by the physician using user controls 1015 (see FIG. 44). Such user controls 1015 may comprise a switching device, such as a momentary switch, which cuts off power to the powered drive 1010 once the switching device is no longer engaged. Alternatively, the user controls 1015 may comprise a Graphical User Interface (GUI).

Significantly, the aforementioned switching device may also be designed to reverse the direction of catheter rotation (i.e., clockwise vs. counterclockwise) so as to control advancement and refraction of the rotary introducer within the bodily passageway.

In accordance with other preferred embodiments of the present invention, the aforementioned switching device may also incorporate a "throttle" feature so as to allow the user to vary the speed of catheter rotation, as well as a force feedback output so as to give the physician an indication of the amount of resistance the device is encountering as it advances into the bodily passageway. Such a feature may constitute a safety measure that may prevent high rotational forces from being inadvertently applied to the threaded catheter, thereby minimizing risk of injury to the patient.

It will be appreciated that if it is necessary to advance a portion of the powered drive 1010 (or even the entirety of the powered drive 1010) into a bodily passageway during use of the present invention, a small diameter powered drive 1010 should be used.

The powered drive 1010 may be designed so as to be cleanable and reusable, or powered drive 1010 can be disposable.

It should be appreciated that the powered drive 1010 may be used in a system additionally comprising conduits extending through the threaded catheter for air/water/suction and tool passage (as described hereinabove and/or hereinbelow).

It should also be appreciated that the powered drive 1010 may be used with imaging devices which deliver data through the catheter shaft via fiberoptic cables or electrical signals. Alternatively, the image signals could be transmitted from the distal end of the catheter to a remote receiver so as to eliminate the need for an electrical connection. Similarly, the powered drive 1010 may also be remotely controlled via a wireless connection.

In accordance with some example embodiments of the present invention, it is possible to utilize two counterwound helical sections that rotate in opposite directions so as to eliminate the need for the torsionally rigid spline. A device in accordance with such embodiments may be constructed with an integral power supply and drive mechanism, and a mechanized surgical tool which is remotely controlled (i.e., wireless), and a wireless image transmitter so as to enable an untethered instrument. This instrument could be driven into a bodily lumen and perform a diagnostic or therapeutic procedure, all via wireless (e.g., remote) control.

A small diameter helical catheter 1005 may be utilized to access other bodily passages such as the mammalian ducts, bile ducts, or other areas of the body where a flexible shaft approach is advantageous.

Lavage System

To properly examine and treat conditions of the lower gastrointestinal tract, the patient typically undergoes a purging to remove fecal matter. If this procedure is not conducted successfully, it is generally very difficult to visualize the bodily passageway clearly. This is highly undesirable, since anatomical abnormalities may be hidden from the endoscope.

In current procedures, the preparation of the patient involves consuming a large volume of liquid and a purging agent such as magnesium citrate. This causes the desired flushing of the intestines, but it is also accompanied by unpleasant cramping for hours after consumption. Patients have complained that this is one of the worst parts of undergoing flexible endoscopy. In fact, this unpleasant procedure deters some patients from undergoing colon endoscopy. It should also be noted that the alternative, i.e., a colonic enema, is generally not adequate to clear the lumen prior to endoscopy.

Figure 45:
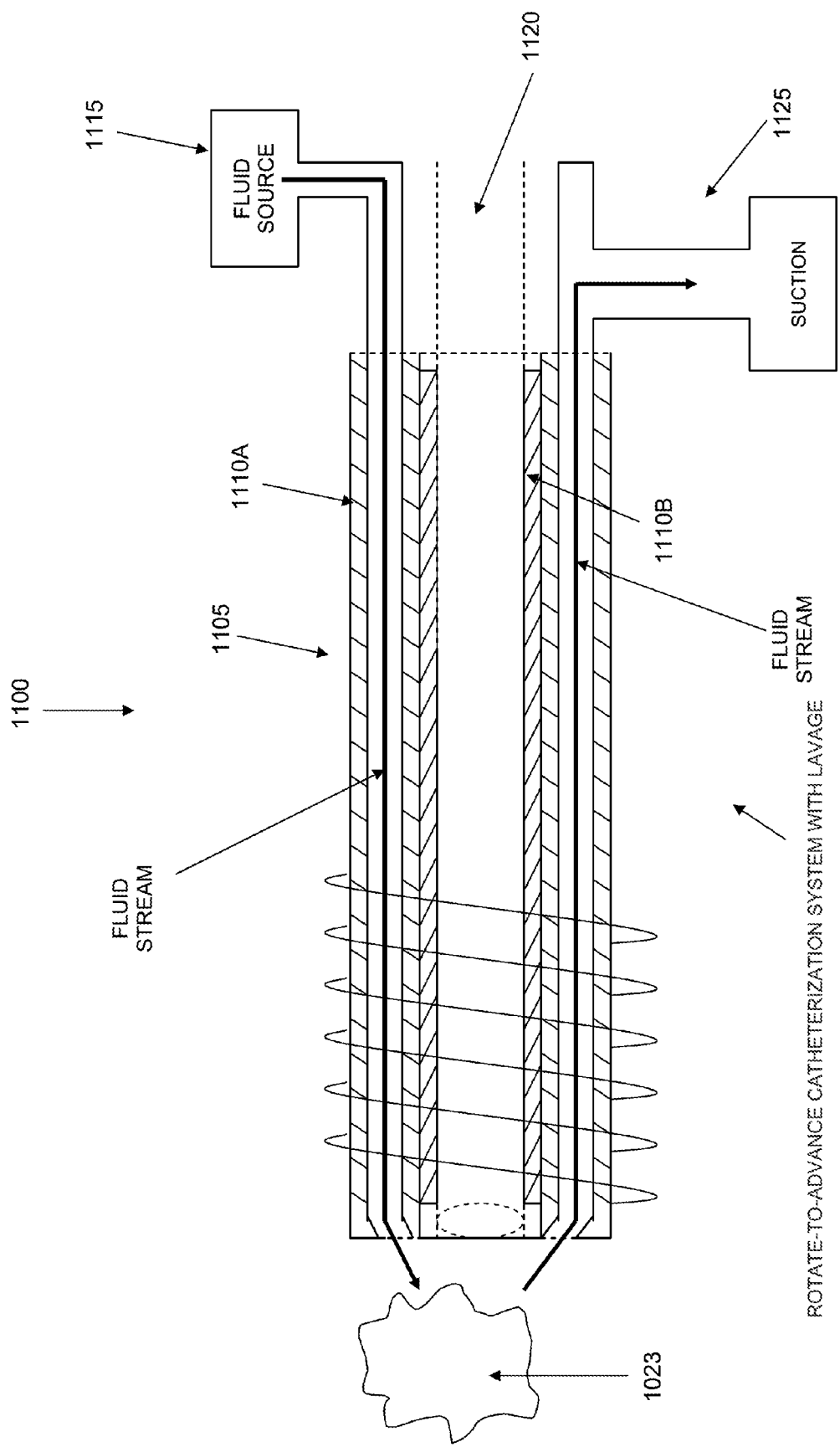
FIG. 45 is a schematic view of a catherization system with a lavage feature formed in accordance with the present invention.

To overcome the foregoing deficiencies, a rotate-to-advance catheter system 1100 (FIG. 45), comprising a threaded catheter 1105 incorporating a lavage system, has been developed to clear away debris from the bodily passageway in front of the endoscope. In one form of the present invention, the lavage system comprises two or more lumens 1110 extending through the rotate-to advance catheter 1105. One lumen, 1110A, carries fluid from a fluid source 1115 to the region at the front of the endoscope 1120 to break up and flush fecal matter 1123 away from the front of the endoscope. The second lumen, 1110B, withdraws the fluid (and the fecal debris) from the bodily passageway via suction, e.g., supplied by suction source 1125.

In one embodiment of the present invention, to aid the colon cleaning process, jets may be disposed at the indwelling tip of the threaded catheter so as to produce an increased velocity of fluid entering the bodily passageway. Additionally, these jets may be aimed back into the suction lumen to create an increased suction to remove fecal matter.

It should be appreciated that the lavage system described hereinabove may be used in connection with the camera introducer described hereinabove, and/or it may be used in any procedure requiring the insertion of a surgical apparatus into a bodily cavity in which cleaning of the cavity is advantageous.

Preferred Urological Stent

Figure 46:
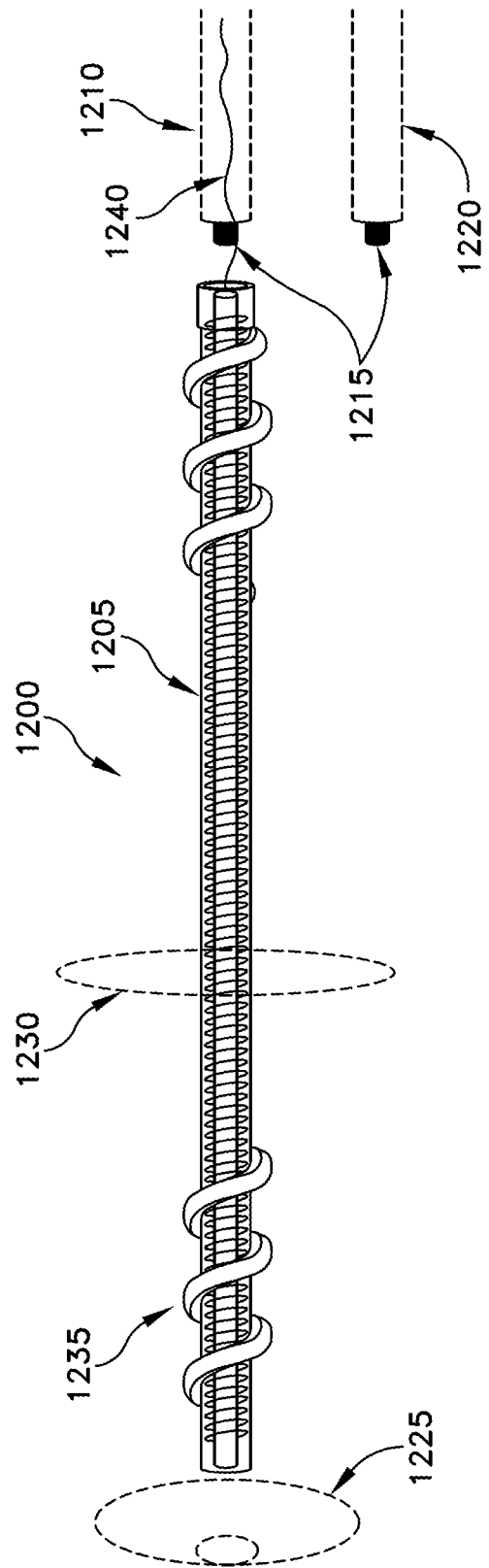
FIG. 46 illustrates a preferred prostatic stent construction.

Looking next at FIG. 46, there is shown one preferred urological stent construction formed in accordance with the present invention.

In one preferred form of the present invention, the urological stent 1200 comprises (i) an implant component 1205 (i.e., the stent), (ii) a delivery element 1210 (i.e., the element which delivers the implant component into position), (iii) a connect/disconnect element 1215 (i.e., the element which allows the delivery and/or retrieval elements to interface with the stent), and (iv) a retrieval element 1220 (i.e., the element which enables removal of the stent from the body).

The stent implant of the present invention may comprise a preformed "J" shape, a balloon and/or protrusions 1225 (a balloon 1225 is shown in FIG. 46) at the distal end of the stent which extends into the bladder to prevent the stent from migrating downstream (i.e., away from the urinary bladder) after deployment. In addition, other protrusions 1230 are preferably provided on the distal end of the stent. These additional protrusions are preferably in the form of fingers, fibers, flaps, discs, etc., and extend outwardly so as to resist migration of the stent towards the bladder. These additional protrusions 1230 are typically configured to extend or be exposed after the stent is delivered to the proper location by means of swelling (e.g., liquid absorption), heat, stored energy, electric/electrical signal, ablation, and/or other methods known in the art.

The delivery is facilitated by providing a helix 1235 on the stent to advance the stent and the trailing delivery system to the proper location. The proper location can be confirmed by urine flow, i.e., urine will flow once the stent extends to the bladder. Alternatively, traditional imaging methods can be used to confirm location (e.g., x-ray, ultrasound, etc.). When the stent is properly located within the urethra, adjacent to the prostate and on the bladder side of the external sphincter, the stent is disconnected from the delivery element 1210.

Connecting and disconnecting of the stent 1200 from the delivery 1210 and/or retrieval elements 1220 may be conducted via wireless signal, push/pull of a wire or cable, inflation/deflation of a balloon or bladder, screwing/unscrewing of threaded elements, thermal expansion/contraction, swelling/shrinking, on/off tapered elements, magnetizing/demagnetizing, wrapping/unwrapping elements, sticking/unsticking, grabbing/releasing and/or other methods which will be apparent to those skilled in the art in view of the present disclosure. In this respect it should be noted that the shape of the connect/disconnect elements 1215 are generally non-circular, and may be hexagonal, square, triangular, slotted, star-shaped, hole-with-detent, etc.

It should be noted that during use, metal or non-metal tethers 1240 may be kept in place at the time of delivery so as to thereafter function, if necessary, as a guide for connecting the retrieval element 1220 to the stent for removal of the stent 1200. The retrieval element 1220 is guided to the stent by a guide wire which is advanced to the stent 1200 in advance of the retrieval element 1220.

In one preferred form of the present invention, the stent may be disassembled or separated into two or more pieces before removal.

Preferred Fallopian Catheter Construction

Figure 47:
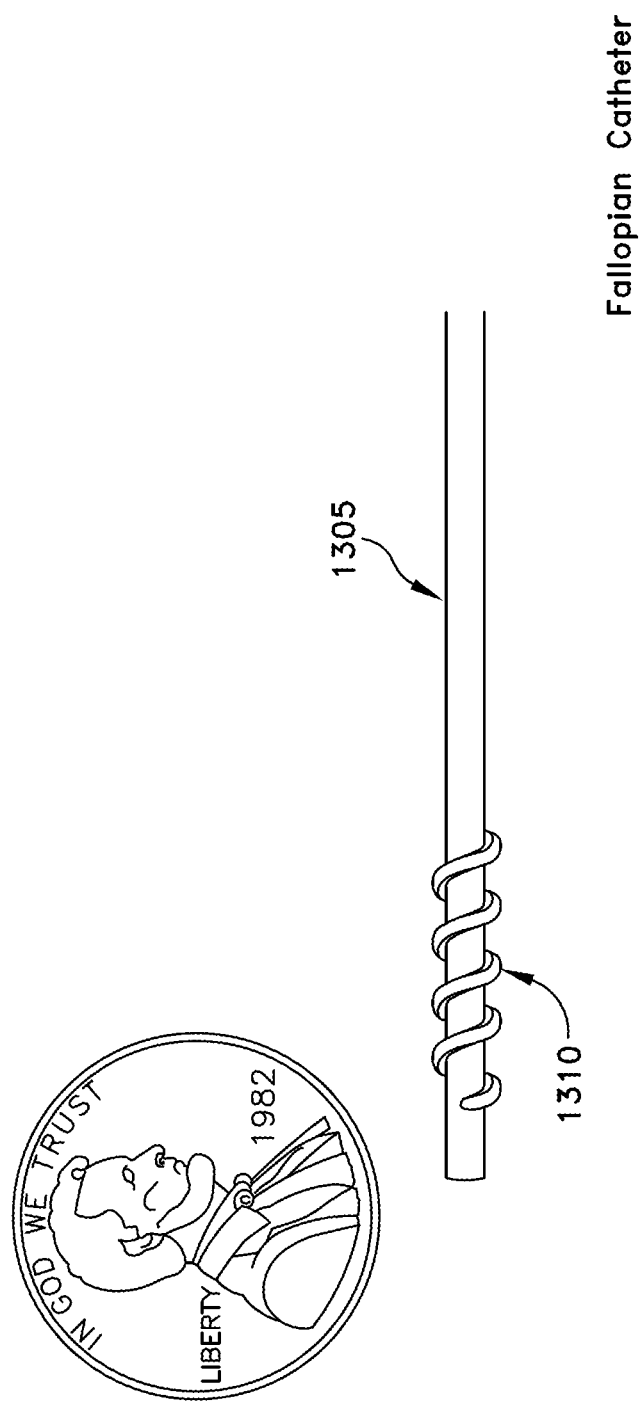
FIG. 47 illustrates a preferred fallopian catheter construction.

Looking next at FIG. 47, there is shown one preferred fallopian catheter 1300 formed in accordance with the present invention.

In one preferred form of the present invention, the fallopian catheter 1300 comprises a body 1305 having helical. threads 1310 formed thereon. Body 1305 and helical threads 1310 are sized for disposition in a fallopian tube.

Threaded Camera Introducer System for Small Bowel Applications

Looking next at FIGS. 56-62, there is shown a helically-threaded camera introducer system 710A which may be used to access, and position an endoscope 770A within, the small bowel. As discussed above, a significant advantage of the helical camera introducer system 710A is its ability to control (both longitudinally and rotationally) the visualization apparatus (e.g., endoscope 770A) within the body passageway (i.e., the small bowel) in order to improve visualization and diagnostic yield, as well as to provide a stable platform for therapy. By way of example but not limitation, helical camera introducer system 710A can help stabilize an endoscope during insertion into, and withdrawal out of, the torturous and delicate anatomy of the small bowel.

Camera introducer system 710A is generally similar to camera introducer 710 discussed above, except that it is specifically configured to be used in small bowel applications, in either antegrade or retrograde fashion, as will hereinafter be discussed in further detail.

Figure 57:
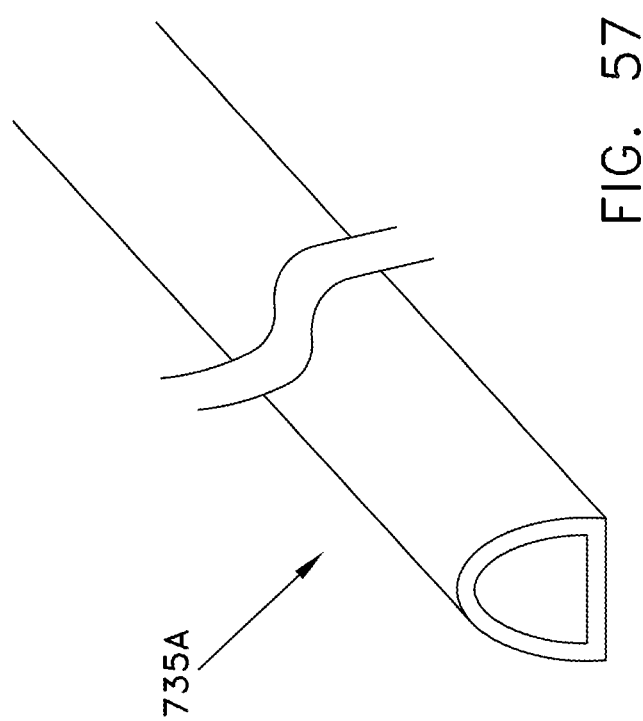
Figure 58:
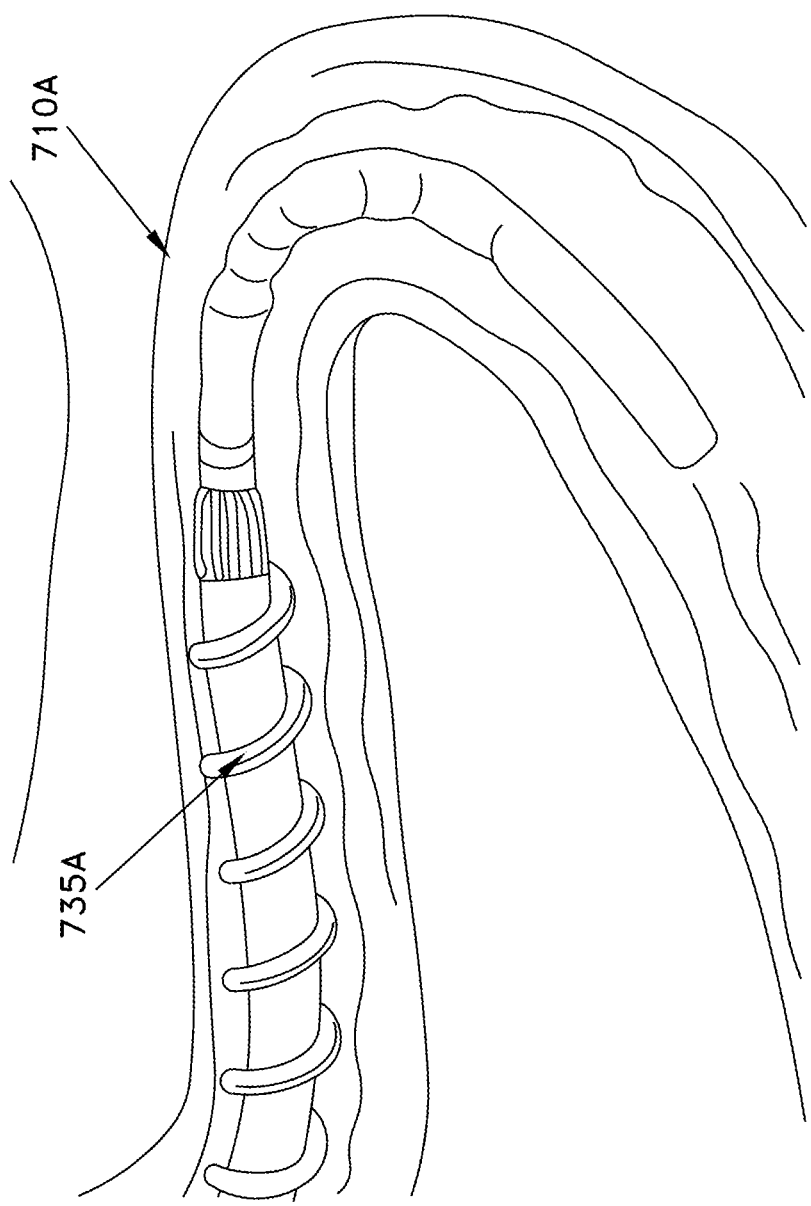
Figure 59:
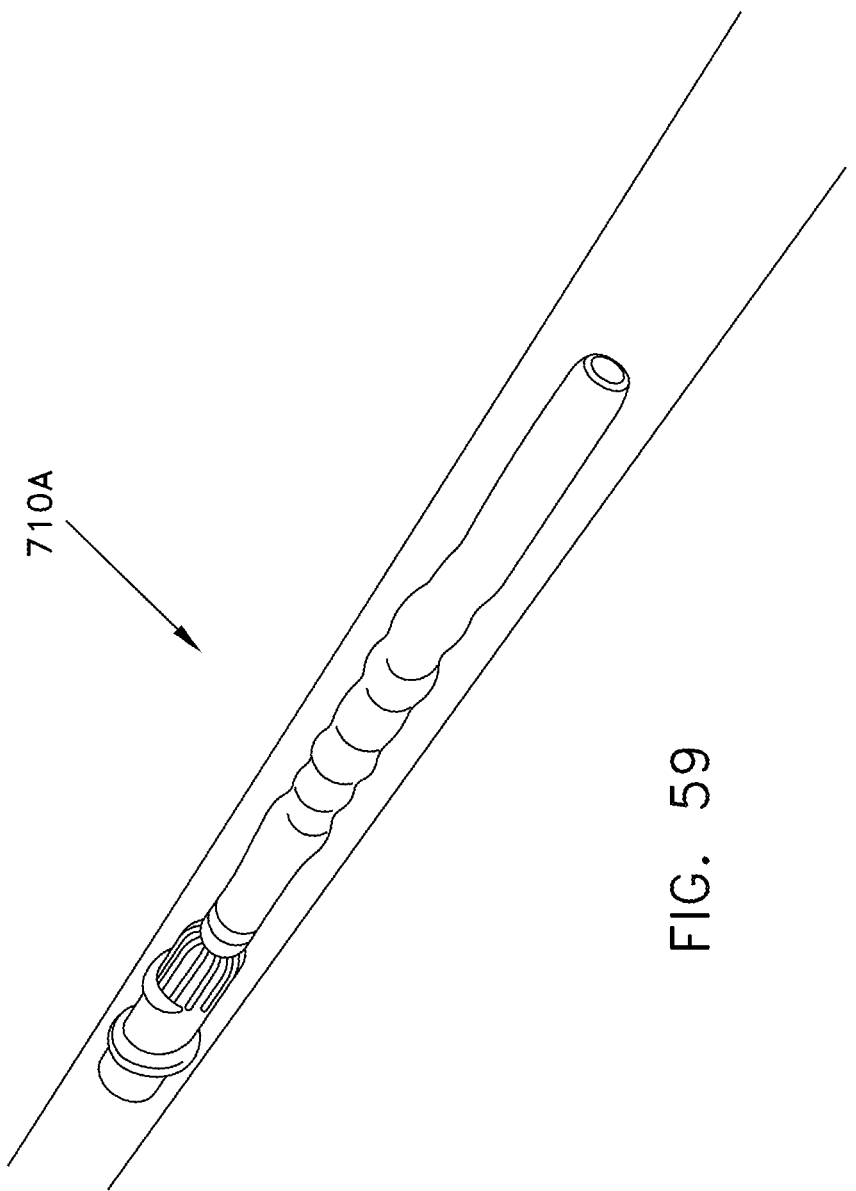
Figure 60:
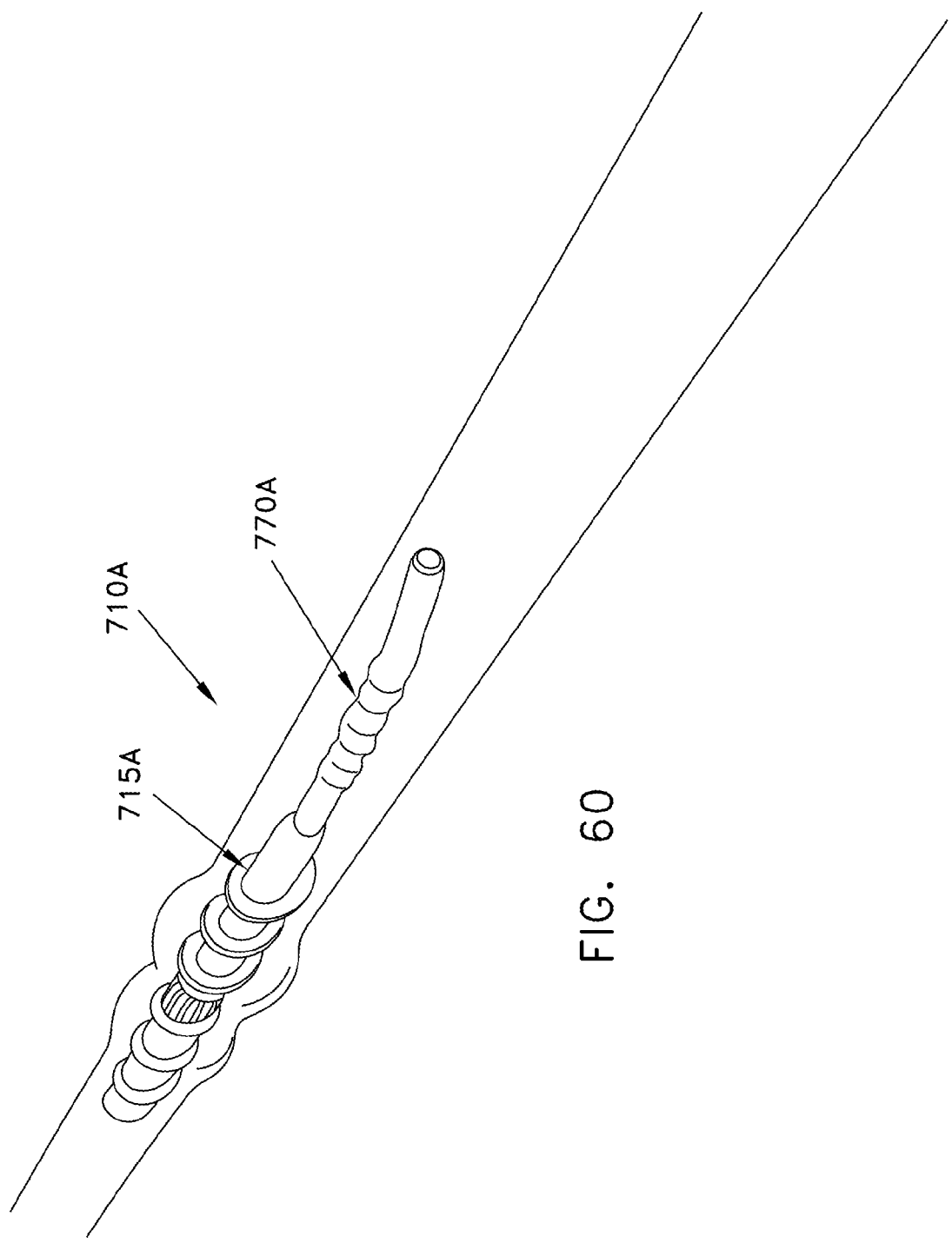
Figure 61:
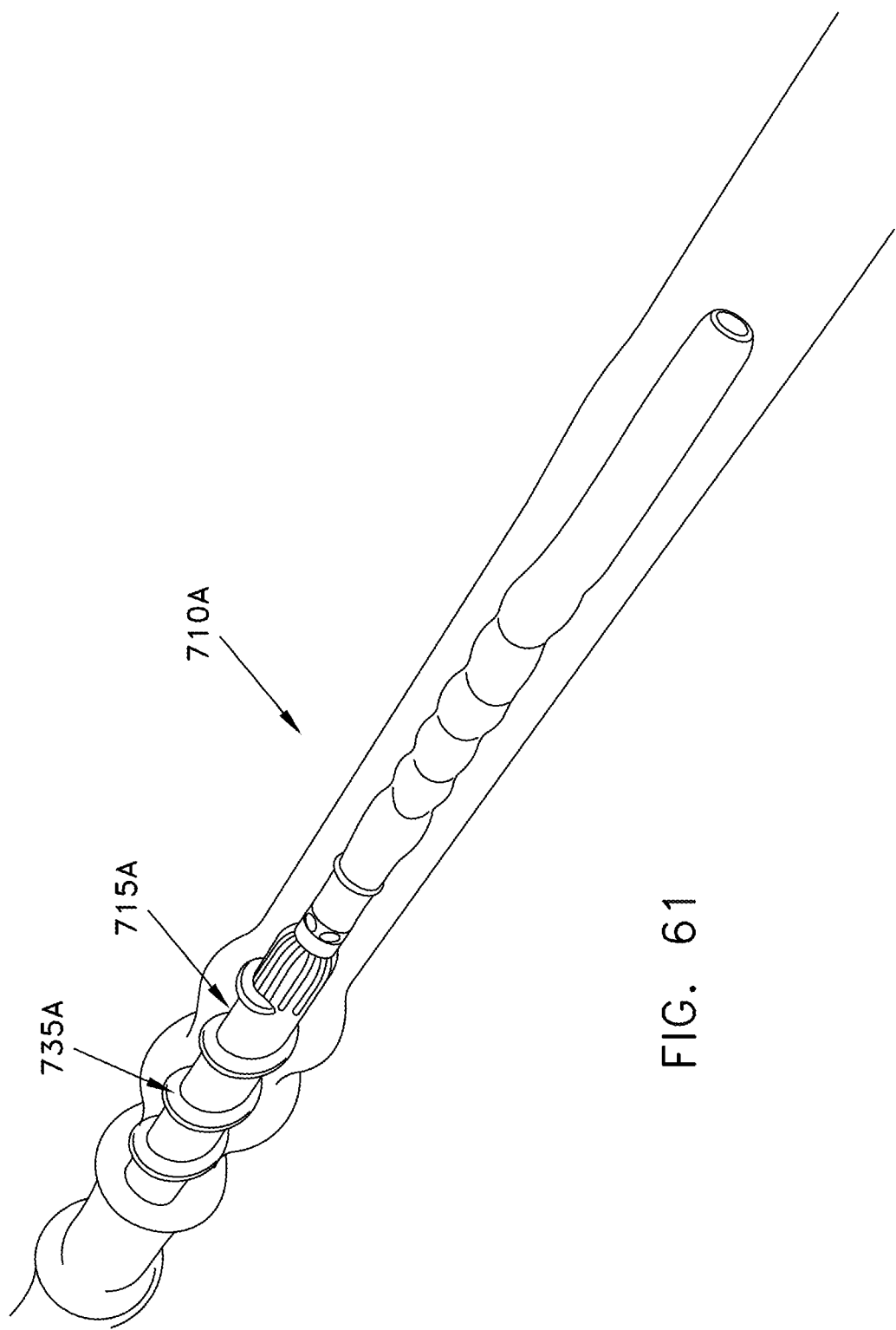
Figure 62:
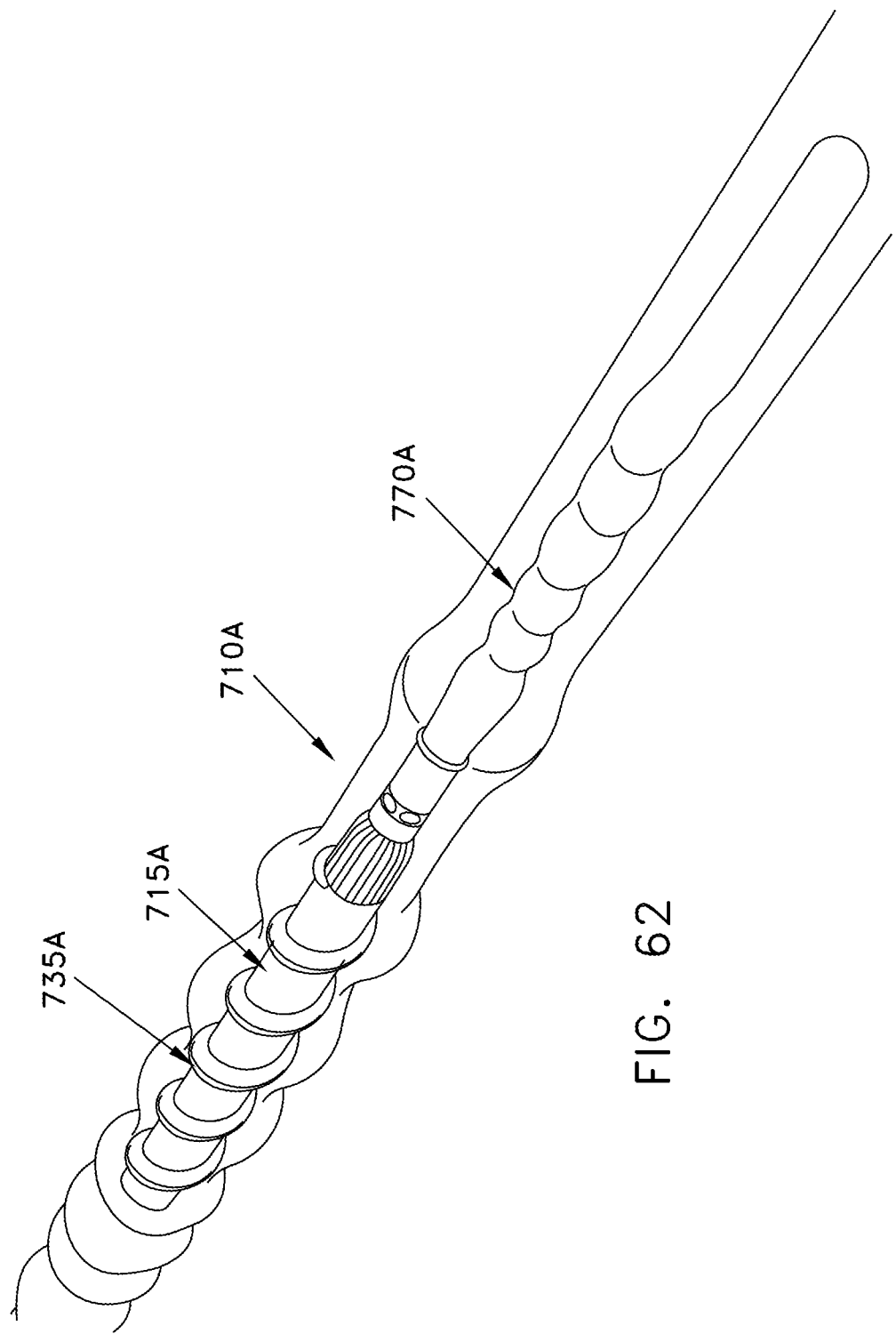

More particularly, the helical thread of camera introducer system 710A is preferably provided with a semi-ovoid cross-sectional thread profile, i.e., the "mailbox" shape shown in FIG. 57. Forming helical thread 735A with this semi-ovoid, "mailbox" shape allows for an easier and less traumatic advancement to, and through, the small bowel. It should be appreciated that helical thread 735A may also be provided with alternative profile geometries in order to optimize desired performance characteristics. By way of example but not limitation, camera introducer system 710A may be provided with (i) a helical thread having a non-symmetrical cross-section, or (ii) a helical thread having a profile which varies along the length of the helix, etc.

Furthermore, if desired, the helical thread may be formed so as to be partially deformable when engaging tissue, so as to provide a more compliant and less traumatic engagement with the tissue, e.g., during a rotate-to-advance procedure or during a rotate-to-pleat procedure. In other words, the helical thread may be constructed so that it will deform to some extent when it engages the tissue, whereby to form a more compliant and less traumatic engagement with the tissue. Of course, while the helical thread is partially deformable, it must still retain a sufficient structural integrity to advance the camera introducer system through the anatomy (in a rotate-to-advance procedure) or to pleat the small bowel tissue onto the corrugated tube (in a rotate-to-pleat procedure). By way of example but not limitation, this "partially deformable" thread characteristic may be provided by forming the helical thread with a hollow configuration. See FIG. 57.

In addition to the foregoing, and because camera introducer system 710A may be advanced using an antegrade approach rather than a retrograde approach, the proximal end of the camera introducer system is specially configured so as to be more appropriate for the application and less traumatic to the patient. More particularly, in order to reduce trauma to the patient's throat, the proximal end of camera introducer system may be fitted with an atraumatic jacket at the location where the proximal end of the camera introducer system will contact the throat during the procedure.

In use, in an antegrade small bowel procedure, camera introducer system 710A is advanced down the esophagus, through the stomach and into the small bowel. See FIGS. 56 and 58. Preferably this is done with endoscope 770A having been secured within the corrugated tube so that the distal end of the endoscope projects substantially beyond (e.g., by 6 inches or so) the distal end of the corrugated tube.

Once in the small bowel, and looking next at FIGS. 59-62, as the camera introducer system 710 is rotated and advanced, the small bowel tissue begins to gather on the exterior of helical threads 735A. The connective tissue, or mesentery, of the small bowel is very mobile and allows for the tissue to easily gather, and essentially "pleat", onto the shaft of the advancing camera introducer system 710A.

By gathering the pleated tissue of the small bowel onto the camera introducer system 710A, it is possible for the physician to more efficiently traverse the approximately 6 meters of small bowel, which would be impractical using traditional small bowel endoscope delivery systems.

Once the camera introducer system has been advanced to a desired location within the small bowel, or to the furthest accessible point within the small bowel, nut 755A can be unlocked by un-screwing it proximally. This opens collet fingers 745A, and hence elastomeric ring 765A, thereby releasing endoscope 770A from corrugated tube 715A. Endoscope 770A can thereafter be extended out of the corrugated tube 715A and advanced further into the small bowel. Providing camera introducer system 710A with this extendable endoscope feature can be particularly advantageous in difficult to traverse cavities such as the small bowel.

It should be appreciated that camera introducer system 710A significantly shortens the length of time required for the physician to access and traverse the small bowel. By having the small bowel tissue gather in a pleating fashion along helical threads 735A, the surgeon is able to advance the apparatus through the small bowel in less than half the time required by traditional devices and methods. This is significant as shortening procedure time (i) reduces the length of time that the delicate small bowel tissue is pleated on itself (and hence subject to damage or necrosis), (ii) reduces the total length of time that the patient needs to be under anesthesia, and (iii) allows physicians to perform more of these procedures for other patients in need.

Figure 63:
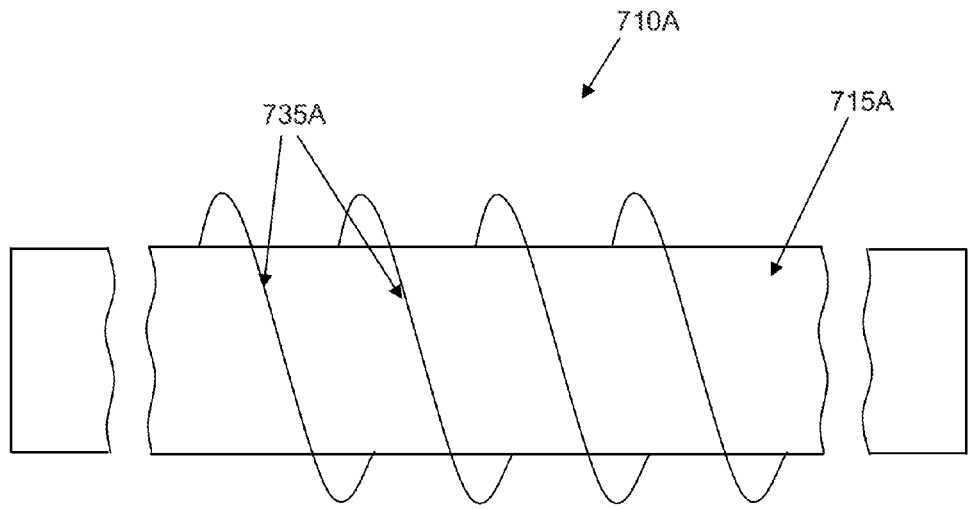

Threaded Camera Introducer System with Powered Helical Drive Located Intermediate the Length of the Camera Introducer System In the foregoing description, the rotate-to-advance catheterization system generally comprises an elongated tube having helical threads disposed thereon, wherein substantially the entire length of the tube is rotated in order to effect the desired rotate-to-advance action. By way of example but not limitation, and looking now at FIG. 63, threaded camera introducer system 710A generally comprises a tube 715A having helical threads 735A disposed thereon, wherein substantially the entire length of tube 715A is rotated in order to effect the desired rotate-to-advance action.

Figure 64:
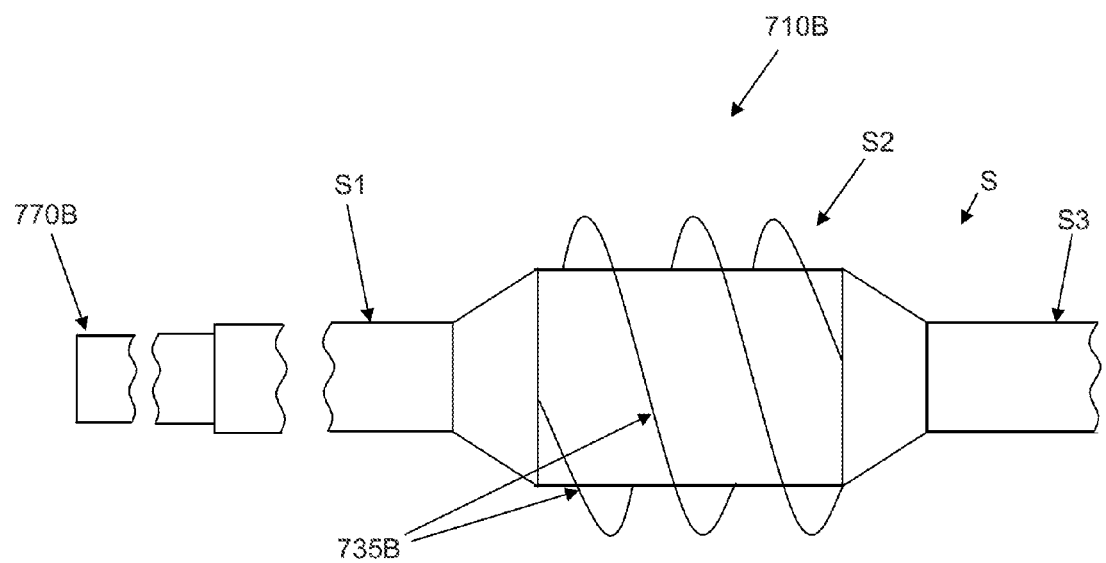
Figure 66:
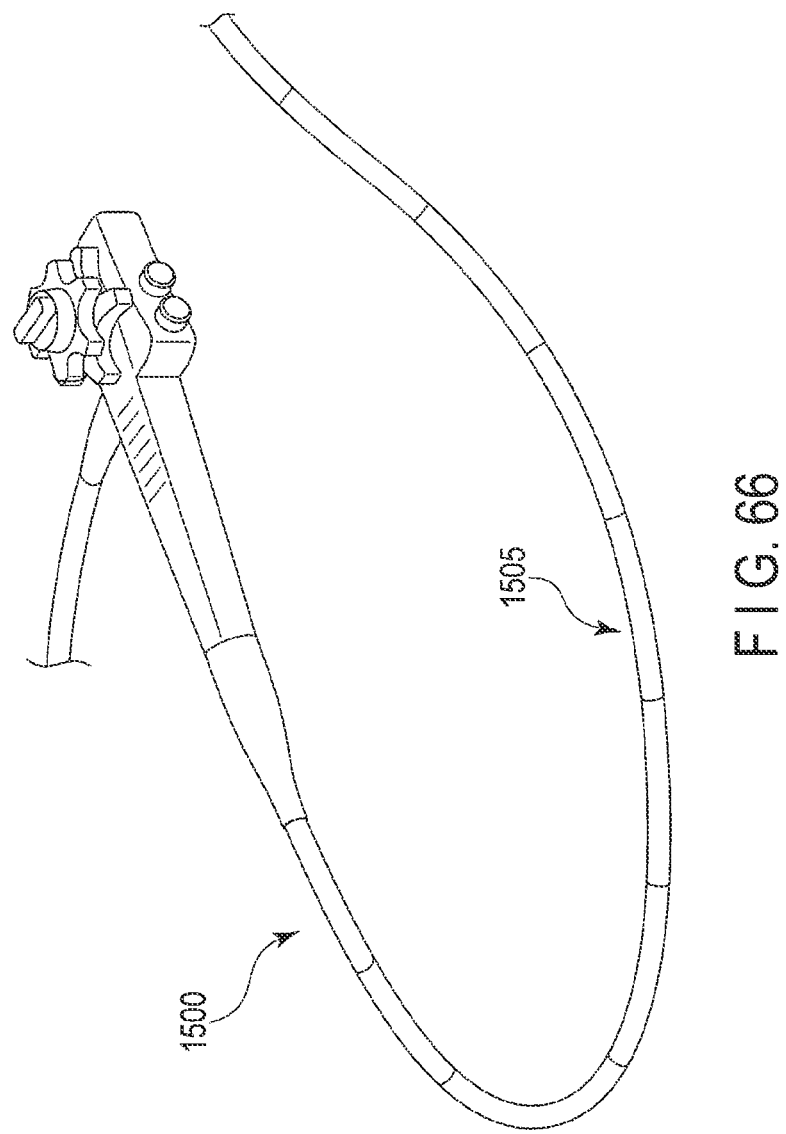
Figure 67:
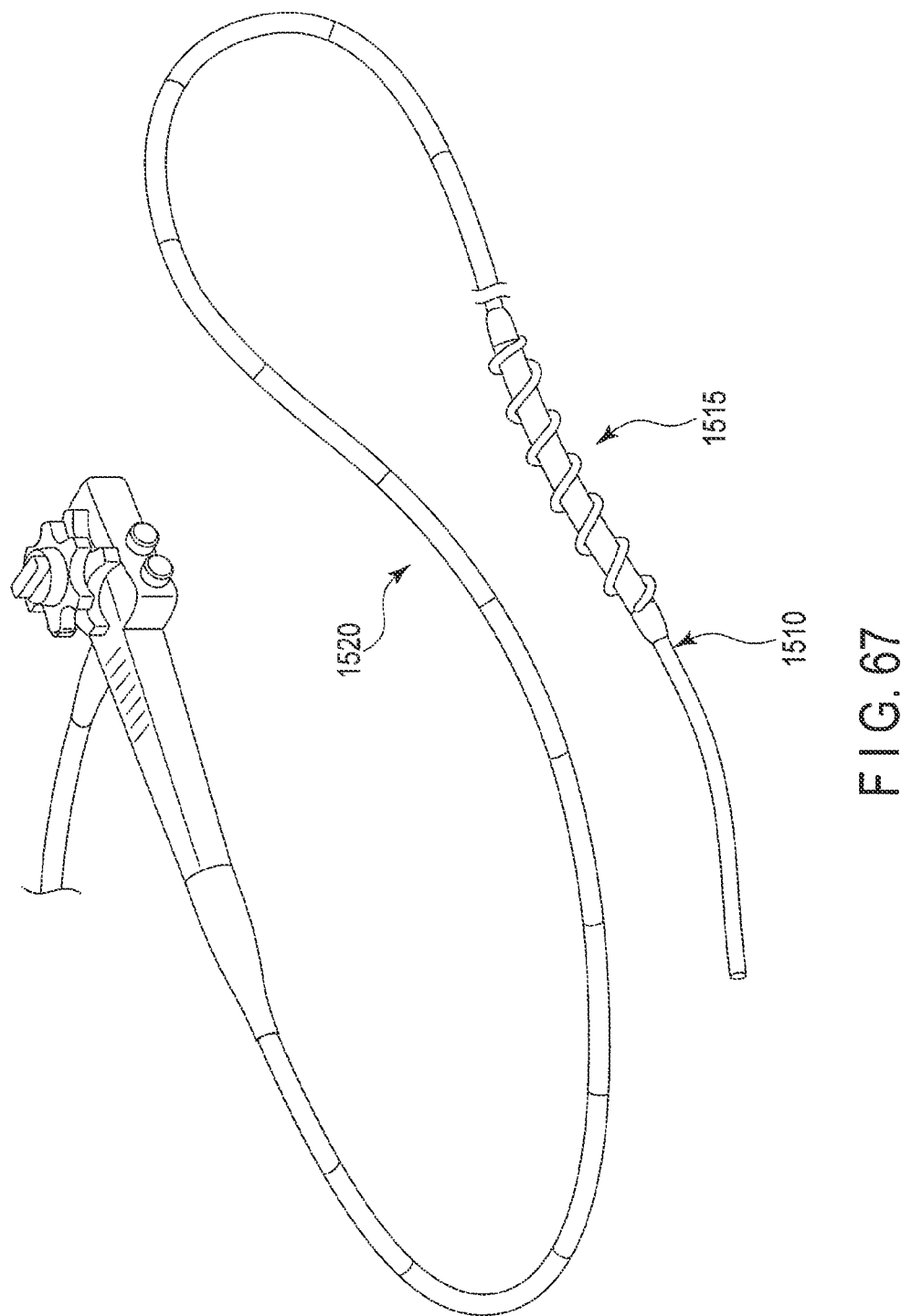
Figure 68:
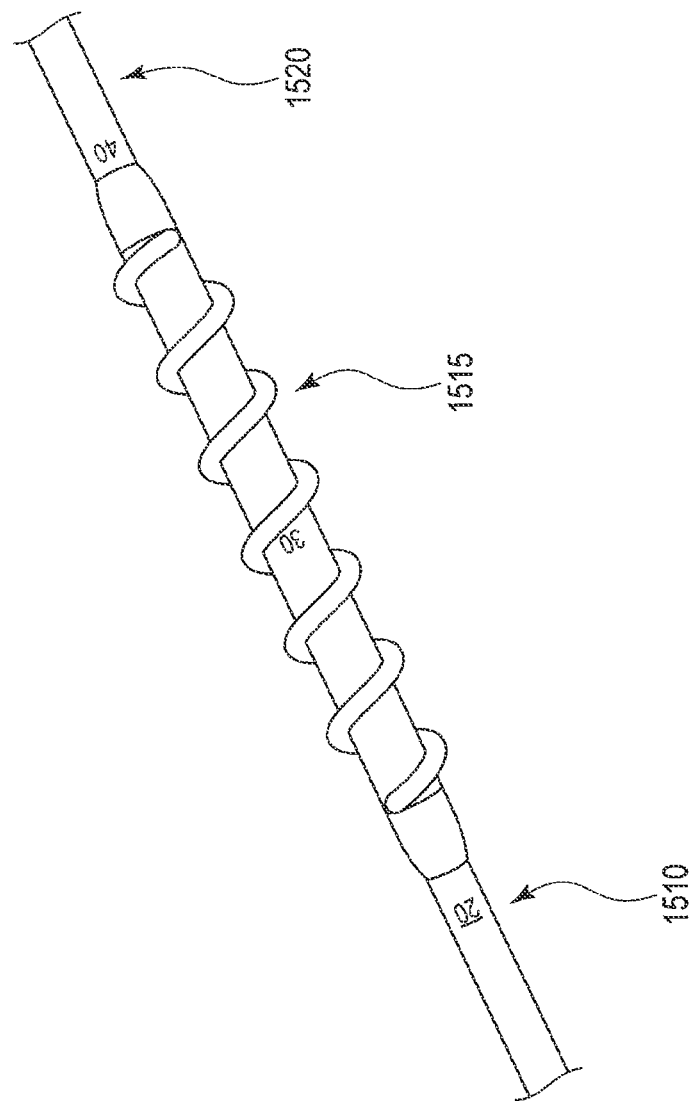
Figure 69:
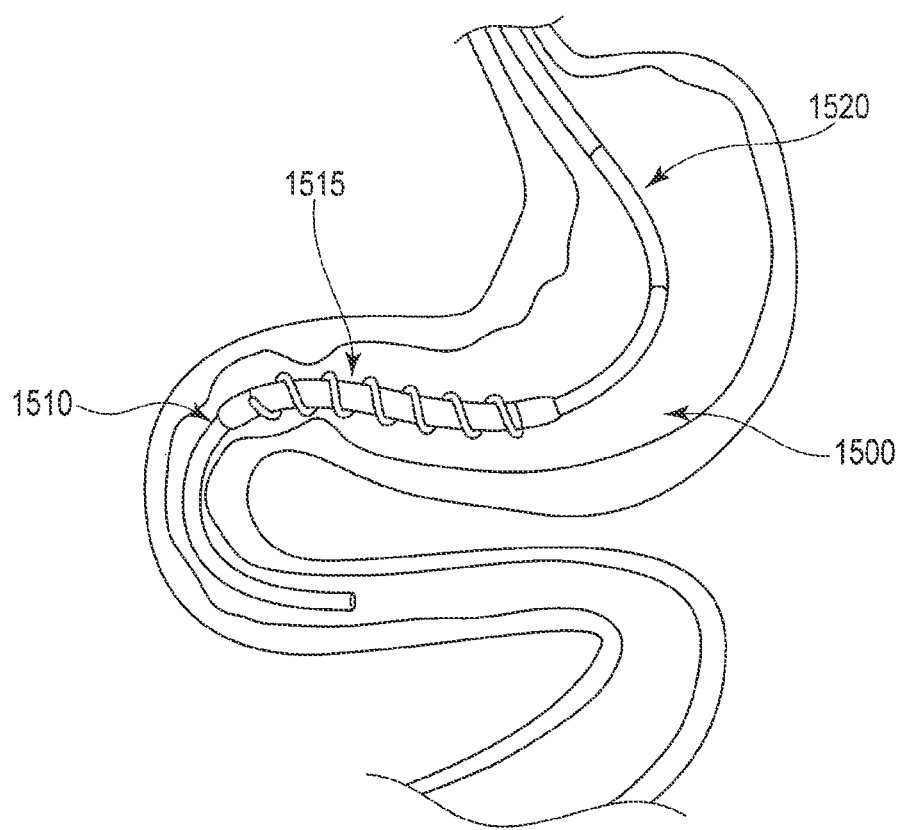
Figure 72:
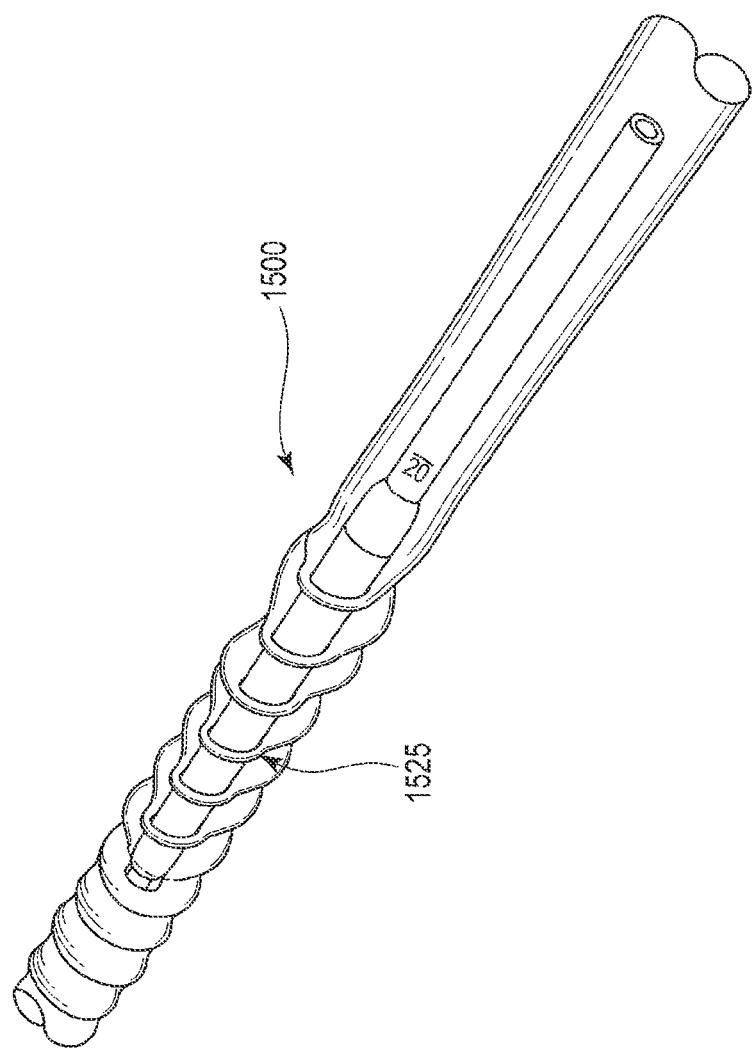
Figure 73:
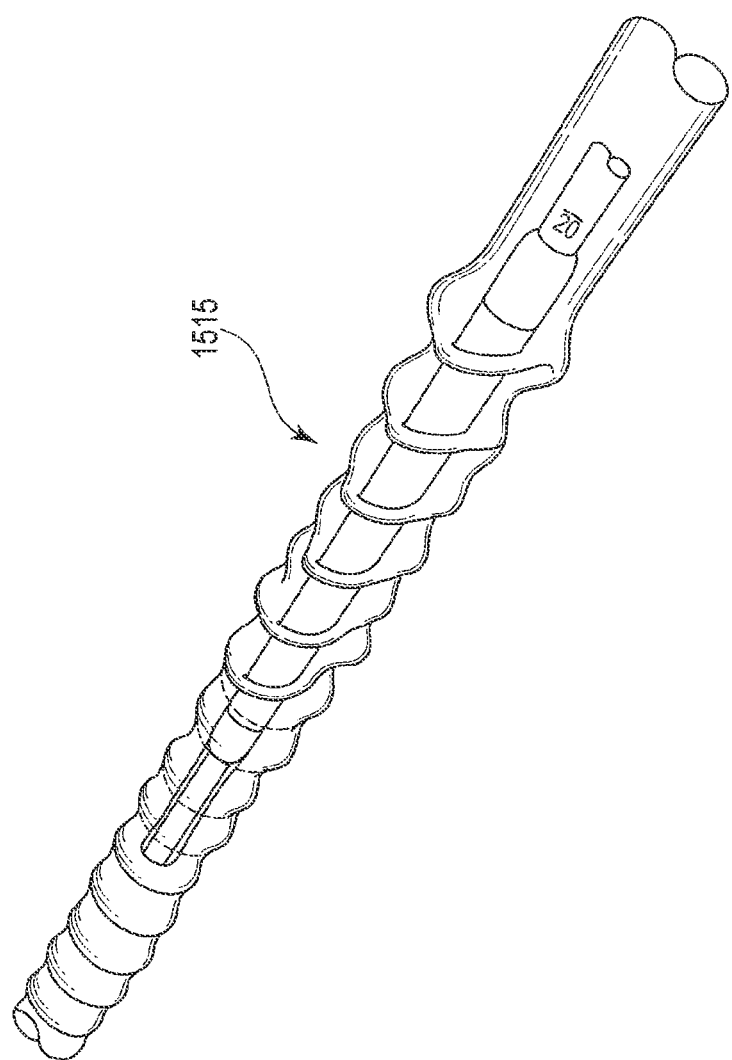

In another form of the present invention, and looking next at FIG. 64, there is shown a novel threaded camera introducer system 710B which is generally similar to threaded camera introducer system 710A discussed above, except that it is formed with a powered helical drive located intermediate the length of the threaded camera introducer system.

More particularly, in this form of the present invention, novel threaded camera introducer system 710B comprises a shaft S which preferably comprises three zones: a non-rotating distal zone 51, a rotatable intermediate zone S2, and a non-rotating proximal zone S3. An endoscope 770B preferably extends some distance beyond the distal end of non-rotating distal zone 51, in the manner shown in FIG. 64. Rotatable intermediate zone S2 carries helical thread 735B. Power for rotating rotatable intermediate zone S2 is transmitted from the proximal end of threaded camera introducer system 710B, through non-rotating proximal zone S3, to rotatable intermediate zone S2. By way of example but not limitation, power may be transmitted to rotatable intermediate zone S2 via a hollow rotatable tube disposed co-axial with, and in-board of, non-rotating proximal zone S3. Alternatively, and as discussed above, power may be transmitted to rotatable intermediate zone S2 by a variety of sources located anywhere along the length of the catheterization system.

In use, threaded camera introducer system 710B is advanced to the small bowel (or other bodily passageway) in the same way as threaded camera introducer system 710A. Once threaded camera introducer system 710B is advanced into the small bowel (or other bodily passageway), rotatable intermediate zone S2 is rotated so as to cause helical threads 735B to gather, and pleat, small bowel (or other bodily passageway) tissue over non-rotating proximal zone S3. When it is desired to un-pleat the gathered small bowel (or other bodily passageway) tissue from non-rotating proximal zone S3, rotatable intermediate zone S2 may simply be rotated with the opposite rotation.

If desired, non-rotating distal zone S1 may be formed so as to be relatively short, and non-rotating proximal zone S3 may be formed so as to relatively long.

Or, if desired, non-rotating distal zone S1 may be omitted altogether, in which case shaft S comprises only two zones, a rotatable distal zone and a non-rotating proximal zone.

If desired, a torque limiter may also be provided so as to safeguard the tissue.

Furthermore, if desired, more than one rotatable intermediate zone S2 can be provided along the length of the shaft, preferably separated by zones of non-rotatable shaft. And, if desired, combinations of left-hand and right-hand rotation of rotatable intermediate zone S2 can be provided along the length of the shaft for selectively engaging different regions of tissue, e.g., one rotatable zone may be configured to engage the large bowel and another rotatable zone may be configured to engage the small bowel. Where multiple rotatable intermediate zones S2 are provided, it is important to note that each zone may be operated at the same time as the remaining rotatable intermediate zones S2, or each of the multiple rotatable intermediate zones S2 may be rotated independently of one another. By way of example but not limitation, two separately-operable rotatable intermediate zones S2 may be provided along the length of the shaft, with the proximalmost rotatable intermediate zone S2 configured to engage the large bowel so as to advance the shaft along the large bowel and with the distalmost rotatable intermediate zone S2 configured to engage the small bowel so as to plicate the small bowel onto the shaft.

As discussed above, once threaded camera introducer system 710B is advanced into the small bowel (or other bodily passageway), rotatable intermediate zone S2 is rotated so as to cause helical threads 735B to gather, and pleat, small bowel (or other bodily passageway) tissue over non-rotating proximal zone S3. In contrast, as a traditional one piece threaded camera introducer system (e.g., FIG. 63) is advanced through the small bowel (or other bodily passageway), the entire length of the threaded camera introducer is rotated, thereby causing the helical threads to gather, and pleat, small bowel (or other bodily passageway) tissue over the entire length of the threaded camera introducer. Because the entire length of the threaded camera introducer is rotating, friction can build between the threaded camera introducer system and the plicated tissue as more and more tissue is plicated onto the threaded camera introducer system. This friction can eventually limit how much of the small bowel (or other bodily passageway) tissue can be plicated onto the threaded camera introducer system and can make it increasingly difficult to navigate, and advance through, the tortuous paths of the small bowel (or other bodily passageway). By constructing threaded camera introducer system with rotatable intermediate zone S2 and non-rotating distal zone S1 and non-rotating proximal zone S3, the small bowel (or other bodily passageway) may be gathered onto non-rotating proximal zone S3 as the threaded camera introducer system is advanced without progressively increasing friction between the tissue and the non-rotating proximal zone S3 which receives that tissue.

It should also be appreciated that the foregoing construction can be integrated into the design of the endoscope itself. More particularly, and looking now at FIGS. 65-73, there is shown a novel endoscope 1500 which comprises an elongated shaft 1505. Elongated shaft 1505 in turn comprises three zones: a non-rotating distal zone 1510, a rotatable intermediate zone 1515 and a non-rotating proximal zone 1520. Rotatable intermediate zone 1515 carries helical threads 1525. Power for rotating rotatable intermediate zone 1515 is transmitted from the proximal end of endoscope 1500, through non-rotating proximal zone 1520, to rotatable intermediate zone 1515. By way of example but not limitation, power may be transmitted to rotatable intermediate zone 1515 via a hollow rotatable tube disposed co-axial with, and in-board of, non-rotating proximal zone 1520. Alternatively, and as discussed above, power may be transmitted to rotatable intermediate zone 1515 by a variety of sources located anywhere along the length of the catheterization system.

Figure 74:
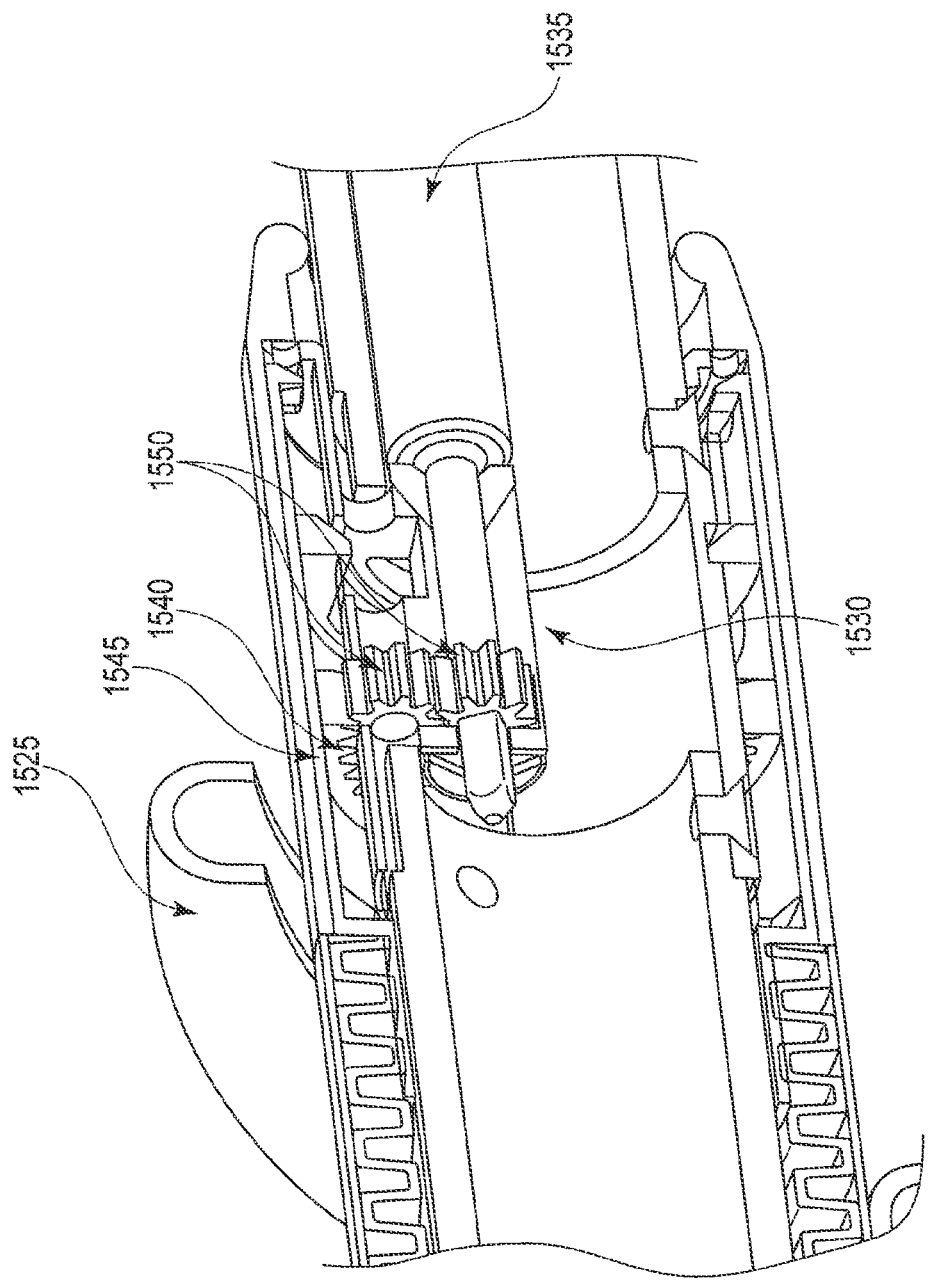
Figure 76:
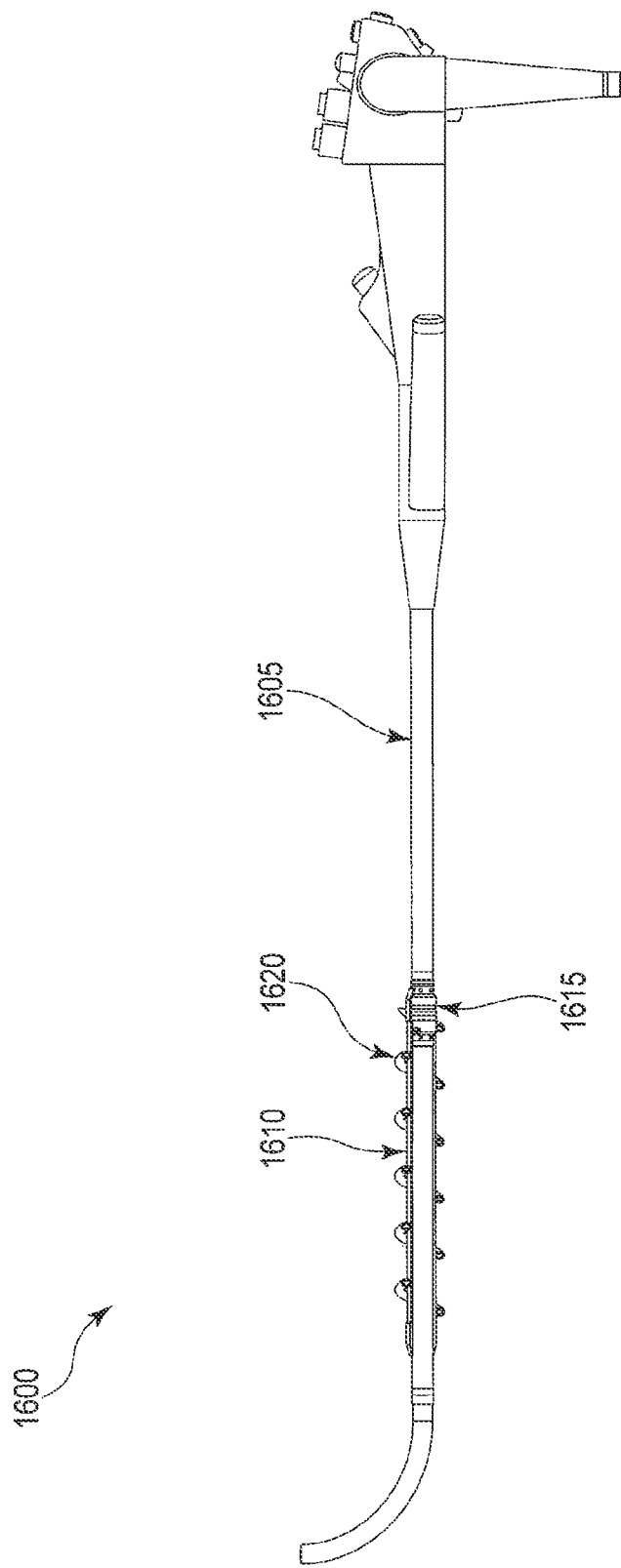
FIG. 76 is a view like that of FIG. 75, except with selected portions of the view being shown in section.
Figure 77:
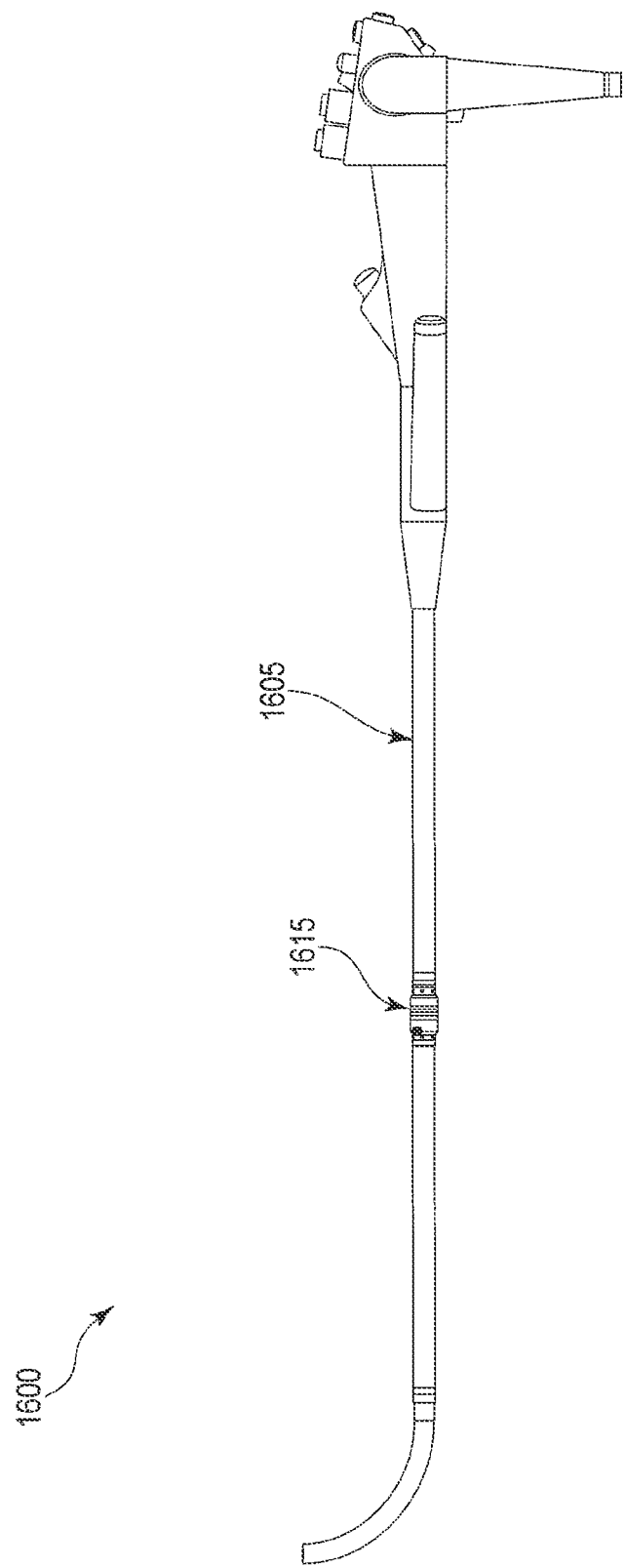
FIG. 77 is a schematic view showing the endoscope of the novel visualization system of FIG. 75.
Figure 83:
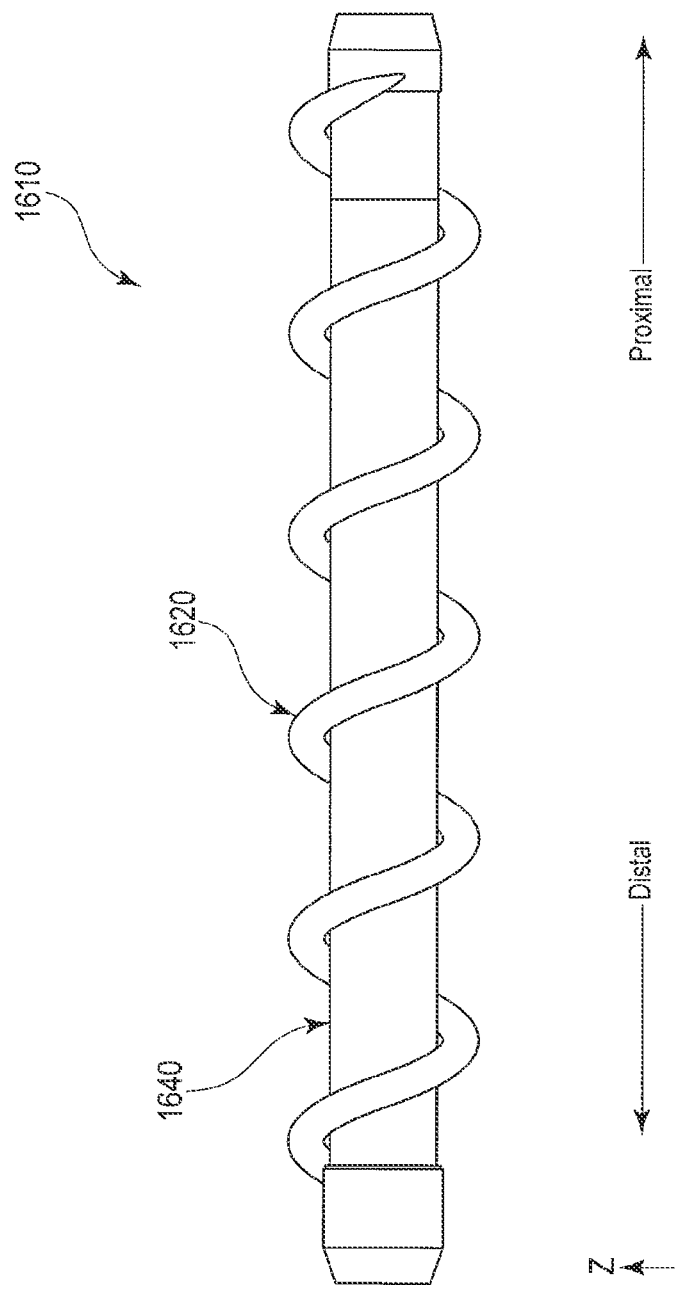
FIG. 83 is a schematic view showing the disposable drive tube of the novel visualization system of FIG. 75.
Figure 84:
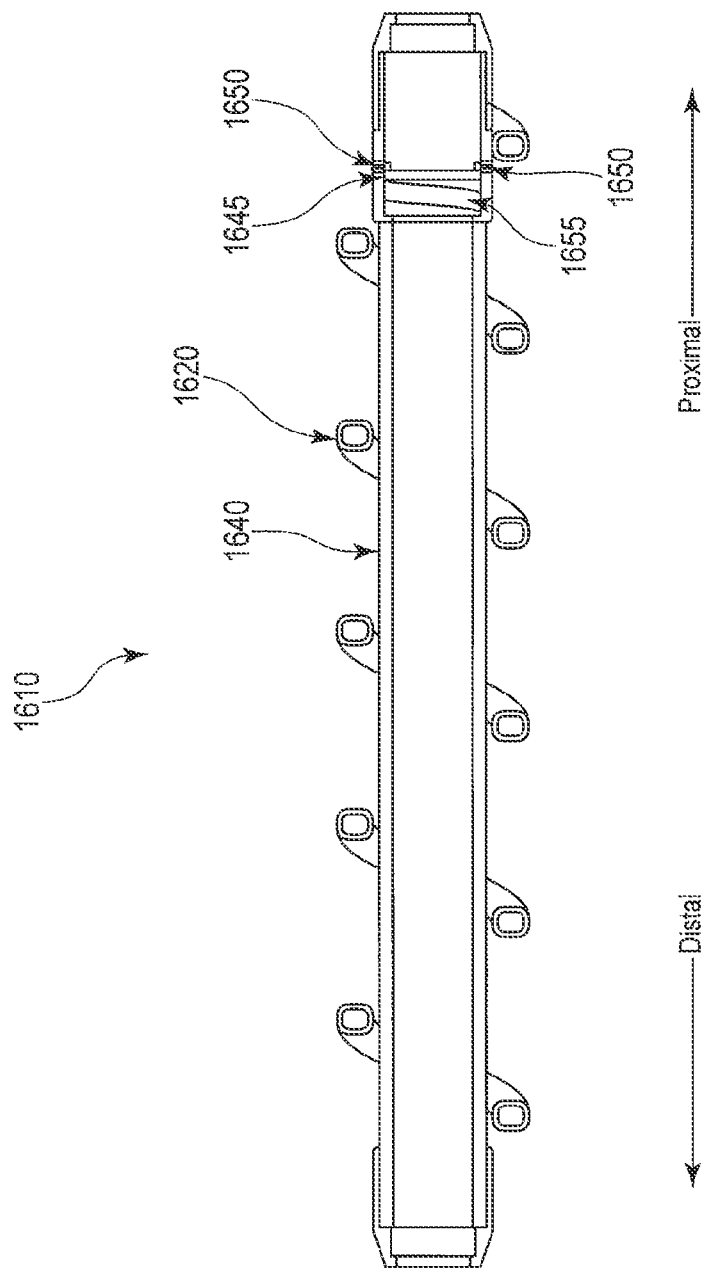
FIG. 84 is a partial sectional view of the disposable drive tube shown in FIG. 83.
Figure 85:
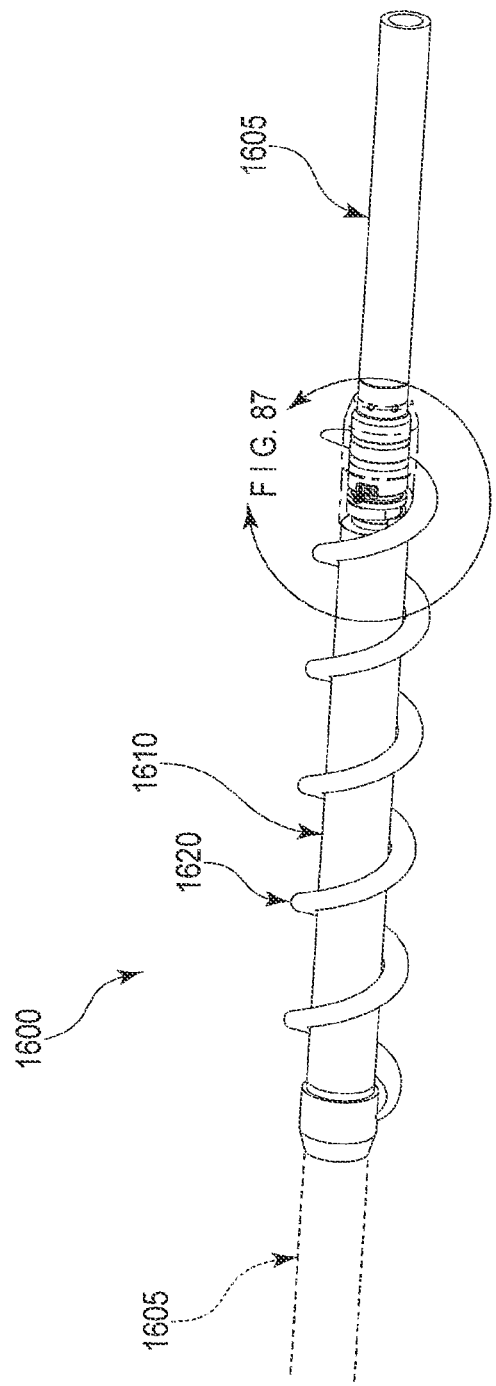
FIG. 85 is an enlarged view of a portion of the novel visualization system of FIG. 75.
Figure 86:
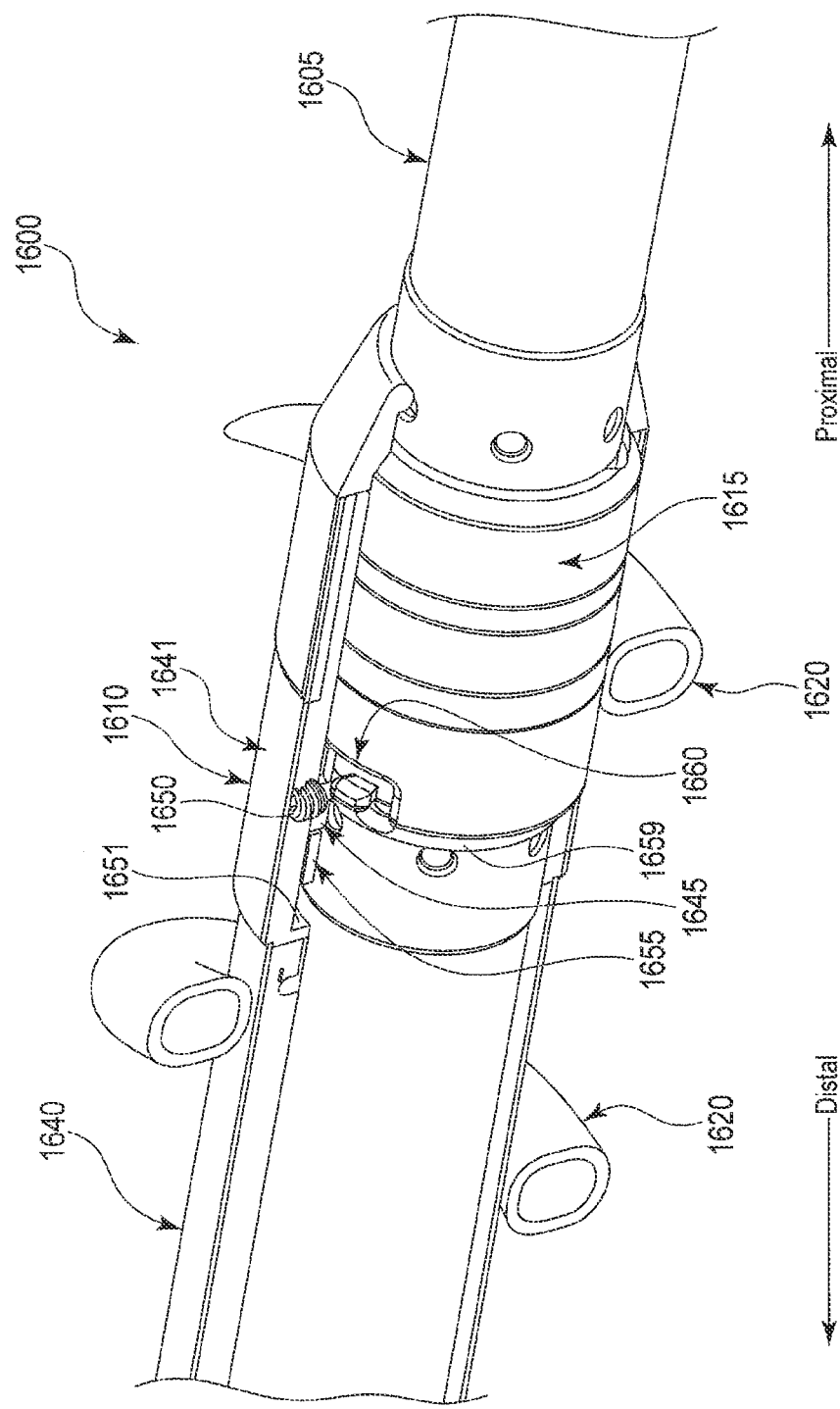
FIGS. 86 and 87 are schematic views showing a bayonet mount used to releasably secure the disposable drive tube to the endoscope.
Figure 87:
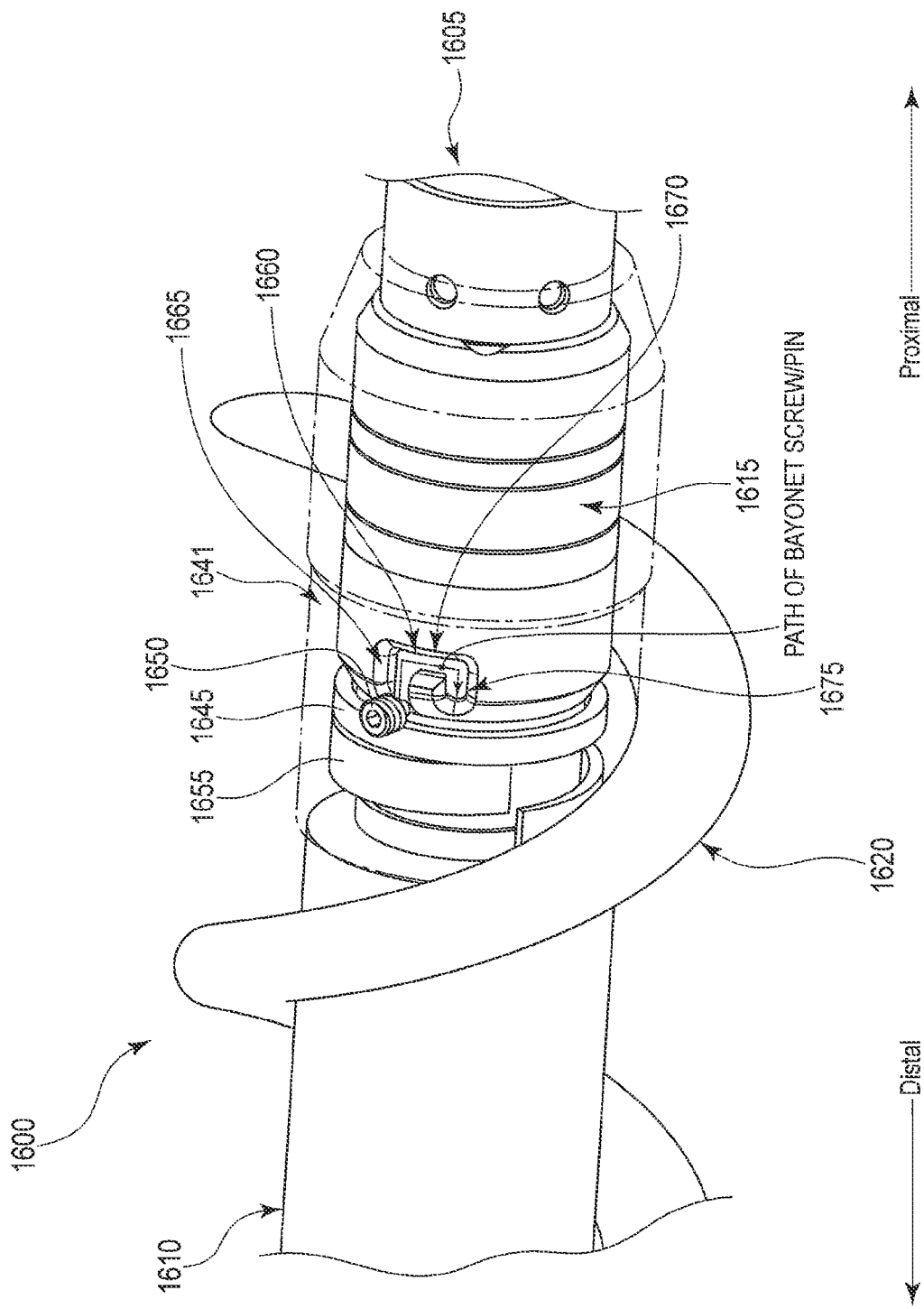

In one preferred form of the present invention, and looking now at FIG. 74, it will be seen that a geared drive shaft assembly 1530 may be used to turn rotatable intermediate zone 1515. More particularly, geared drive shaft assembly 1530 generally comprises a flexible drive shaft 1535 for delivering rotational motion to the distal end of proximal non-rotating zone 1520, a circumferential gear 1540 secured to the inner surface of a jacket 1545 which carries helical threads 1525 thereon, and a pair of transmission gears 1550 for transferring motion between flexible drive shaft 1535 and circumferential gear 1540. As a result of this construction, rotation of flexible drive shaft 1535 rotates jacket 1545, which in turn rotates helical threads 1525.

In practice, it may be found that when endoscope 1500 is passed a substantial length along a tortuous bodily passageway, so that the elongated shaft 1505 of the endoscope must traverse numerous twists and turns, it may be desirable or necessary to provide a spline connection along flexible drive shaft 1535 so as to accommodate changes of cable length due to bending of the endoscope.

In use, endoscope 1500 is advanced to the small bowel (or other bodily passageway) in the same way as threaded camera introducer system 710A. Once endoscope 1500 is advanced into the small bowel (or other bodily passageway), rotatable intermediate zone 1515 is rotated so as to cause helical threads 1525 to gather, and pleat, small bowel (or other bodily passageway) tissue over non-rotating proximal zone 1520. When it is desired to un-pleat the gathered small bowel (or other bodily passageway) tissue from non-rotating proximal zone 1520, rotatable intermediate zone 1515 may simply be rotated with the opposite rotation.

Again, if desired, non-rotating distal zone 1510 may be omitted altogether, in which case shaft 1505 comprises only two zones, a rotatable distal zone 1515 and a non-rotating proximal zone 1520.

In one preferred form of the present invention, and looking now at FIGS. 75-87, there is provided a novel visualization system 1600 formed in accordance with the present invention. Novel visualization system 1600 may be used to examine, diagnose and/or treat tissue located within, or accessed via, a bodily passageway, e.g., the large bowel, the small bowel, etc. Novel visualization system 1600 is believed to have particular application to examining, diagnosing and/or treating tissue located within, or accessed via, the small bowel, with the small bowel being plicated and/or pleated upon the outer surface of the novel visualization system so as to facilitate access to deep distal sites.

Still looking now at FIGS. 75-87, novel visualization system 1600 generally comprises an endoscope 1605 and a disposable drive tube 1610. More particularly, endoscope 1605 comprises a rotatable drive collar 1615, and disposable drive tube 1610 comprises one or more helical threads 1620, with disposable drive tube 1610 being removably attachable to rotatable drive collar 1615, whereby endoscope 1605 can cause disposable drive tube 1610 to rotate so that helical threads 1620 cause relative movement between passageway tissue and the endoscope. In this way, endoscope 1605 can access tissue at deep distal sites.

More particularly, endoscope 1605 includes a flexible drive shaft 1625 for delivering rotary motion to the distal end of the drive tube. A pair of transmission gears 1630, 1635 transfer motion between flexible drive shaft 1625 and rotatable drive collar 1615. As a result of this construction, rotatable drive collar 1615 can be rotatably driven, either clockwise or counterclockwise, by applying appropriate rotary motion to the proximal end of flexible drive shaft 1625.

Disposable drive tube 1610 comprises an elongated tube 1640 having one or more helical threads 1620 disposed on its outer surface. Helical threads 1620 are of the sort previously disclosed, i.e., when helical threads 1620 engage the interior wall of a bodily passageway (e.g., the small bowel, the large bowel, etc.), rotary motion of helical threads 1620 will cause relative movement between passageway tissue and the drive tube (and hence the endoscope). In this way, rotation of disposable drive tube 1610 can cause advancement or withdrawal of endoscope 1605 along the bodily passageway, and/or movement of passageway tissue along the endoscope (so as to plicate and/or pleat the tissue onto the endoscope).

Disposable drive tube 1610 is intended to be releasably mounted to rotatable drive collar 1615 of endoscope 1605. In one preferred form of the present invention, disposable drive tube 1610 is releasably mounted to rotatable drive collar 1615 by a bayonet mount. More particularly, in this form of the present invention, disposable drive tube 1610 includes an extension 1641 having a radially-extending pin 1650 mounted thereto. A shoulder 1651 is formed distal to the radially-extending pin 1650. A compression spring 1655 biases a ring 1645 proximally, away from shoulder 1651. Correspondingly, rotatable drive collar 1615 comprises a shoulder 1659 for opposing ring 1645, and a C-shaped slot 1660 for receiving pin 1650. More particularly, C-shaped slot 1660 comprises a first proximally-extending section 1665, a second circumferentially-extending section 1670, and a third distally-extending section 1675. In view of this construction, when disposable drive tube 1610 is to be mounted to rotatable drive collar 1615, the proximal end of disposable drive tube 1610 is slipped over the distal end of endoscope 1605 and moved proximally until radially-extending pin 1650 engages shoulder 1659. Then, with proximally-directed pressure being applied to disposable drive tube 1610, the disposable drive tube is rotated circumferentially until pin 1650 slips into the first proximally-extending section 1665 of C-shaped slot 1660 and ring 1645 engages shoulder 1659. Then more proximally-directed pressure is applied so that the power of compression spring 1655 is overcome and radially-extending pin 1650 moves along first proximally-extending section 1665 of C-shaped slot 1660. Then, while maintaining proximal pressure, disposable drive tube 1610 is rotated circumferentially so that pin 1650 moves along second circumferentially-extending section 1670 and is aligned with third distally-extending section 1675. Then proximal pressure on disposable drive tube 1610 is relaxed so that compression spring 1655 moves disposable drive tube 1610 distally so that pin 1650 moves down third, distally-extending section 1675, whereby to secure disposable drive tube 1610 to rotatable drive collar 1615.

Disposable drive tube 1610 may be removed from endoscope 1605 in a corresponding manner, i.e., by pushing disposable drive tube 1610 proximally, rotating disposable drive tube 1610 circumferentially, and releasing the proximal pressure on disposable drive tube 1610 so that pin 1650 exits C-shaped slot 1660.

If desired, a pair of diametrically-opposed pins 1650, and a corresponding pair of diametrically-opposed C-shaped slots 1660, can be provided so as to create a more secure bayonet mount.

In use, a disposable drive tube 1610 is mounted to endoscope 1605, the endoscope is introduced into a bodily passageway, flexible drive shaft 1625 is turned in a first direction so as to turn rotatable drive collar 1615 and hence disposable drive tube 1610. As a result, relative movement will be produced between the passageway tissue and the disposable drive tube (and hence the endoscope), i.e., advancement (or withdrawal) of the endoscope 1605 along the bodily passageway, and/or movement of the passageway tissue onto (or off of) the endoscope. When the distal end of endoscope 1605 has accessed the remote site, the endoscope may be used in ways well known in the art to examine, diagnose and/or treat tissue located within, or accessed via, the bodily passageway. Thereafter, the endoscope may be withdrawn from the remote site by rotating flexible drive shaft 1625 in a second, opposite direction. After the apparatus has been withdrawn from the body, disposable drive tube 1610 may be dismounted from endoscope 1605 and discarded.

Figure 88:
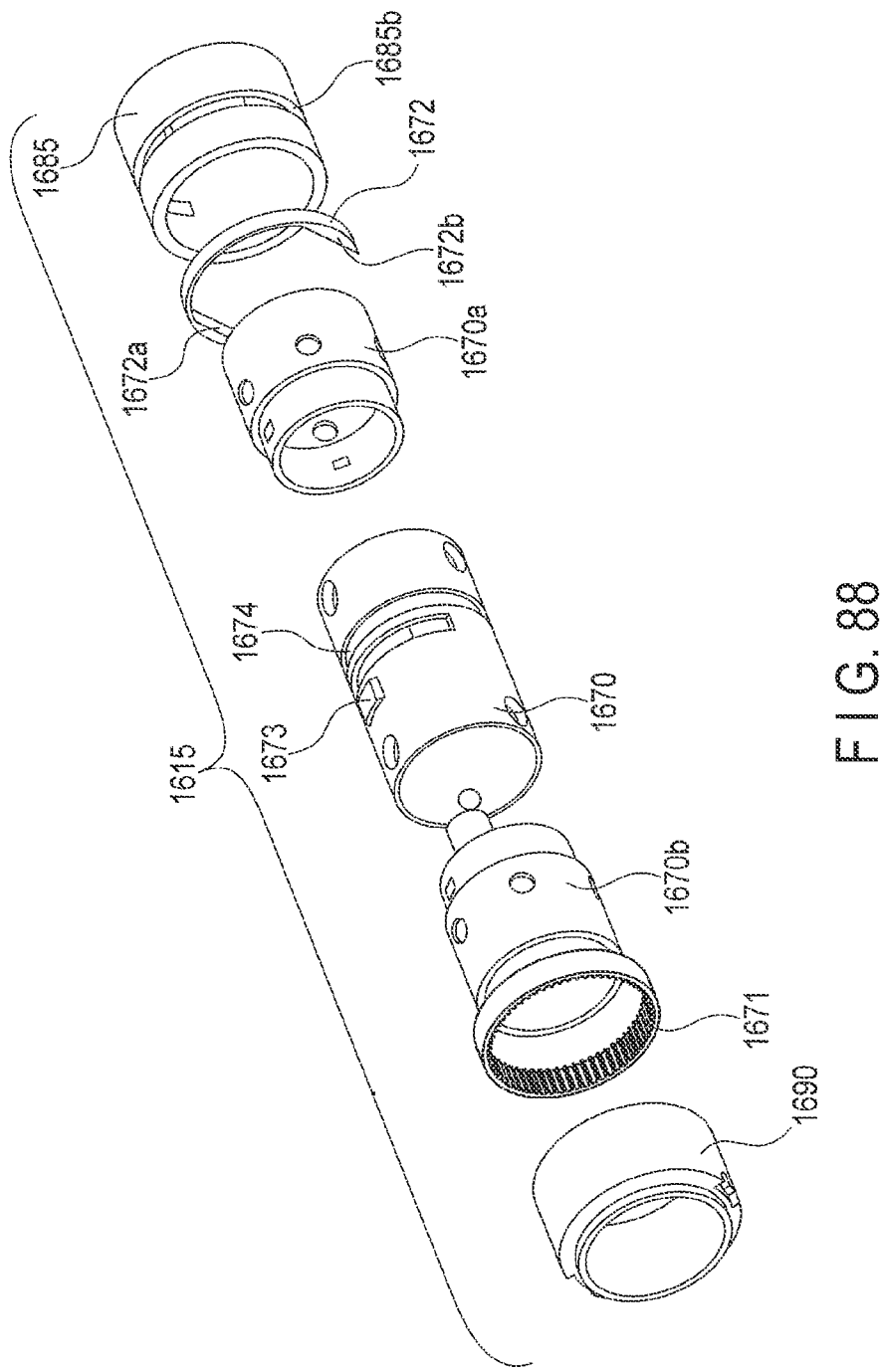
FIG. 88 is an exploded view of the rotatable drive collar of the visualization system of FIG. 75.

FIGS. 88 and 89 further illustrate the rotatable drive collar 1615. The rotatable drive collar 1615 comprises a stator 1670, a rotary gear 1671, and a C-shaped ring 1672. The C-shaped ring 1672 restrains axial movement of the stator 1670 and the rotatable components of the rotatable drive collar 1615 relative to each other. The stator 1670 has slots 1673, 1674. The rotary gear 1671 is engaged with intermediate gear 1635 via the slot 1673, and the C-shaped ring 1672 is engaged with and received in the slot 1674.

The rotatable drive collar 1615 includes a proximal rotor tube 1685 and a distal rotor tube 1690. In the assembled state of the rotatable drive collar 1615, the proximal rotor tube 1685, the rotary gear 1671, and the distal rotor tube 1690 are joined such that the proximal rotor tube 1685, the rotary gear 1671, and the distal rotor tube 1690 are axially aligned with respect to each other and restrained from rotating with respect to each other, such that rotation of the rotary gear 1671 causes corresponding rotation of the proximal and distal rotor tubes 1690. Further, the proximal rotor tube 1685, the rotary gear 1671, and the distal rotor tube 1690 are axially constrained with respect to each other. In this regard, the proximal rotor tube 1685, the rotary gear 1671, and the distal rotor tube 1690 may be joined in any suitable manner, e.g., welding, adhesive and/or thermal bonding, positive stops, and/or mechanical fasteners. Although the proximal rotor tube 1685, the rotary gear 1671, and the distal rotor tube 1690 are formed as separate elements, it should be understood that any or all of these elements may be integrally formed with each other, e.g., as a single monolithic structure.

The proximal rotor tube 1685, the rotary gear 1671, and the distal rotor tube 1690 in their joined state form a rotor assembly, that is axially constrained with respect to the stator 1670 via the C-shaped ring 1672.

The stator 1670 is non-rotatably attached to proximal and distal endoscope tube connectors 1670*a*, 1670*b* to form a stator assembly. The aforementioned rotor assembly is axially slid over the stator assembly, e.g., in the proximal direction, until the rotary gear 1671 engages the gear 1635. The generally cylindrical inner surface of the rotor assembly communicates with the generally cylindrical outer surface of stator assembly with a clearance sufficient to allow rotation therebetween. In this regard, the interface between the inner surface of the rotor assembly and the outer surface of the stator assembly may act in the manner of a bushing and/or a bearing or other mechanism may be provided to facilitate the relative rotatability between the stator assembly and the rotor assembly.

To allow for optimal engagement with the teeth of the transmission gear 1635, the inner gear diameter is the same or substantially the same as the diameter of the cylindrical inner surface of the rotor assembly. Further, this arrangement allows the gear teeth of the rotary gear 1671 to slide over the outer surface of the stator assembly during assembly. However, in order to engage the interior gear teeth of the rotary gear 1671, the teeth of transmission gear 1635 extend radially outwardly beyond the outer cylindrical diameter of the stator housing, thus creating a potential blockage when axially sliding the rotor assembly over the stator assembly. To address this issue, the proximal rotor tube 1685 is provided with an axial keyway or channel 1685*a* (illustrated in FIG. 89), which allows clearance for the protrusion of the teeth of gear 1635 beyond the cylindrical outer surface of the stator 1670 when the rotor assembly is proximally slid over the stator assembly.

Once the rotor assembly is slid into the axial position that provides engagement between the rotary gear 1671 and the transmission gear 1635, the axial positioning is locked by applying the C-shaped ring 1762 to the channel or slot 1685*b* of the proximal rotor tube 1685. The C-shaped ring has a pair of opposed ribs 1672*a*, 1672*b* that project radially inwardly from the otherwise generally cylindrical inner surface of the C-shaped ring 1672. Thus, these ribs 1672*a*, 1672*b* extend radially inwardly through one or more openings in the slot 1685*b* of the proximal rotor tube 1685 and radially inwardly beyond the inner cylindrical surface of the proximal rotor tube 1685. Since the axial position of the rotor assembly on the stator assembly corresponding to engagement of gears 1671 and 1635 results in axial alignment of the slot 1685*b* of the rotor tube 1685 with the slot 1674 of the stator 1670, the ribs 1672*a*, 1672*b* project radially inwardly into the slot 1674 of the stator 1670. Accordingly, the C-shaped ring 1672 simultaneously engages both the slot 1685*b* of the proximal rotor tube 1685 and the slot 1674 of the stator to thereby axially constrain the proximal rotor tube 1685 and the stator 1670 relative to each other, and thus also axially constraining the rotor assembly and the stator assembly relative to each other.

Since the slot 1674 is circumferentially continuous (in particular, having an annular geometry concentric with the axis of rotation of the rotor assembly with respect to the stator assembly), the ribs 1672*a*, 1672*b* are able to move circumferentially along the slot 1674, thereby allowing rotation of the rotor assembly relative to the stator assembly while maintaining the axial constraint.

This arrangement allows the rotatable drive collar 1615 to rotate while the internal components, including the tubes attached to the endoscope tube connectors 1670*a*, 1670*b*, remain substantially rotationally static with respect to the stator 1670.

In one form of the present invention, helical threads 1620 may be deformable. More particularly, investigating the small bowel requires that a visualization system navigate through narrow and torturous spaces as it advances to the small bowel. In some cases, it may be desirable to provide a visualization system with a deformable helical thread which is capable of assuming (i) a reduced profile in order to facilitate navigation to the small bowel, and (ii) an enlarged profile in order to thereafter provide the desired rotate-to-advance action within the small bowel. A visualization system with a deformable helical thread can also be used to traverse bodily passageways other than the small bowel, e.g., a visualization system with a deformable helical thread can also be used to traverse other portions of the gastrointestinal tract, the urinary tract, etc.

Figure 89A:
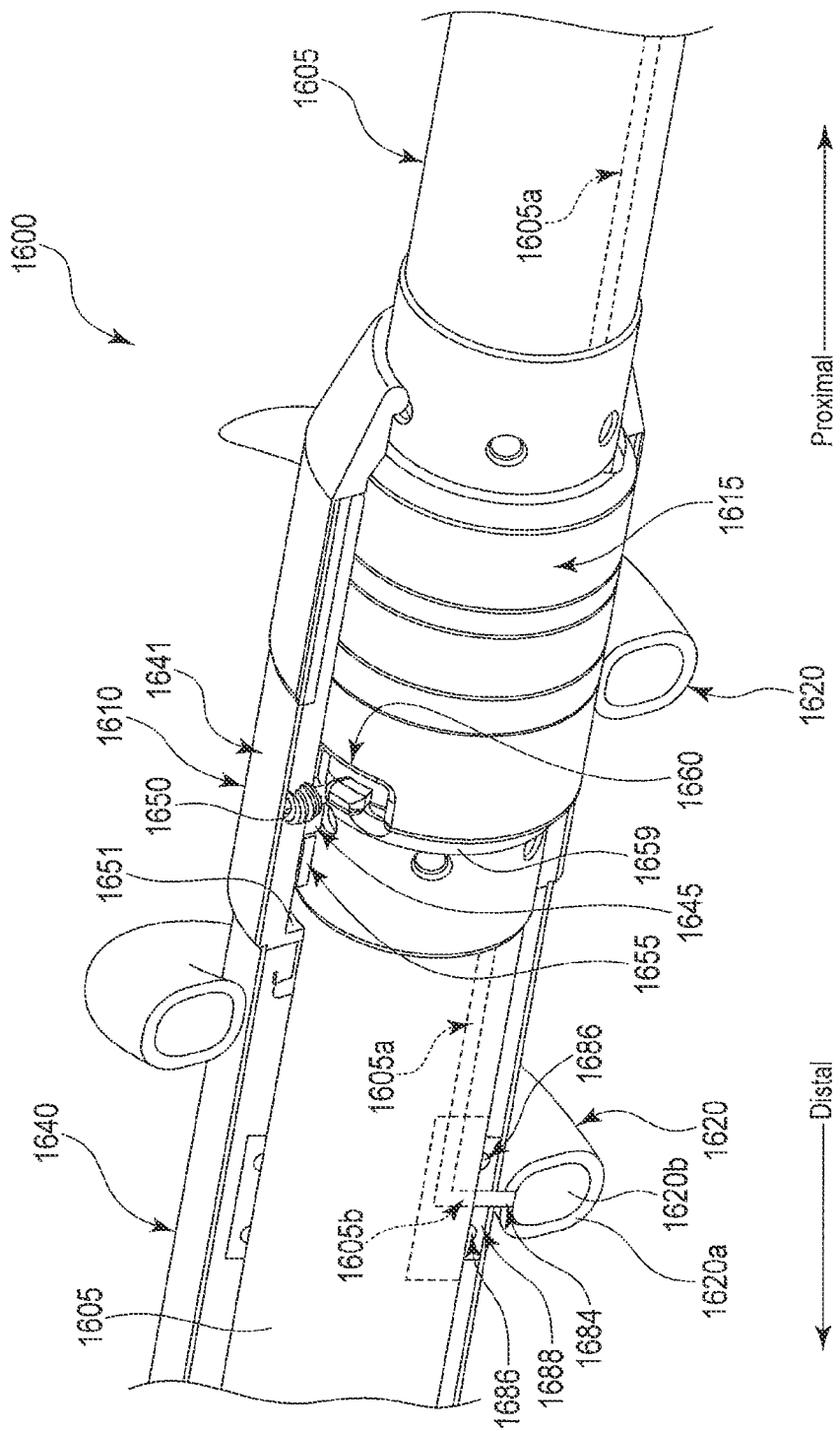
FIG. 89A is a schematic view showing how the novel visualization system of FIGS. 75-89 may comprise deformable helical threads.

To this end, referring to FIG. 89A, visualization system 1600 may be provided with a deformable helical thread 1620, in the form of a hollow, and inflatable, helical thread 1620, so as to be capable of achieving the aforementioned reduced profile, and the aforementioned enlarged profile, as desired.

FIG. 89A is a schematic view showing how the novel visualization system of FIGS. 75-89 may comprise deformable helical threads 1620. The threads 1620 include a flexible tubular structure 1620*a* surrounding an interior space 1620*b* that extends along the length of the threads 1620 such that the interior space 1620*b* is has a helical shape analogous to the helical shape of the threads 1620.

Deformable helical threads 1620 are configured so as to provide a reduced profile during navigation to the small bowel or other bodily passageway. Once in the small bowel (or other bodily passageway), this reduced profile thread can thereafter be inflated so as to assume the enlarged "rotate-to-advance" profile necessary to gather, or pleat, the small bowel (or other bodily passageway) tissue. The reduced profile thread of deformable helical thread 1620 provides less traumatic engagement with tissue during navigation to the small bowel (or other bodily passageway). However, it is important to note that once the visualization system is in the small bowel (or other bodily passageway), and deformable helical thread 1620 has assumed its enlarged profile, deformable helical thread 1620 must retain a sufficient structural integrity to advance the visualization system through the anatomy (in a rotate-to-advance procedure) or to pleat the small bowel (or other bodily passageway) tissue onto the visualization system (in a rotate-to-pleat procedure).

It should also be appreciated that deformable helical threads 1620 may be inflated by a variety of means. By way of example but not limitation, helical threads 1620 may be inflated (i) by delivering an appropriate inflating material (e.g., various liquids, gases or solids) to the interior of helical thread 1620, e.g., via one or more conduits connected to the helical thread, (ii) by a fluid that expands when influenced by an energy source (e.g., body heat or electricity), etc. By way of example but not limitation, helical threads 1620 may be inflated by means of a longitudinally-extending conduit 1605*a* which extends through endoscope 1605 and which communicates with a radially extending opening 1605*b* formed in the outer wall of the endoscope portion 1605 and with an opening 1684 formed in the base of helical threads 1620, by which an inflating material may be introduced into the interior space 1620*b* of deformable helical threads 1620.

In the illustrated embodiment of FIG. 89A, the interior space 1620*b* is in fluid communication with a conduit 1605*a* extending within the endoscope portion 1605. The longitudinally extending conduit 1605a opens into the radially extending opening 1605b is into fluid communication with opening 1684 of the drive tube 1610.

The opening or conduit 1684, which extends through both the tubular wall 1640 of the drive tube 1610 and radially inwardly disposed wall of tubular structure 1620a, provides a path of fluid communication between the fluid supply channel, in this example conduit 1605a, and the interior space 1620b of the endoscope 1605. Thus, the shape and/or rigidity of the threads 1620 may be controlled via a control fluid (e.g., a gas or liquid). The control fluid may be controlled via a pump or any other suitable actuator disposed at any suitable location (for example, a proximal location such as, e.g., within a handpiece). In an example embodiment, fluid may be forced into the interior space 1620b to expand the threads 1620 from a collapsed position to an inflated or expanded position. Further, the rigidity of the threads 1620 may be reduced by lowering the fluid pressure in the interior space 1620b, which would cause the threads 1620 to be softer and/or more easily deformable. This may be advantageous, e.g., to limit forces applied to particularly sensitive tissue. Although a single interior space 1620b is illustrated, it should be understood that multiple interior spaces 1620b may be provided. For example, one or more proximal interior spaces 1620b and one or more distal interior space 1620b may be provided such that the expansion and/or rigidity of respective proximal and distal portions of the threads 1620 may be independently controllable.

Although the radial portion 1605b is shown only in the lower portion of the endoscope portion 1605 illustrated in FIG. 89A, it should be understood that at least the radial portion 1605b of the fluid channel 1605a may be annular, or form a partial ring, such that, e.g., the channel 1684 of the drive tube 1610 maintains continuous fluid connection with the radial portion 1605b of the channel 1605a as the drive tube 1610 rotates one or more complete rotations with respect to the endoscope portion 1605. However, it should also be understood that the radial portion 1605b may be disposed at a relatively small, localized location such the radial portion 1605b comes into fluid communication with the channel 1684 only when the channel 1684 passes over the radial portion 1605b during rotation of the drive tube 1610.

A fluid-tight connection is maintained between the endoscope portion 1605 and the rotatable drive tube 1610 via a pair of annular seals in the form of o-rings 1686 which may have the same features as other seals described herein. The o-rings 1686 are supported in a mount, or annular block, 1688 formed in the sidewall of disposable drive tube 1610, in order to ensure that the inflating material is constrained as it advances from longitudinally-extending conduit 1680 into the interior 1620b of helical threads 1620. Since the two seals 1686 are disposed distally and proximally, respectively, to the interface between the radially extending portion 1605b of the channel 1605a and the fluid channel 1684 of the drive tube 1610, fluid is prevented from passing axially or distally, respectively, of the axial and distal seals 1686 even as the drive tube 1610 rotates with respect to the endoscope portion 1605.

In an exemplary form of use, visualization system 1600 is advanced to the small bowel or other bodily passageway in substantially the same manner as threaded camera introducer system 710A discussed above. Once in the small bowel (or other bodily passageway), deformable helical threads 1620 are inflated, e.g., via the aforementioned longitudinally-extending conduit 1680. After inflating deformable helical threads 1620, as visualization system 1600 is rotated, the small bowel (or other bodily passageway) tissue begins to gather on the exterior of helical threads 1620.

It should be appreciated that deformable helical threads 1620 are configured so as to be selectively deflatable as well as selectively inflatable. Such deflation may be accomplished by withdrawing the inflating material from helical threads 1620 via the aforementioned longitudinally-extending conduit 1680. This ability to deflate helical threads 1620 can be highly advantageous in situations where the visualization system is to be removed from the small bowel (or other bodily passageway) and/or when the visualization system becomes lodged in the small bowel (or other bodily passageway). This ability to deflate helical threads 1620 can also be advantageous in an emergency situation, inasmuch as the deformable helical threads may be rapidly deflated and the visualization system quickly removed from the small bowel (or other bodily passageway).

It should also be appreciated that deformable helical threads 1620 may be deflated by a variety of means. By way of example but not limitation, helical threads 1620 may be deflated through the application of suction at the proximal end of visualization system 1600, or by passing a sufficient amount of pressure through visualization system 1600 to cause the inflating material to exit through an opening (e.g., channel) formed in the distal end of helical threads 1620.

Furthermore, where the inflating material is a solid, helical threads 1620 may be deflated by passing a liquid (e.g., water) through visualization system 1600 in order to dissolve the inflating material contained within helical threads and then withdraw the solution proximally (or eject the solution distally). More particularly, in one embodiment, deformable helical threads 1620 may be filled with a solid (e.g., a powder) which may be dissolved by a liquid (e.g., water) into a liquid or gel-like consistency which can be withdrawn proximally (or expelled distally).

It is important to note that if the inflating material is expelled into a body lumen, the inflating material must be biocompatible so that it can be safely received within the body lumen after expulsion from the visualization system.

It should also be appreciated that helical threads 1620 may be formed from a variety of materials, or attached to visualization system 1600 by a variety of means, so that helical threads 1620 may be quickly removed from the remainder of the visualization system. In one embodiment, helical threads 1620 may comprises a hollow or solid spiral which dissolves within the body lumen after it has been detached from visualization system 1600. Alternatively, helical threads 1620 may be formed out of a dissolvable material (e.g., corn starch) which may be coated with a layer of water resistant material. A liquid (e.g., water) may then be infused via a lumen to dissolve the helical thread for withdrawal without rotation.

In another embodiment, helical threads 1620 may be magnetically attached to visualization system 1600.

In another embodiment, the minor diameter of the helical thread may be raised to a level which is equal to, or greater than, the major diameter of the helical thread, thereby resulting in the creation of a structure of uniform height, whereby to facilitate withdrawal of the visualization system from the body.

In still another embodiment, helical threads 1620 may comprise a hollow or solid spiral which is constructed out of multiple smaller tubes. The smaller tubes are held together with an adhesive or a solvent. The helical thread dissolves into its constituent components (e.g., the smaller tubes) when exposed to a material which alters the binding properties of the adhesive or bonding material.

In yet another embodiment, helical threads 1620 may comprise a hollow or solid spiral which is constructed out of multiple pieces that can be separate into many smaller pieces which can then be passed through the gastrointestinal tract when disconnected from visualization system 1600.

In still another embodiment, helical threads 1620 may be detached from visualization system 1600 and left in the body for a period of time in order to dispense drugs, take pictures or video to monitor healing progress, etc. The helical threads may comprise a tether for maneuvering the helical threads through the body lumen once the helical threads have been detached from visualization system 1600.

Figure 90:
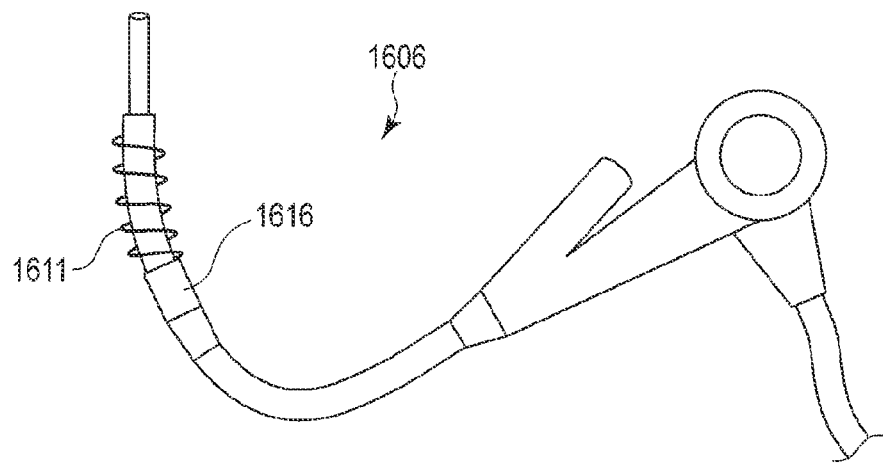
FIG. 90 shows an endoscope having a rotatable drive collar and a disposable drive tube.
Figure 91:
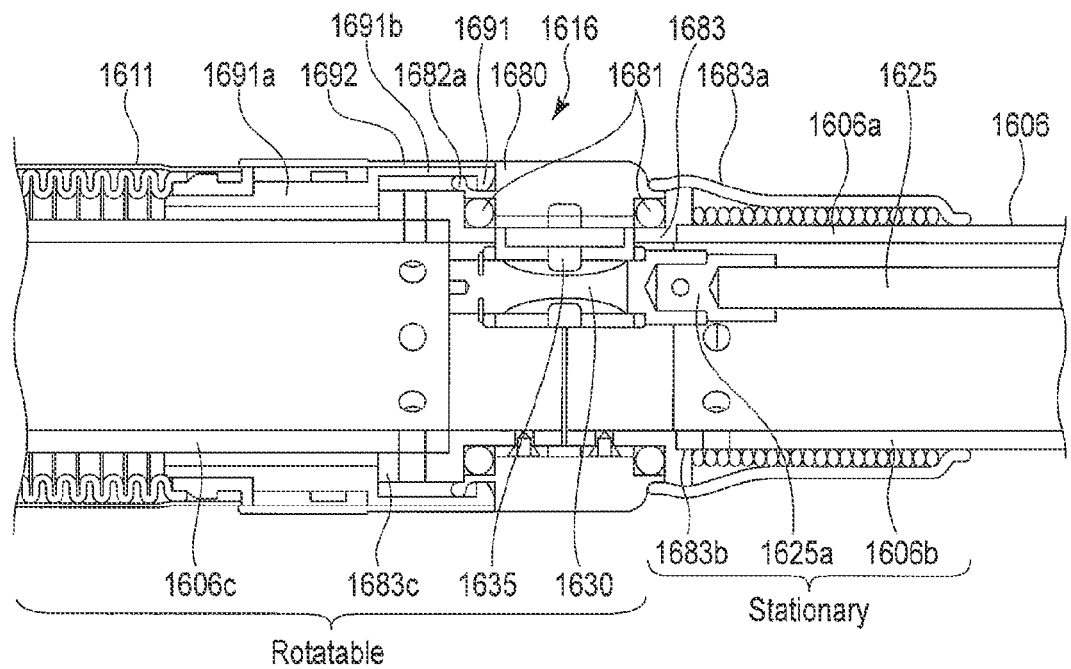
FIG. 91 is a sectional partial view of the endoscope of FIG. 90.
Figure 92:
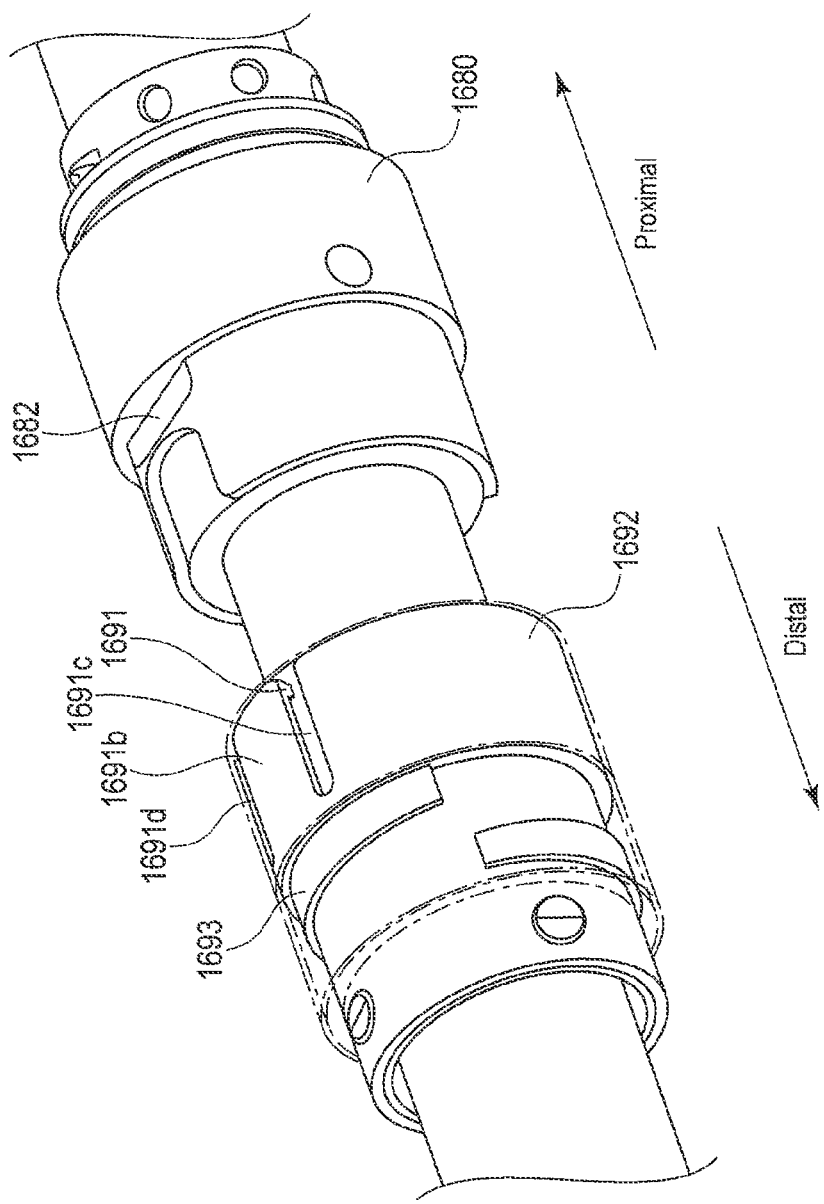
FIG. 92 is a perspective partial view of the endoscope of FIG. 90.
Figure 93:
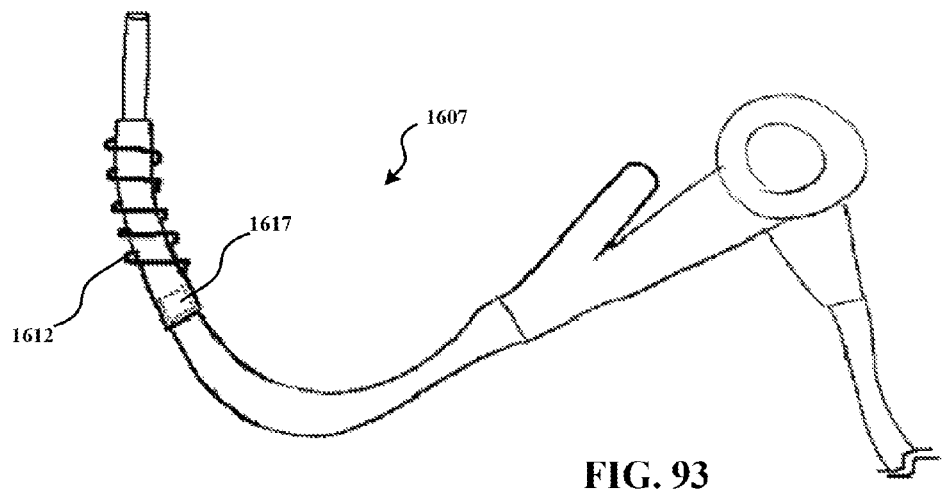
FIG. 93 shows an endoscope having a rotatable drive shaft and a disposable drive tube.

FIGS. 90-92 show another embodiment of an endoscope 1606, which comprises a rotatable drive collar 1616 and a drive tube 1611, which in the illustrated example is disposable. The endoscope 1606 includes features the same as or analogous to the other endoscopes described herein, e.g., endoscope 1605 described above, except to the extent indicated otherwise.

Referring to FIG. 91, the rotatable drive collar 1616 comprises: a stator 1683 disposed at an intermediate portion of an insertion portion 1606a of the endoscope 1606, the intermediate portion being disposed between a proximal portion 1606b of the insertion portion 1606a and a distal portion 1606c of the insertion portion 1606a; a rotor 1680 coupled with the disposable drive tube 1611; and sealing members 1681, each of which comprises an annularly-shaped rubber ring.

In the example illustrated in FIG. 91, the stator 1683 is connected to both the proximal and distal portions 1606b and 1606c of the insertion portion 1606a by respective annular circumferential flanges 1683b and 1683c. In this regard, the stator 1683 acts as a coupling between the proximal and distal portions 1606b and 1606c. The insertion portion 1606a of the endoscope 1606 is the portion that is configured to be inserted into the patient's body during an endoscopic procedure. Although the stator 1683 forms the intermediate portion of the insertion portion 1606a, it should be understood that a structure separate from the stator 1683 may be provided as the intermediate portion. It should be further understood that the proximal portion 1606b, the distal portion 1606c, and/or the intermediate portion of the insertion portion 1606a may be integrally formed as a continuous component.

The rotor 1680 is disposed over the stator 1683 so as to cover the stator 1683. The rotor 1680 is relatively rotatable with respect to the stator 1683 and has the rotary gear portion on its inner surface. Transmission gears 1630 and 1635 are provided to transfer the rotary motion from the flexible drive shaft 1625 to the rotor 1680, via the rotary gear portion on the inner surface of the rotor 1680, so that the disposable drive tube 1611 (which is coupled to the rotor 1690) is rotated, as illustrated in FIG. 91.

The sealing members 1681 are positioned in each opposed axial side or end of the rotor 1680, and form a water-tight seal between the rotor 1680 and the surface of the stator 1683. Thus, the sealing members 1681 protect the interior mechanisms and components (e.g., the gear train) of the endoscope 1606 against water exposure.

The disposable drive tube 1611 has a projection tip 1691 and slots 1691c and 1691d, and the rotor 1680 has a concave groove or recess 1682. The concave recess 1682 receives the projection tip 1691 of the disposable drive tube 1611 in order to couple—and in particular, releasably attach—the rotor 1680 and the disposable drive tube 1611. This coupling interface between the projection tip 1691 and the recess 1682 forms a detent mechanism. In this regard, the projection tip 1691 is formed as part of a tube 1692a and is supported by the main body of the tube 1692a via a cantilevered spring arm 1691b, which acts in the manner of a leaf spring to allow the projection tip 1691 to flex radially outwardly. This flexibility allows the projection tip 1691 to radially clear a distal lip 1682a of the channel 1682 when the drive tube 1611 is proximally moved into engagement with the rotor 1680, in order to allow the projection tip 1691 to extend into the channel 1682 as illustrated in FIG. 91.

Referring to FIG. 92, the disposable drive tube 1611 further comprises an outer cover 1692 and a compression spring 1693. The compression spring 1693 biases the outer cover 1692 proximally so that the projection tip 1691 is covered by the outer cover 1692 to reinforce the connection of the projection tip 1691 and the concave channel 1682. In particular the outer cover 1692 restrains the projection tip 1691 from flexing radially outwardly from the channel 1682, which maintains the positive stop against axial movement formed between the projection tip 1691 and the channel 1682. Thereby, unintentional detachment of the drive tube 1611 and the rotor 1680 may be prevented when the outer cover 1692 is in its proximal position. In order to detach the drive tube 1611 from the rotor 1680, the operator may, e.g., manually, slide the outer cover 1692 distally, to overcome the bias force of the spring, and allow the projection tip 1691 to flex radially outwardly in order to disengage the channel 1682.

Although two projection tip/channel interfaces are provided in the illustrated example at diametrically opposed sides of the drive tube 1611, it should be understood that any number of such interfaces, including a single interface, may be provided at any desired regular and/or irregular circumferential spacing. It should be further understood that one or more of the interfaces may be reversed such that the drive tube 1611 has a channel configured to receive a corresponding projection tip of the rotor 1680.

Referring to FIG. 91, the endoscope 1606 has a boot 1683a located on the proximal side of the rotatable drive collar 1616. The boot 1683a comprises an outer sheath for preventing or resisting bending of the insertion portion 1606a of the endoscope 1606 about the rotatable drive collar 1616, e.g., in planes including or parallel to the longitudinal axis of the rotatable drive collar 1616, thereby providing a strain relief mechanism for the proximal portion 1606b of the insertion portion 1606a of the endoscope 1606, as well as the rotatable drive shaft 1625, which is rotatably supported by and along the proximal portion 1606b. Further, the reinforcement provided by the boot 1683a against bending of the proximal portion 1606b helps to ensure that the distal portion of the flexible drive shaft 1625 is aligned with the axis of rotation of the transmission gear 1630 at a coupling 1625a, which may be beneficial for providing efficient transfer of force from the flexible drive shaft 1625 to the transmission gear 1630 as well as allowing for a simplified and reliable coupling 1625a.

The proximal edge of the rotor 1680 is contacted and covered by the distal end of the boot 1683a, which further contributes to the waterproofing by providing a barrier or seal in addition to the proximal sealing member 1681. Although the boot 1683a contacts the rotor 1680 around the entire circumference of the rotor 1680 to form a continuous barrier or seal, it should be appreciated that the boot 1683a contact and/or extend around less than the entire circumference of the rotor 1680. The disposable drive tube 1611 and the rotor 1680 are configured to rotate together while the stator 1683 and the boot 1683a are rotationally stationary. However, it should be understood that the boot 1683a may be configured to rotate with the rotor 1680.

FIGS. 93-98 show another example embodiment of an endoscope 1607, which comprises a rotatable drive collar 1617 and a drive tube 1612, which in the illustrated example is disposable drive tube. The endoscope 1607 includes features the same as or analogous to the other endoscopes described herein, e.g., endoscopes 1605 and 1606 described above, except to the extent indicated otherwise.

The rotatable drive collar 1617 comprises a stator 1706 disposed at an intermediate portion between proximal and distal ends of an insertion portion of the endoscope 1607, a rotor 1700, and sealing members 1701 each of which comprises an annularly-shaped rubber ring.

Figure 94:
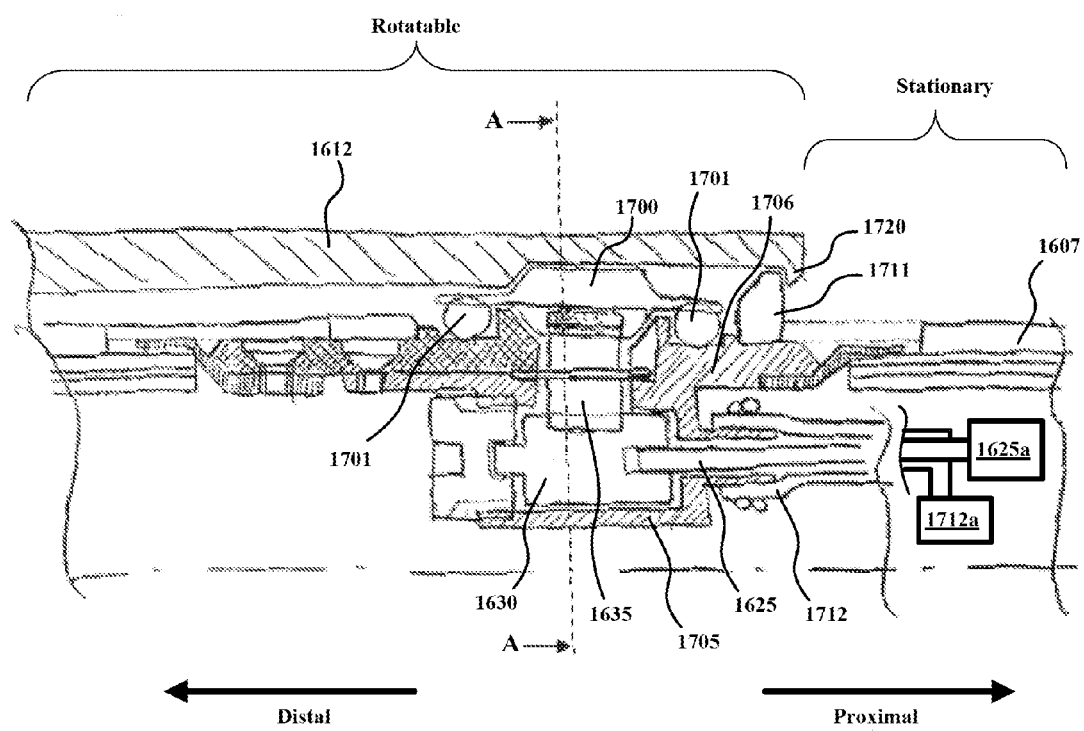
FIG. 94 is a partial sectional view of the endoscope of FIG. 93.
Figure 95:
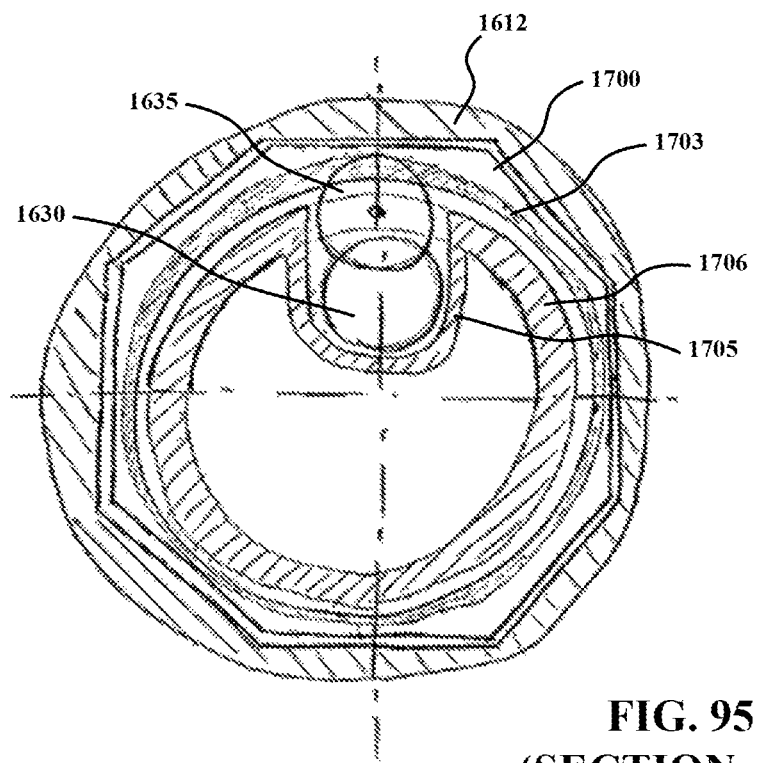
FIG. 95 is a sectional view corresponding to section A-A of FIG. 94.
Figure 96:
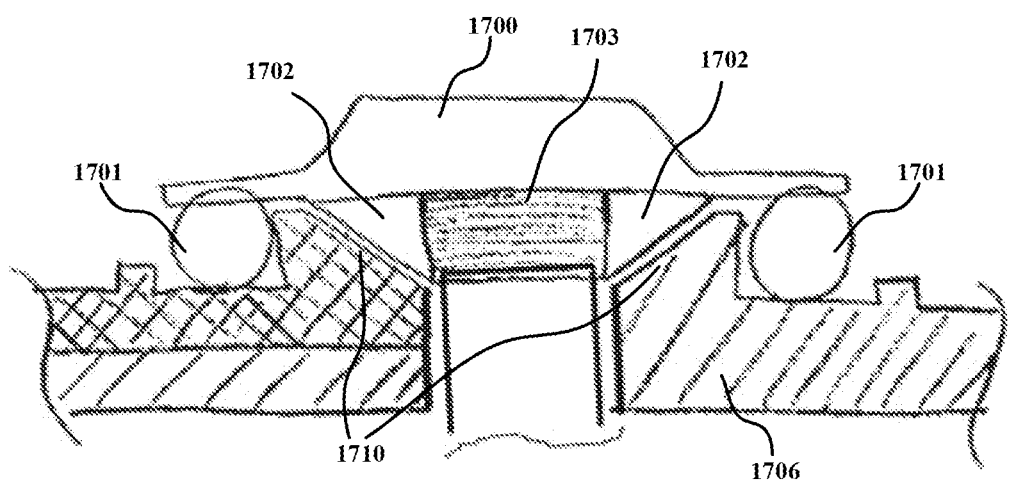
FIG. 96 is an enlarged portion of the sectional view of FIG. 94.

Referring to FIGS. 94-96, the rotor 1700 has a rotary gear portion 1703 geared with a transmission gear 1635, and a stabilizing portion 1702. The stabilizing portion 1702 comprises an annularly shaped protrusion formed on an inner surface of the rotor 1700. The stabilizing portion 1702 is located between a sealing member 1701 and the rotary gear portion 1703, and received in a holder 1710 which is formed on the stator 1706 so that the axial and radial movement of the rotor 1700 with respect to the stator 1706 is restrained, as illustrated in FIGS. 94-96.

Figure 97:
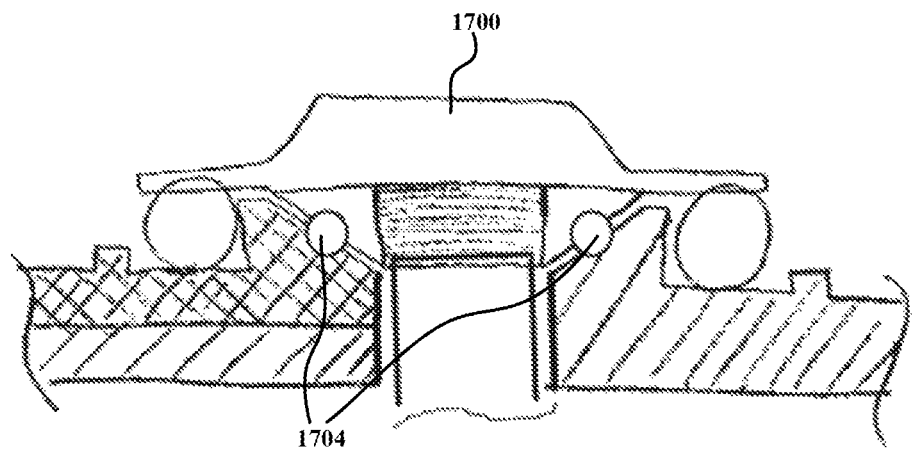
FIG. 97 corresponds to the structure illustrated in FIG. 96 modified to have a bearing interface.
Figure 98:
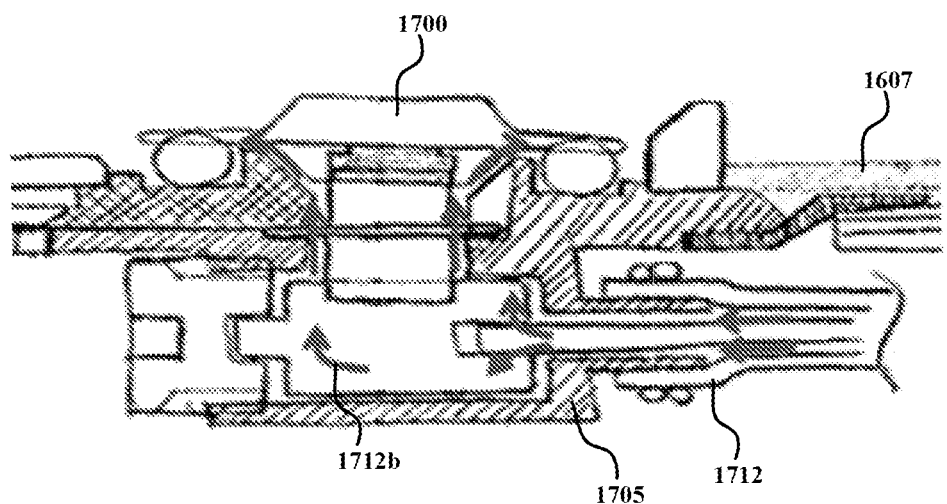
FIG. 98 is a partial sectional view of the endoscope of FIG. 93 schematically showing an airflow.
Figure 99:
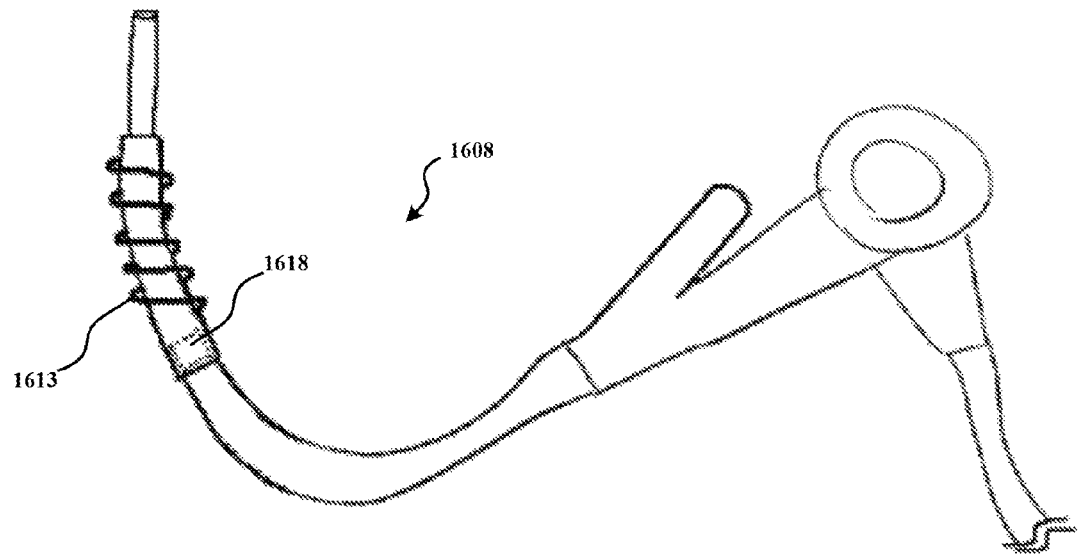
FIG. 99 shows an endoscope having a rotatable drive shaft and a disposable drive tube.
Figure 100:
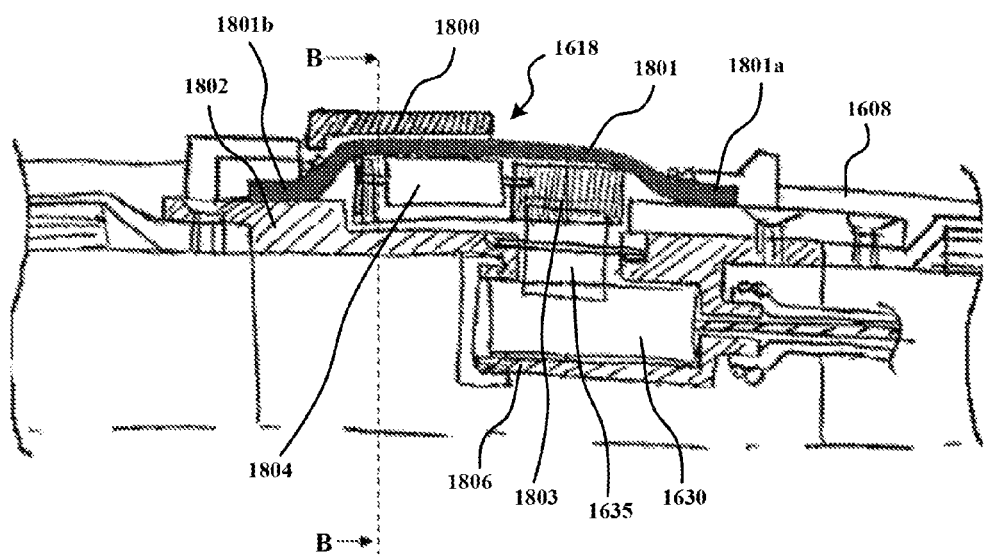
FIG. 100 is a partial sectional view of the endoscope of FIG. 99.

Preferably, bearings 1704 between the stabilizing portion 1702 and the holder 1710 may be provided in order to reduce the friction of rotating the rotor 1700, such as shown in the modified arrangement illustrated in FIG. 97.

Referring to FIG. 95, the cross-sectional shape of both the rotor 1700 and the disposable drive tube 1612 is polygonal. In other words, an outer surface of the rotor 1700 in cross section has a polygonal shape, and an inner surface of the drive tube 1612 in cross section has a polygonal shape. By this mechanism, the rotor 1700 may be inserted into the disposable drive tube 1612, and rotation of the rotor 1700 may be transferred to the disposable drive tube 1612 by engagement between the corresponding polygonal cross-sections. Although engagement between polygonal cross-sectional structures is provided to transfer the rotation, it should be understood that other keyed interfaces may be provided.

Referring to FIG. 94, the disposable drive tube 1612 has a projection tip 1720, and the stator 1706 has a stopper 1711 in the form of a radial flange or projection. As the projection tip 1720 and the stopper 1711 are rotatably connected, the disposable drive tube 1612 is rotated by the rotor 1700 and is restrained against axial movement by engagement between the projection tip 1720 and the stopper 1711.

A flexible drive shaft 1625 for transmitting a rotational force from a drive source, which is schematically illustrated as actuator 1625a in FIG. 94, to the disposable drive tube 1612 through the rotor 1700 extends in a shaft cover sheath 1712. The shaft cover sheath 1712 and a gear box 1705, including the transmission gears 1630 and 1635, are airtightly connected.

A proximal side of the shaft cover sheath 1712 is connected with an air pump system 1712a, which is schematically illustrated in FIG. 94. The air pump system 1712a supplies air pressure into the shaft cover sheath 1712 so as to generate an airflow from the air pump 1712a to the outside of the endoscope 1607 via the gear box 1705. This airflow, illustrated by arrows 1712b in FIG. 98, prevents water or other fluids from entering the interior of the endoscope. Thus, objects arranged in the interior of the endoscope can be protected against water or other fluid exposure.

FIGS. 99-104 show another embodiment of an endoscope 1608, which comprises a rotatable drive collar 1618 and a drive tube 1613, which is provided in the form of a disposable drive tube in the illustrated example. The endoscope 1608 includes features the same as or analogous to the other endoscopes described herein, e.g., endoscopes 1605, 1606, and 1607 described above, except to the extent indicated otherwise.

The rotatable drive collar 1618 comprises a stator 1802 having a gear box 1806, a rotor 1800, a rotary gear 1803, and a gear cover 1801.

The gear cover 1801 comprises a tubular member that covers a portion of the rotary gear 1803 which is exposed outside of the housing of the endoscope 1608. Distal and proximal ends 1801a, 1801b of the gear cover 1801 are watertightly fixed to the surface of the stator 1802. Therefore, the gear cover 1801 forms a water-tight seal to protect the rotary gear 1803 and an inner mechanism of the endoscope against exposure to water or other fluids.

The rotary gear 1803 has a carrying roller 1804 on its outer surface, and the rotor 1800 has housing rollers 1805 on its inner surface.

The carrying roller 1804 is positioned between the housing rollers 1805 over the gear cover 1801. Rotating the rotary gear 1803, the carrying roller 1804 and the housing rollers 1805 roll the surface of the gear cover 1801 to reduce the friction caused by the gear cover 1801.

Figure 101A:
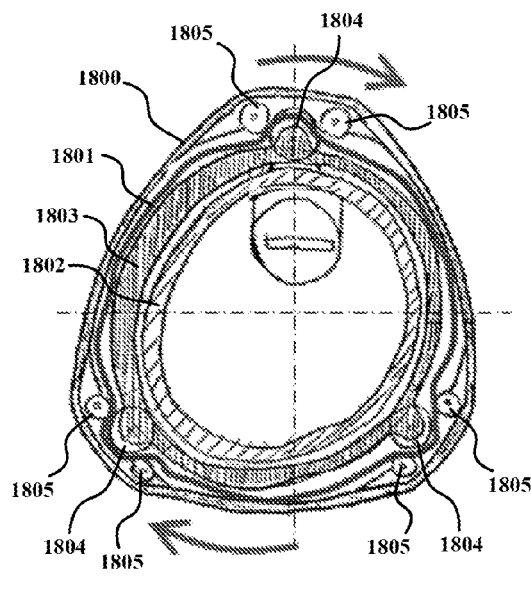
FIGS. 101A and 101B are sequential sectional views of the endoscope of FIG. 100 taken along section B-B when the endoscope is in respective states of rotation.
Figure 101B:
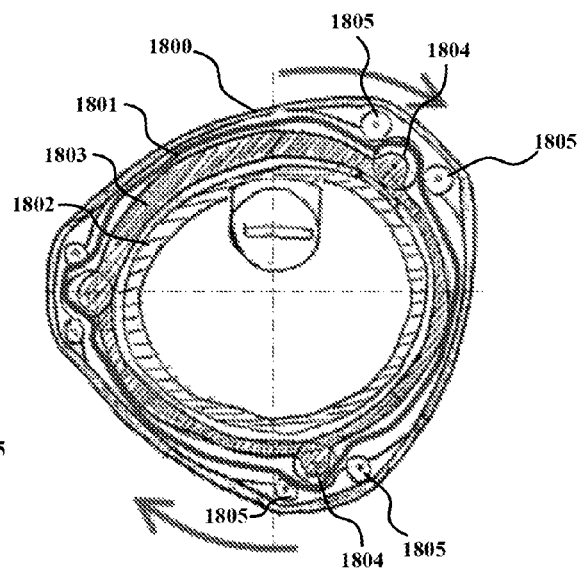
Figure 102:
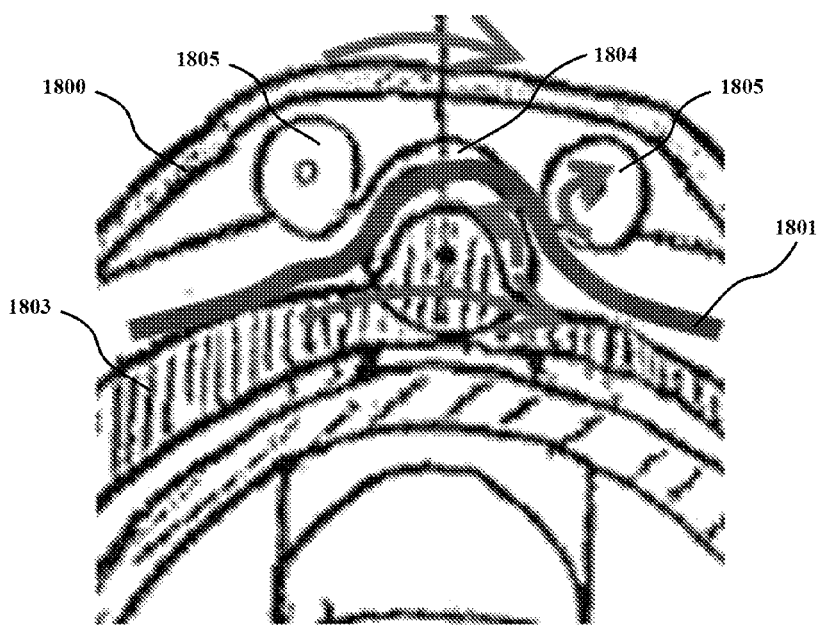
FIG. 102 is an enlarged portion of the sectional view of FIG. 101A.

Thus, despite not rotating the gear cover 1801, the housing rollers 1805 maintain the carrying roller 1804 therebetween, and the carrying roller 1804 can thereby transfer the rotary motion of the rotary gear 1803 to the rotor 1800 across the gear cover 1801, as illustrated, e.g., in FIGS. 101A, 101B, and 102.

Figure 104:
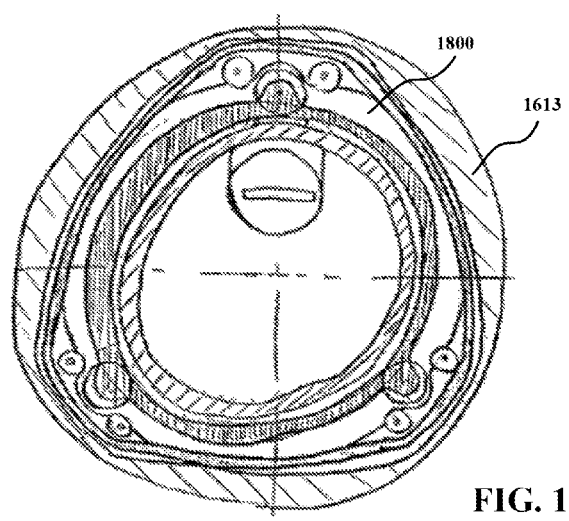
FIG. 104 is a sectional view of the endoscope of FIG. 103 taken along section C-C.

Shapes of the rotor 1800 and the disposable drive tube 1613 in a cross section are odd-shaped (in particular, a triangle-like shape in the illustrated example), so that they are coupled together by means of carrying rollers 1804 and the respective sets of housing rollers 1805 when the rotor 1800 is inserted into the disposable drive tube 1613, as illustrated in FIG. 104.

Figure 103:
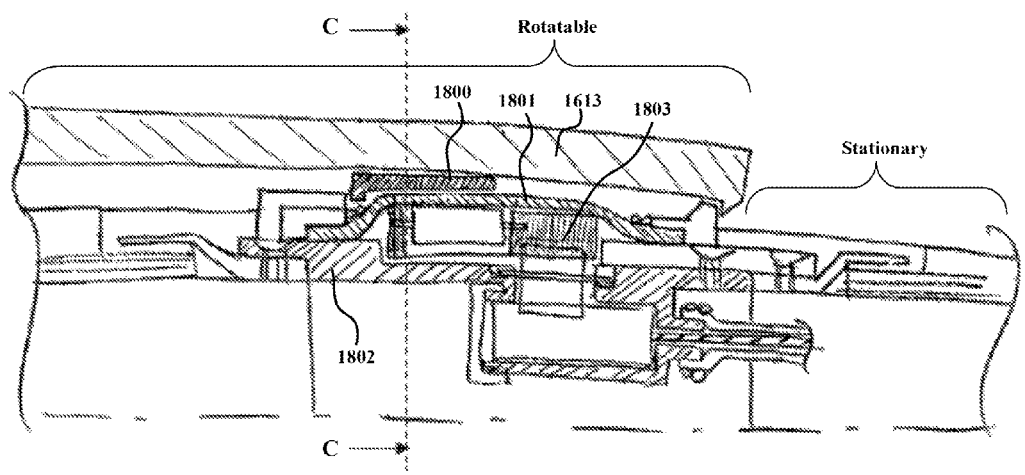
FIG. 103 is a partial sectional view of the endoscope of FIG. 99.

Referring to FIG. 103, in order to rotate the disposable drive tube 1613, the rotary gear 1803 and the rotor 1800 are rotated, and the stator 1802 and the gear cover 1801 are stationary.

FIGS. 105-109 show another example embodiment of an endoscope 1609, comprising a rotatable drive collar 1619, a drive tube 1614 (in the form of a disposable drive tube in the illustrated example), and a detachable drive unit 1910. The endoscope 1609 includes features the same as or analogous to the other endoscopes described herein, e.g., endoscopes 1605, 1606, and 1607 described above, except to the extent indicated otherwise.

Figure 105:
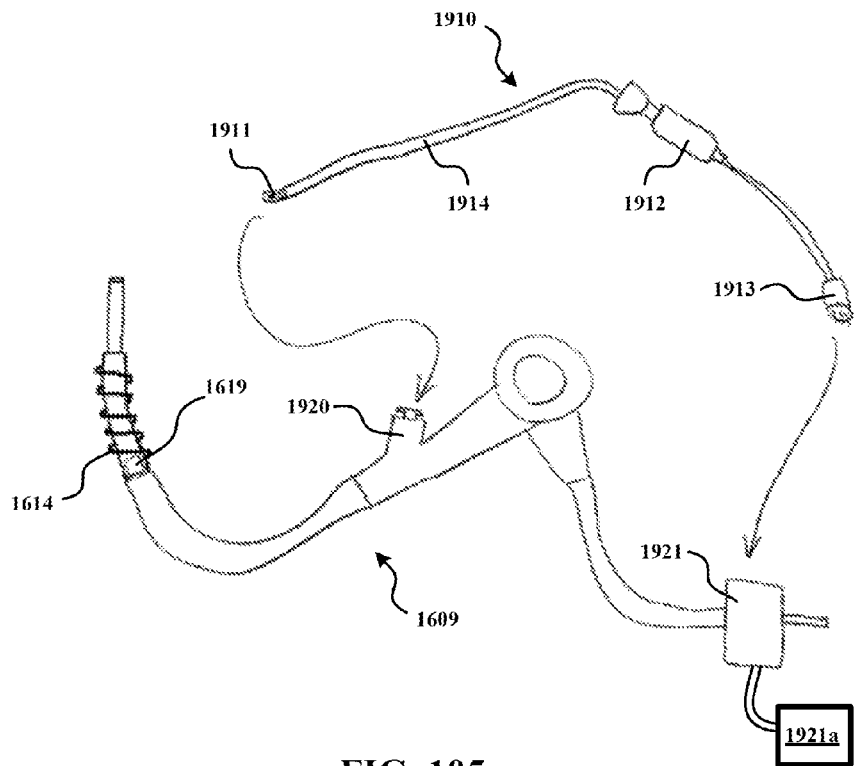
FIG. 105 shows an endoscope having a rotatable drive shaft, a disposable drive tube, and a detachable drive unit.
Figure 106:
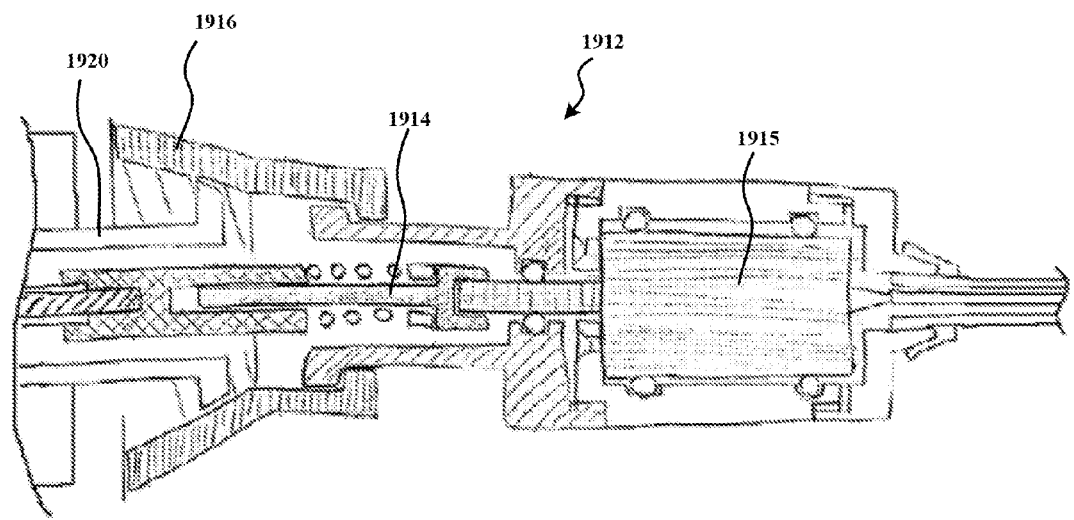
FIGS. 106 to 109 are partial sectional views of the endoscope of FIG. 105.

Referring to FIGS. 105 and 106, the detachable drive unit 1910 comprises a flexible drive shaft 1914, a motor unit 1912, and a motor connector 1913. The flexible drive shaft 1914 has a transmission gear 1911 on its distal end. The motor connector 1913 is connected to the scope connector 1921, and the scope connector 1921 is connected with an electric power supply 1921a, in order to provide power to activate the motor 1915. The power supply 1921a may be any suitable power supply, e.g., one or more batteries and/or power cells and/or a power grid. The flexible drive shaft 1914 is rotated by the motor 1915.

Figure 107:
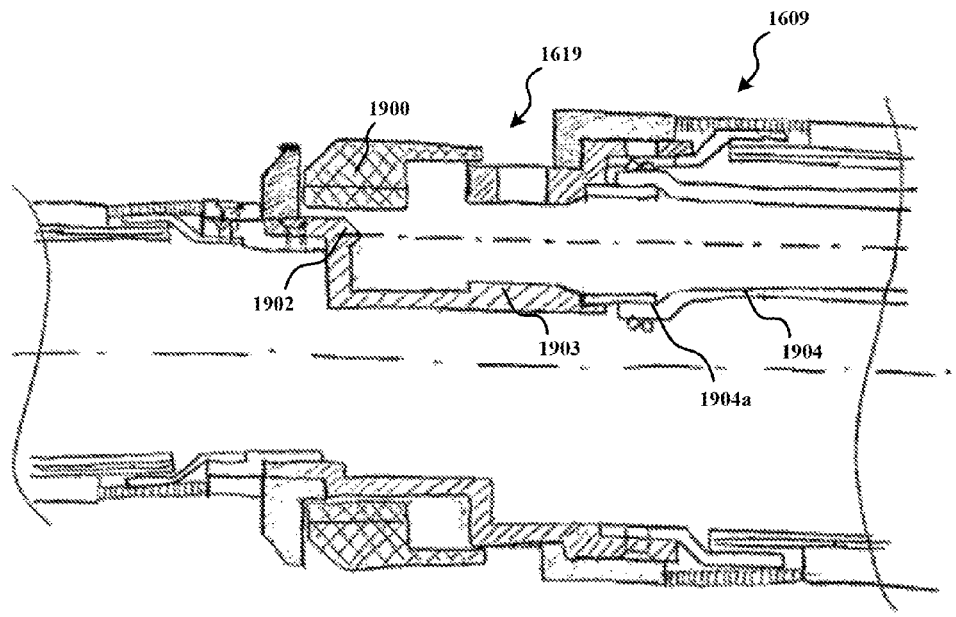

Referring to FIG. 107, the rotatable drive collar 1619 comprises a stator 1902, and a rotor 1900. The stator 1902 includes a gear box 1903. Further, the endoscope 1609 has a channel sheath 1904. A distal end portion 1904a of the channel sheath 1904 is in communication with the gear box 1903, and a proximal end of the channel sheath 1904 is in communication with a channel port 1920 disposed on the handle of the endoscope 1609.

Figure 108:
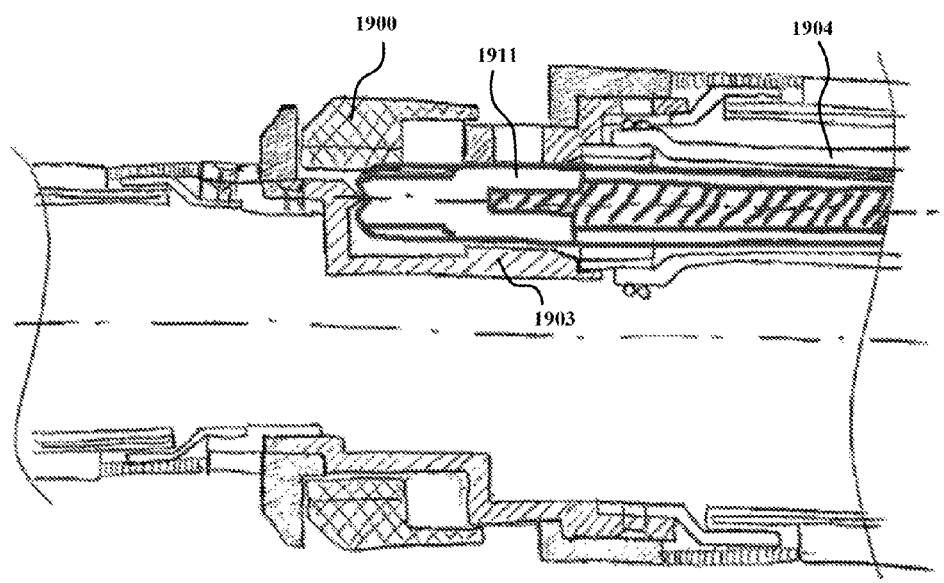

Referring to FIG. 105, the detachable drive unit 1910 is inserted into the channel sheath 1904 via channel port 1920, such that the transmission gear 1911 is positioned in the gear box 1903, as illustrated in FIG. 108.

Referring to FIG. 106, the detachable drive unit 1910 has an attachment 1916, which is disposed on a distal end of the motor unit 1912. The attachment 1916 is connected with the channel port 1920, thereby coupling the detachable drive unit 1910 with the endoscope 1609.

The rotor 1900 is axially movable with respect to an insertion portion of the endoscope 1609, and has a rotary gear portion on its inner surface.

Figure 109:
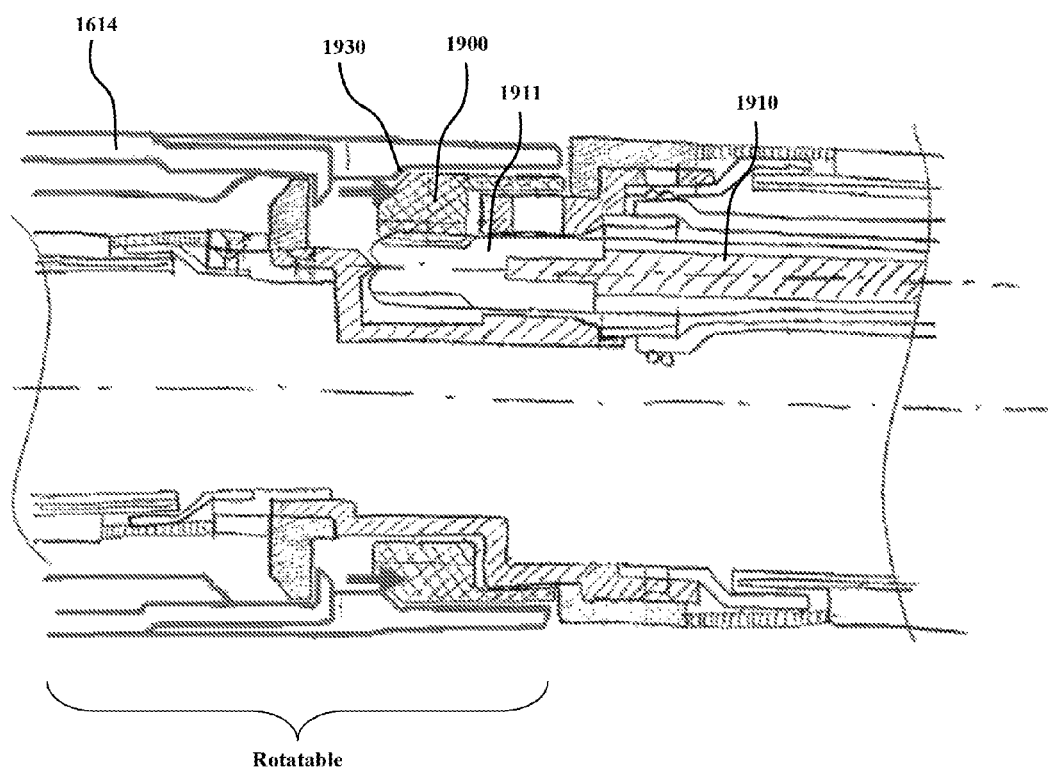

Referring to FIG. 109, after the detachable drive unit 1910 is inserted, the disposable drive tube 1614 in assembled to cover the endoscope 1609 (by advancing the tube 1614 from a distal side to a proximal side of the endoscope 1609). Then, the shoulder 1930 of the disposable drive tube 1614 pushes the rotor 1900 from the distal position shown in FIG. 108 to the proximal position shown in FIG. 109, so that the rotary gear portion of the rotor 1900 and the transmission gear 1911 engage.

Shapes of the rotor 1900 and the disposable drive tube 1614 in a cross section are polygonal, so that they are locked together when the rotor 1900 is inserted into the disposable drive tube 1614.

Activating the motor 1915, the flexible drive shaft 1914 with the transmission gear 1911 is rotated, and the rotor 1900 and the disposable drive tube 1614 are thereby rotated.

In this embodiment, the rotating mechanism, in particular the detachable drive unit 1910, is a separate component, and gears, channel sheath may be cleaned, sanitized, and/or sterilized after use.

Preferred Helical Thread Constructions

The foregoing preferred embodiments of the present invention may include a number of additional designs which can improve the effectiveness of the rotate-to-advance catherization system. These additional designs may relate to the helical thread construction.

Figure 48:
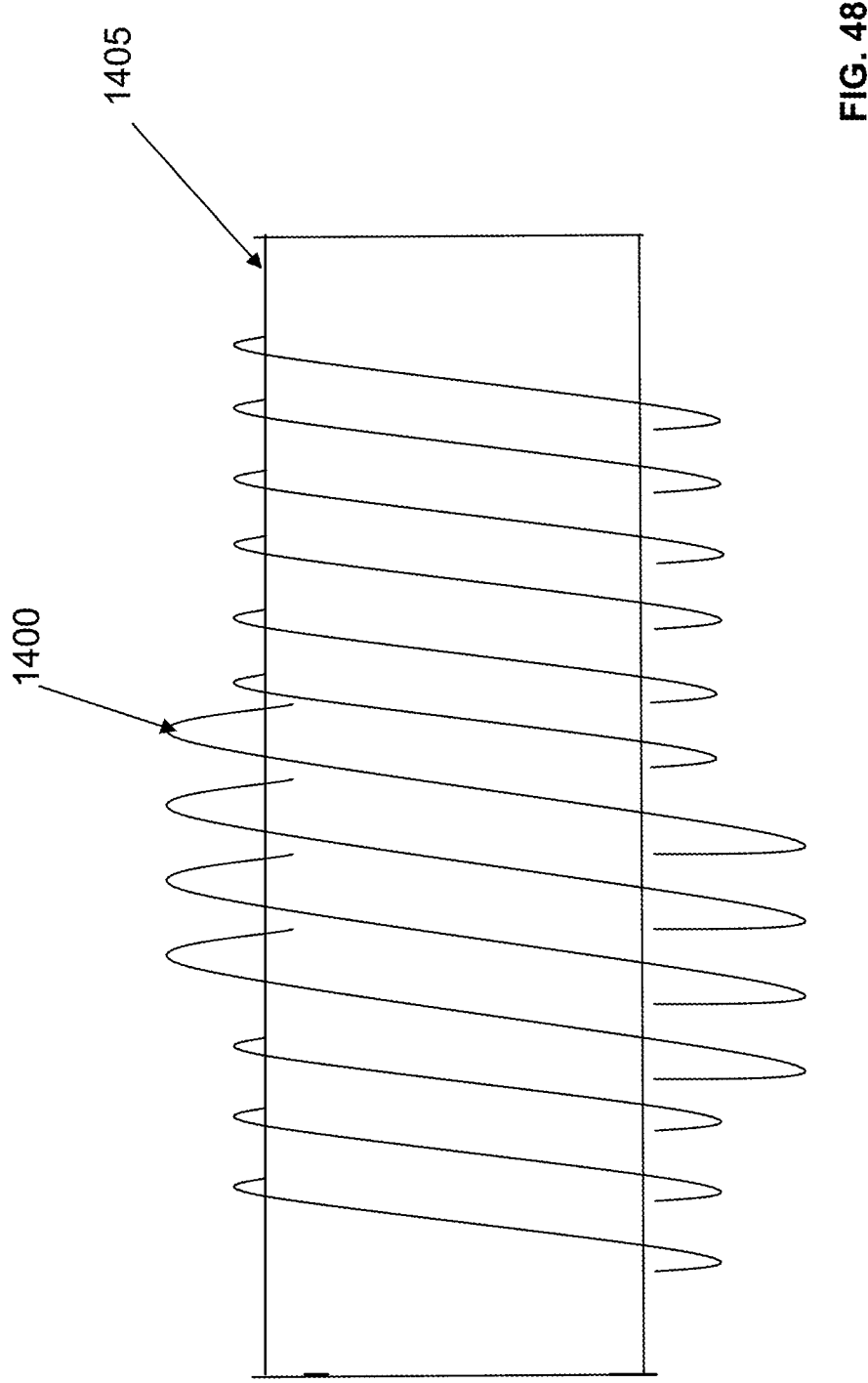
FIGS. 48-55 show various preferred configurations for the helical thread construction.
Figure 49:
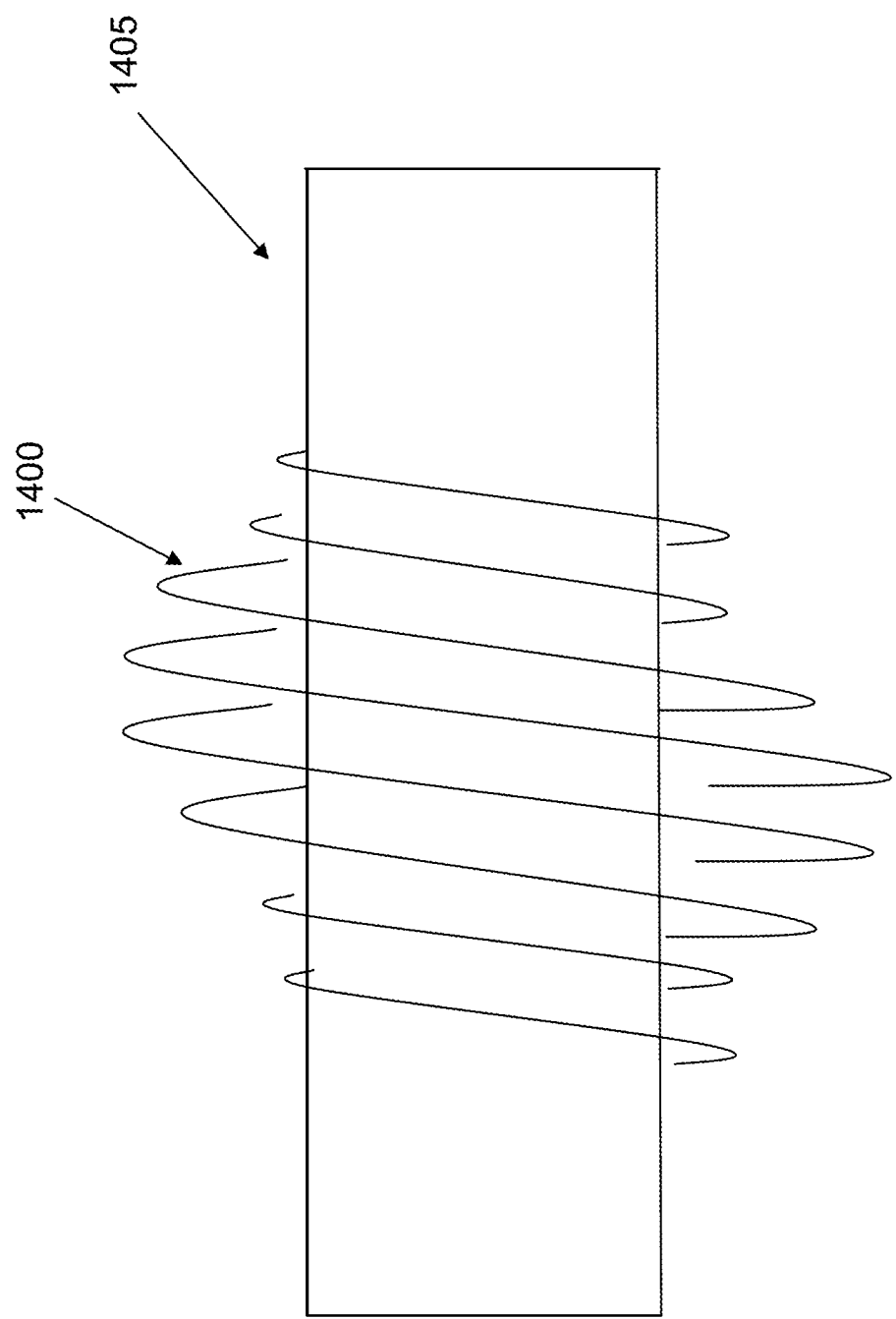
Figure 50:
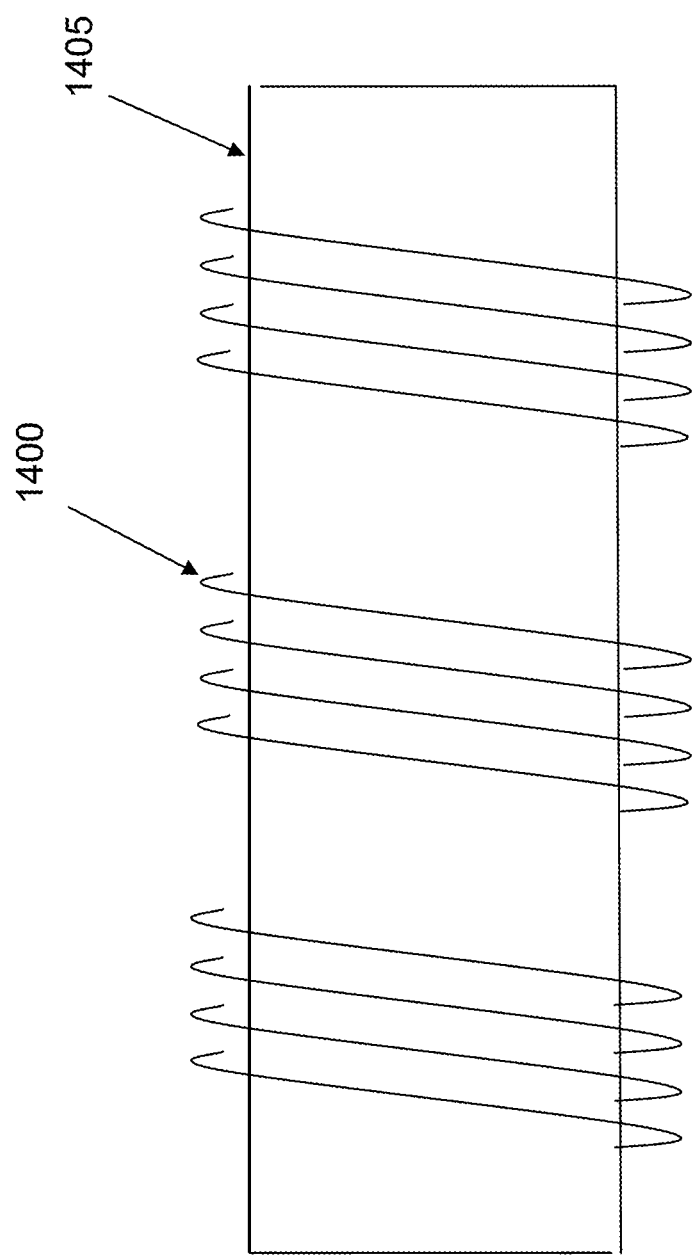

As noted above, the thread height of the helix may vary over its length as an aid to the advancement and retention characteristics of the device (see, for example helix 1400 disposed on shaft 1405 in FIG. 48), and may taper in height at various locations to optimize advancement and anchoring (see, for example, FIG. 49). Additionally, and in accordance with a further embodiment of the present invention, the helix may be constructed with an interrupted thread or a series of thread segments in order to produce the desired advancement and anchoring functions (see, for example, FIG. 50). The thread element may be affixed to the tube or may be molded integrally on the diameter of a tubular member which is positioned onto the tubular device. The tubular member, or sections of the member, may be sized to provide radial compression once positioned on the device to effect retention during use. Alternatively the thread may be overmolded directly onto a tubular device.

Preferred Variable Pitch Helix Construction

Figure 51:
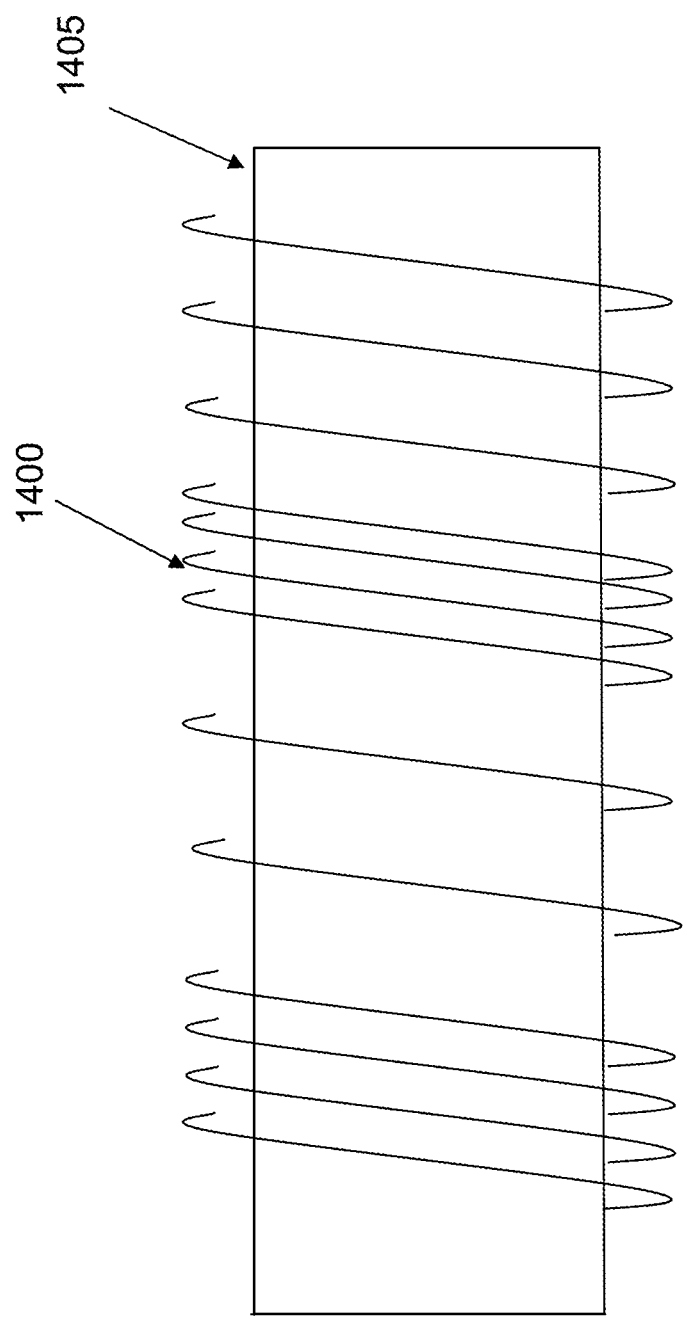

In accordance with a further embodiment of the present invention, the helix may be constructed with at least two different thread pitches along the length of a device so as to produce different tissue (or material) movement relative to the device (see, for example helix 1400 disposed on shaft 1405, FIG. 51). By way of example, a variable pitch helix construction may be advantageous in gathering the redundant colon over an endoscope or facilitating the removal of waste material within the colon. Additionally, a variable pitch helix construction may be utilized to optimize the anchoring of a device within the anatomy.

Preferred Thread Surface Geometry

Figure 52:
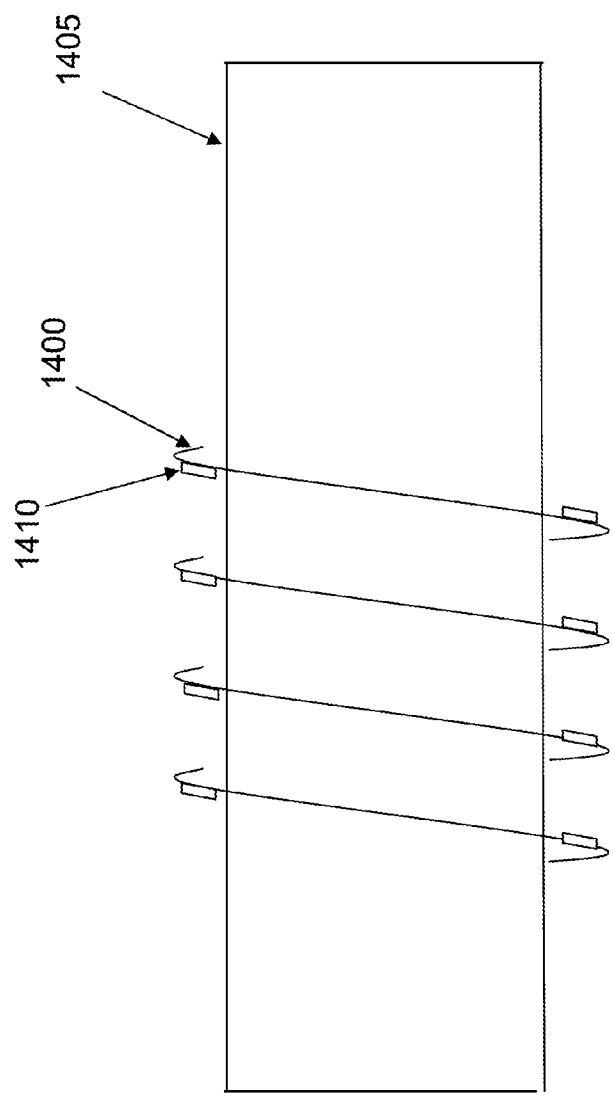
Figure 53:
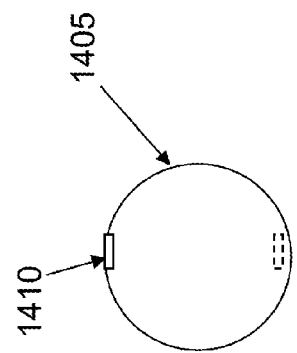

In another preferred embodiment of the present invention, the thread surface of the helix may be constructed with protrusions and/or recesses on the surface so as to improve advancement or anchoring of a device (see, for example, FIGS. 52 and 53 which show protrusions 1410 on helix 1400).

Figure 54:
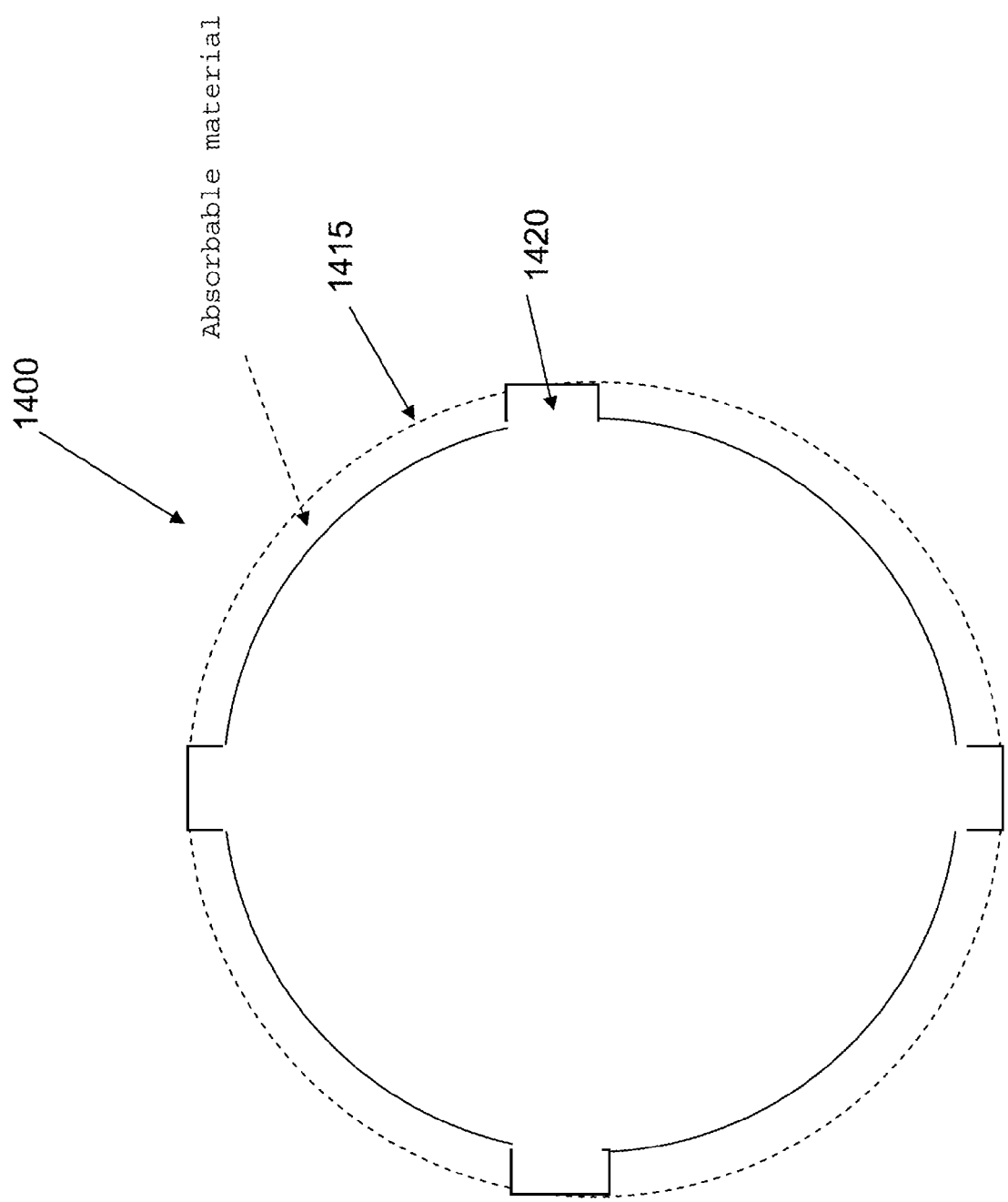
Figure 55:
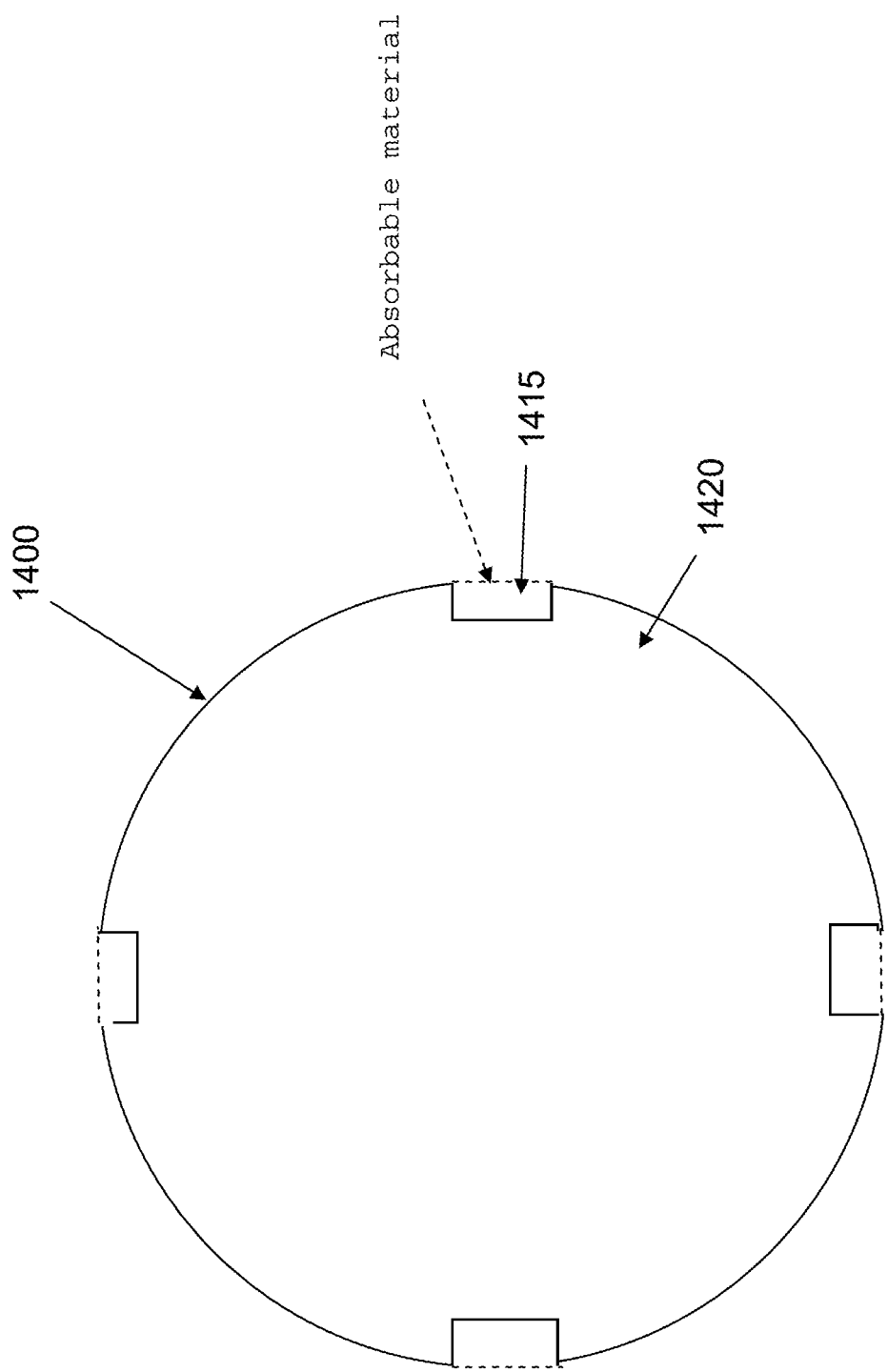
Figure 56:
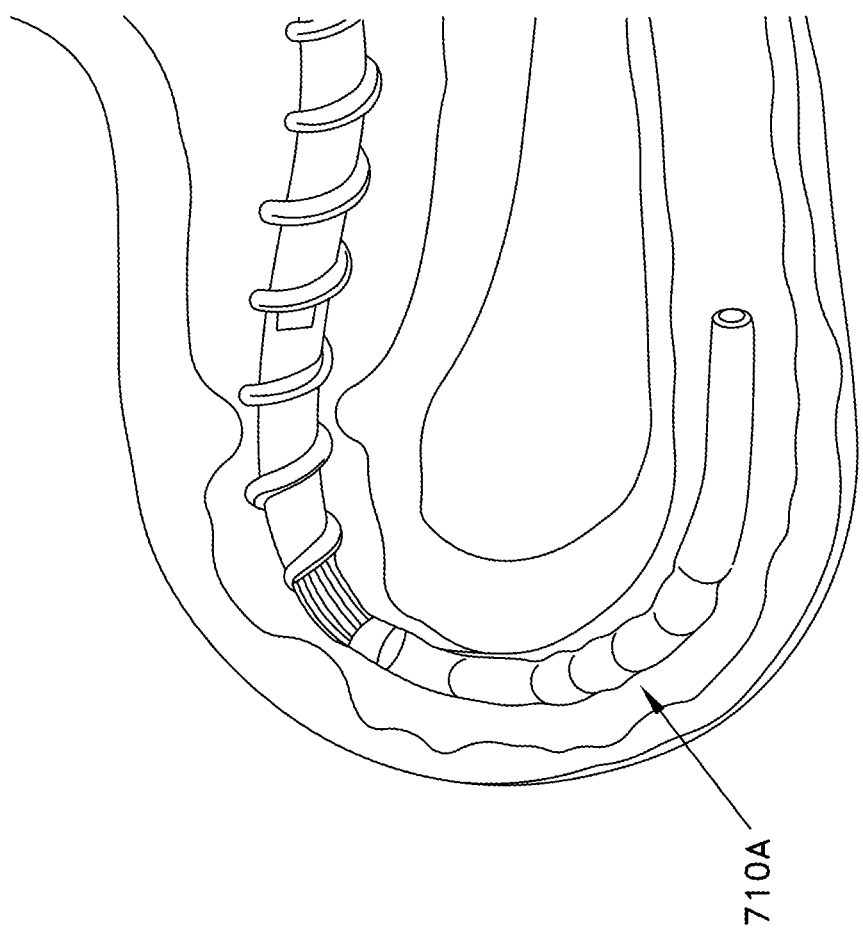
FIGS. 56-62 show a camera introducer system examining the small bowel in accordance with the present invention.

If desired, this geometry may be encapsulated within bioabsorbable or temporary material to change the surface geometry after insertion within the body. See, for example, FIGS. 54 and 55 which show the helix 1400 formed out of absorbable material 1415 and non-absorbable material 1420.

The thread cross-section may also be non-symmetrical with respect to the vertical centerline to enhance the advancement or anchoring within a bodily lumen. The shape may be designed to allow the thread to deflect in a beneficial manner so as to improve performance.

Properties of Thread Material

As noted above, the thread element may be solid, hollow and/or fluid-filled. It may be constructed with rigid, elastomeric, or a combination of materials. By way of example but not limitation, the thread elements may be formed out of PVC, polyurethane, TPE, silicone, TFEs, medical grade stainless steel, tantalum, titanium, nickel-titanium alloy, etc. Conversely, materials may be specifically chosen to be bioabsorbable so as to obviate the need for removal of the thread element of the helix. Alternatively, the thread element may be constructed out of at least two materials having different properties so as to obtain desired composite properties, such as, for example, hardness, friction, compliance, and/or radiopacity.

Helix Device Incorporating Sensors

In another preferred embodiment of the present invention, the helix device may comprise one or more sensors so as to indicate conditions such as temperature, pressure, radiation, position and/or any other status for diagnostic or therapeutic treatment during the procedure.

Rotary Coupling Design

In another preferred embodiment of the present invention, a coupling may be fixed to the endoscope or device with a variety of methods. The attachment force may be, for example, mechanical, hydraulic, pneumatic, magnetic, and/or adhesive. Or a radial force design may be used, utilizing a deformable element to create a frictional clamping, which can be reversed to unlock the coupling. A coupling may be provided which incorporates a uni-directional clutch to permit rotation in a single direction (i.e., clockwise only or counter-clockwise only). In one embodiment, the clutch direction may be changed by the operator to facilitate advancement in one direction and withdrawal by rotating in the opposite direction. In another embodiment, a one-way override clutch may utilize a wrapped left-handed spring. This will allow the device to be advanced and the clutch disengaged for withdrawal by unwinding the spring a fraction of a turn to increase the ID and prevent gripping. Other commonly known clutch designs could also be integrated within the coupling.

Rotational Aides

An ergonomic grip or grips may be incorporated into the length of the catheter system to facilitate rotation of the helical device. These grips may be permanent or temporary, such as peel-away, so they can be removed or relocated during the procedure. The grips may be elastomeric or rigid and sized to fit comfortably in the hand. They may also be integrated with a powered drive within the grip.

Further Constructions

It will be appreciated that still further embodiments of the present invention will be apparent to those skilled in the art in view of the present disclosure. It is to be understood that the present invention is by no means limited to the particular constructions herein disclosed and/or shown in the drawings, but also comprises any modifications or equivalents within the scope of the invention. Further, although the present invention is been described with reference to particular examples and exemplary embodiments, it should be understood that the description is in no manner limiting. Moreover, the features described herein may be used in any combination.

What is claimed is:

1. An apparatus configured to access a passageway comprising:
   a visualization apparatus configured to visualize an interior surface of the passageway;
   a tube being configured to receive the visualization apparatus;
   a helically-wound thread disposed on an outer wall of the tube and configured such that rotation of the tube causes the tube with the visualization apparatus to move along the passageway;
   an inner rotor disposed in the visualization apparatus;
   a watertight cover being configured to cover an outer surface of the inner rotor such that the watertight cover separates inside and outside of the visualization apparatus, the inner rotor being configured to contact with an interior surface of the watertight cover, wherein one or more projections are configured to form on an outer surface of the watertight cover; and
   an outer rotor configured to engage the one or more projections such that rotary motion of the inner rotor is transferred to the outer rotor across the one or more projections, the tube being configured such that the tube is coupled with the outer rotor, wherein the rotary motion transferred across the one or more projections causes the tube to rotate with the outer rotor.

2. The apparatus according to claim 1, further comprising a stator and a housing, wherein: the inner rotor is rotatable over the stator, the housing is configured to receive the inner rotor and the stator, and the watertight cover includes a tubular member that covers the inner rotor which is exposed outside of the housing.

3. The apparatus according to claim 2, wherein: distal and proximal ends of the watertight cover are water-tightly fixed to a surface of the stator, and the watertight cover is configured to protect the inner rotor against exposure to water or other fluids.

4. The apparatus according to claim 1, wherein the rotary motion of the inner rotor causes the one or more projections to move in rotational direction of the inner rotor, and the outer rotor rotates in accordance with motion of the one or more projections.

5. The apparatus according to claim 1, wherein the inner rotor includes one or more carrying rollers disposed on the outer surface of the inner rotor, and the one or more carrying rollers causes the watertight cover to form the one or more projections.

6. The apparatus according to claim 5, wherein the outer rotor includes housing rollers disposed on the inner surface of the outer rotor, one of the one or more carrying rollers is positioned between the housing rollers over the watertight cover wherein the carrying rollers and the housing rollers roll the surface of the watertight cover to reduce the friction caused by the watertight cover while rotating the inner rotor.

7. The apparatus according to claim 1, wherein the inner rotor includes a rotary gear disposed in an inner surface of the inner rotor, the housing includes one or more transmission gears disposed in the housing and configured to transfer a power to the rotary gear so as to rotate the inner rotor.

8. An introducer configured to access a passageway comprising:
   a tube configured to receive a visualization apparatus configured to visualize an interior surface of the passageway, the visualization apparatus including:
      an inner rotor disposed in the visualization apparatus, and
      a watertight cover being configured to cover an outer surface of the inner rotor such that the watertight cover separates inside and outside of the visualization apparatus, the inner rotor being configured to contact with an interior surface of the watertight cover, wherein one or more projections are configured to form on an outer surface of the watertight cover;
   an outer rotor being configured to engage the one or more projections such that rotary motion of the inner rotor is transferred to the outer rotor across the one or more projections, the tube being configured such that the tube is coupled with the outer rotor and the rotary motion transferred across the one or more projections causes the tube to rotate with the outer rotor: and
   a helically-wound thread disposed on an outer wall of the tube and configured such that rotation of the tube causes the tube with the visualization apparatus to move along the passageway.

9. The introducer according to claim 8 wherein a cross-sectional shape of the outer rotor is configured to form an odd shaped, so that the outer rotor is coupled together with the one or more projections.

10. An endoscope configured to access a passageway comprising:
   a visualization apparatus configured to visualize an interior surface of the passageway;
   an inner rotor disposed in the visualization apparatus; and
   a watertight cover being configured to cover an outer surface of the inner rotor such that the watertight cover separates inside and outside of the visualization apparatus, the inner rotor being configured to contact with an interior surface of the watertight cover, wherein one or more projections are configured to form on an outer surface of the watertight cover:
   an outer rotor configured to engage the one or more projections such that rotary motion of the inner rotor is transferred to the outer rotor across the one or more projections,
   a tube detachably coupled with the outer rotor wherein the rotary motion transferred across the one or more projections causes the tube to rotate with the outer rotor, the tube being configured to receive the visualization apparatus, and
   a helically-wound thread disposed on an outer wall of the tube and configured such that rotation of the tube causes the tube with the visualization apparatus to move along the passageway.

* * * * *